(12) United States Patent
Liang et al.

(10) Patent No.: US 12,275,734 B1
(45) Date of Patent: Apr. 15, 2025

(54) PLEUROMUTILIN ONIUM SALT DERIVATIVE CONTAINING A 3H-IMIDAZO[4,5-C]PYRIDINE SIDE CHAIN, AND A PREPARATION METHOD AND APPLICATION THEREOF

(71) Applicant: SHAANXI UNIVERSITY OF SCIENCE AND TECHNOLOGY, Shaanxi (CN)

(72) Inventors: Chengyuan Liang, Xi'an (CN); Yanzi Wang, Xi'an (CN); Kairui Kang, Xi'an (CN); Bingxing Zhang, Xi'an (CN); Wen Wang, Xi'an (CN); Yunfei Zhang, Xi'an (CN); Mengzhou Wang, Xi'an (CN)

(73) Assignee: SHAANXI UNIVERSITY OF SCIENCE AND TECHNOLOGY, Shaanxi (CN)

( * ) Notice: Subject to any disclaimer, the term of this patent is extended or adjusted under 35 U.S.C. 154(b) by 0 days.

(21) Appl. No.: 18/951,509

(22) Filed: Nov. 18, 2024

(30) Foreign Application Priority Data

May 15, 2024 (CN) .......................... 202410603851.9

(51) Int. Cl.
*C07D 471/04* (2006.01)
*A61K 31/437* (2006.01)
*A61P 31/04* (2006.01)

(52) U.S. Cl.
CPC .......... *C07D 471/04* (2013.01); *A61K 31/437* (2013.01); *A61P 31/04* (2018.01)

(58) Field of Classification Search
CPC ...... C07D 471/04; A61K 31/437; A61P 31/04

USPC ........................................ 546/118; 514/303
See application file for complete search history.

(56) References Cited

U.S. PATENT DOCUMENTS 11,555,016 B2 * 1/2023 Wang .................. C07D 215/233

* cited by examiner

*Primary Examiner* — Charanjit Aulakh

(57) ABSTRACT

A compound of formula I, a pharmaceutically acceptable salt thereof, or a solvent compound, an enantiomer, a diastereomer or a tautomer of the compound or a pharmaceutically acceptable salt thereof is disclosed. The 3H-imidazo[4,5-C] pyridine pleuromutilin onium salt derivatives exhibit good water solubility and excellent activity against resistant *mycoplasma*, in vivo and in vitro antibacterial activity, and are of great value in the development of anti-resistant bacteria drugs and have good medical application prospects.

Formula I

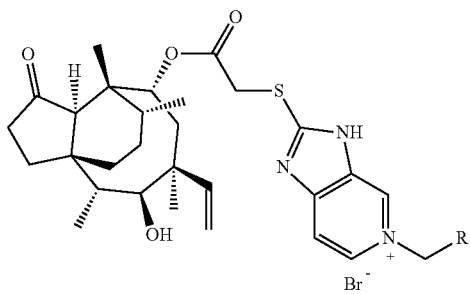

8 Claims, 34 Drawing Sheets

PLEUROMUTILIN ONIUM SALT DERIVATIVE CONTAINING A 3H-IMIDAZO[4,5-C]PYRIDINE SIDE CHAIN, AND A PREPARATION METHOD AND APPLICATION THEREOF

This application claims priority to Chinese Patent Application No. 202410603851.9, filed on May 15, 2024, which is incorporated by reference for all purposes as if fully set forth herein.

TECHNICAL FIELD

The present invention belongs to the technical field of medicinal chemistry, and specifically relates to a class of 3H-imidazo[4,5-C]pyridine pleuromutilin onium salt derivatives, and a preparation method and application thereof.

BACKGROUND TECHNIQUE

Pleuromutilin represent a new class of antibiotics designed to combat bacteria resistant to conventional antibiotics. These compounds belong to the broader family of pleuromutilin and exhibit a unique antibacterial mechanism, primarily inhibiting bacterial protein synthesis. This mechanism enables them to effectively target hard-to-treat bacteria, such as Gram-positive strains. While pleuromutilin demonstrate strong antibacterial activity, they are not without limitations. Notably, issues of cytotoxicity may restrict their dosage. Furthermore, although this class of antibiotics can address certain resistant bacteria, ongoing research and development are required to enhance their efficacy as bacterial resistance continues to evolve.

Given the growing problem of antibiotic resistance worldwide, the development of new antibiotics such as pleuromutilin is particularly important. This not only helps provide more treatment options, but is also one of the important strategies of the World Health Organization to face the challenge of drug resistance. Therefore, strengthening the research and improvement of this type of antibiotics, as well as the rational use of antibiotics, are key measures to address the spread of bacterial resistance.

SUMMARY OF THE INVENTION

In one embodiment, the present application discloses compound of formula I, a pharmaceutically acceptable salt, a diastereomer, or a tautomer thereof:

Formula I

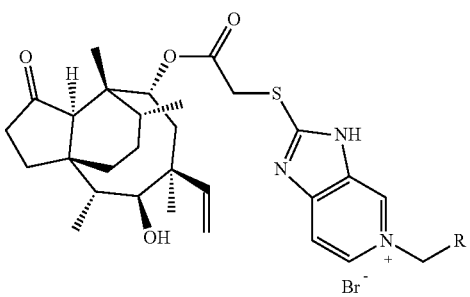

R is a phenyl group substituted with an electron withdrawing group or a phenyl group substituted with an electron donating group.

In another embodiment, the compound is selected from the group consisting of:

a

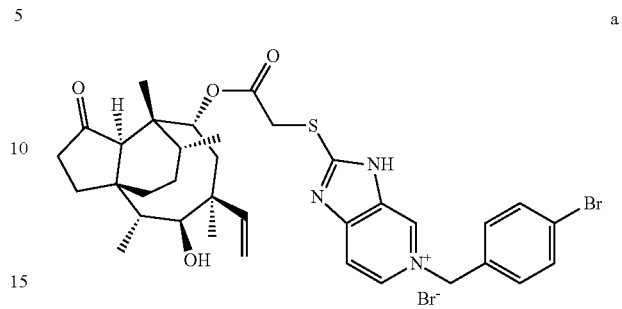

b

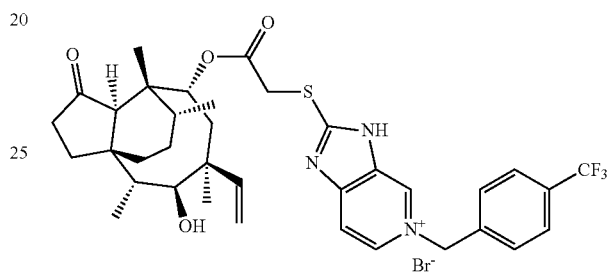

c

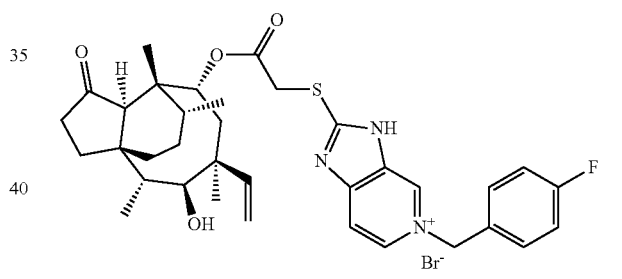

d

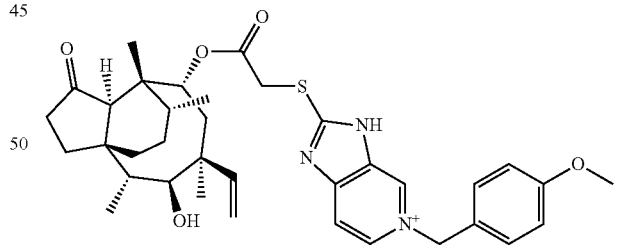

e

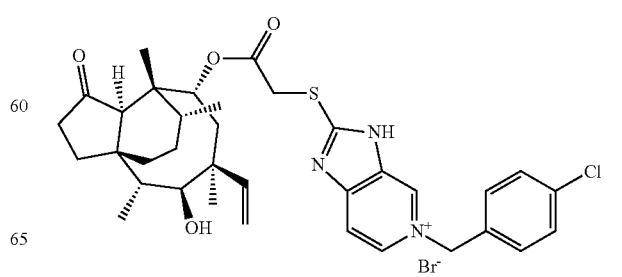

f

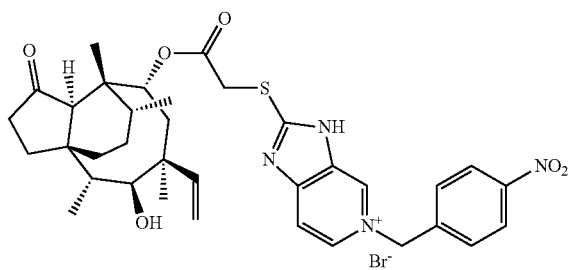

g

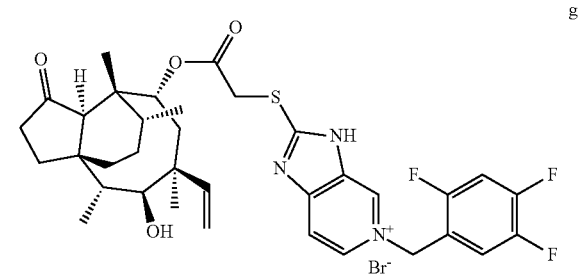

h

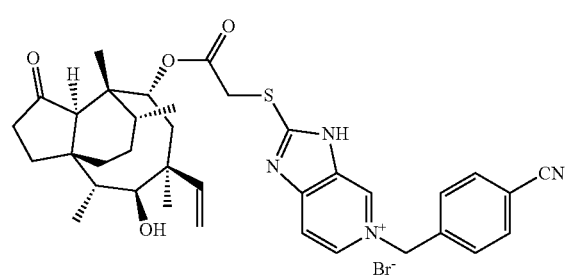

i

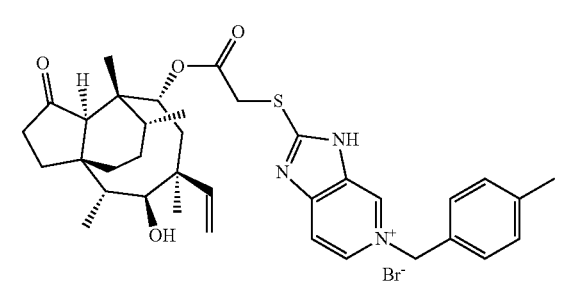

j

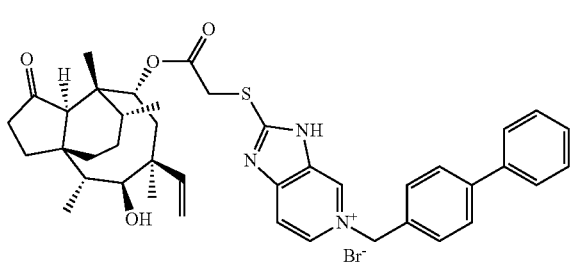

k

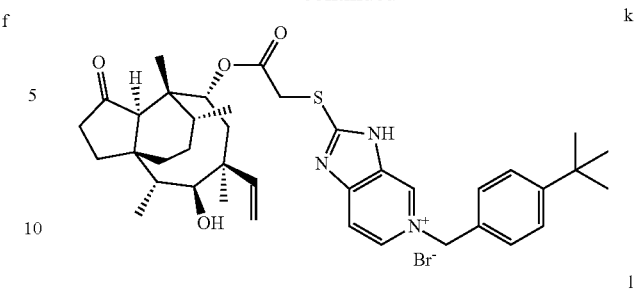

l

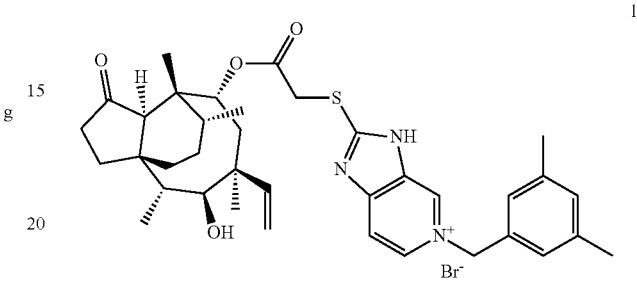

m

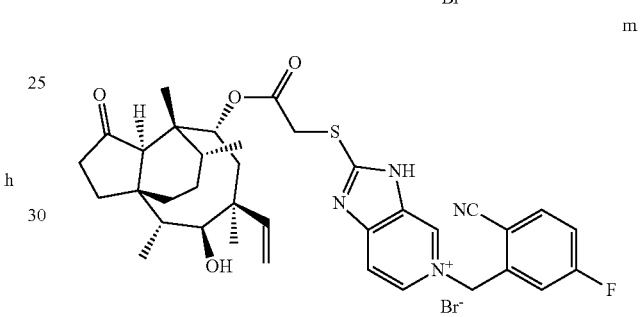

n

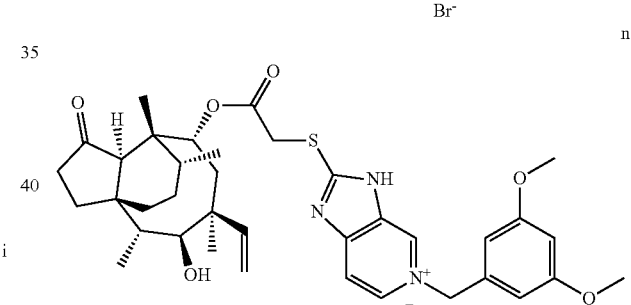

In another embodiment, the pharmaceutically acceptable salts includes one selected from the group consisting of hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid or aspartic acid.

In another embodiment, the present application discloses the use of the compound in the preparation of a drug for treating infectious diseases caused by pathogenic microorganisms, wherein the pathogenic microorganisms are Gram-positive bacteria, Gram-negative bacteria, drug-resistant bacteria or *mycoplasma*.

Compared with the prior art, the present invention has the following beneficial effects:

The invention provides a class of 3H-imidazo[4,5-C] pyridine pleuromutilin onium salt derivatives, which have good water solubility, excellent anti-drug-resistant *mycoplasma* activity, and in vitro and in vivo antibacterial activity. After conducting in-depth research on the mechanism, it was proposed that this type of compound has a bactericidal mechanism that destroys bacterial cell walls and membranes and combines with active center of bacterial ribosomal 50S subunit peptidyl transferase. Its efficacy and safety are significantly better than those of already-marketed pleuromutilin antibiotics such as retapamulin. These results show its important value in the development of anti-drug-resistant bacteria and has good pharmaceutical application prospects.

The preparation method of the 3H-imidazo[4,5-C]pyridine pleuromutilin onium salt derivatives provided by the present invention has readily available raw materials, high operational safety, mild reaction conditions and low cost, a yield of 63.76% to 78.56%, a high yield and is suitable for industrial production.

The 3H-imidazo[4,5-C]pyridine pleuromutilin onium salt derivatives described in the present invention exhibit enhanced antibacterial activity with reduced cytotoxicity and are suitable for the treatment of infectious diseases, particularly those caused by drug-resistant bacteria.

DETAILED DESCRIPTION OF EMBODIMENTS

Figure 1:
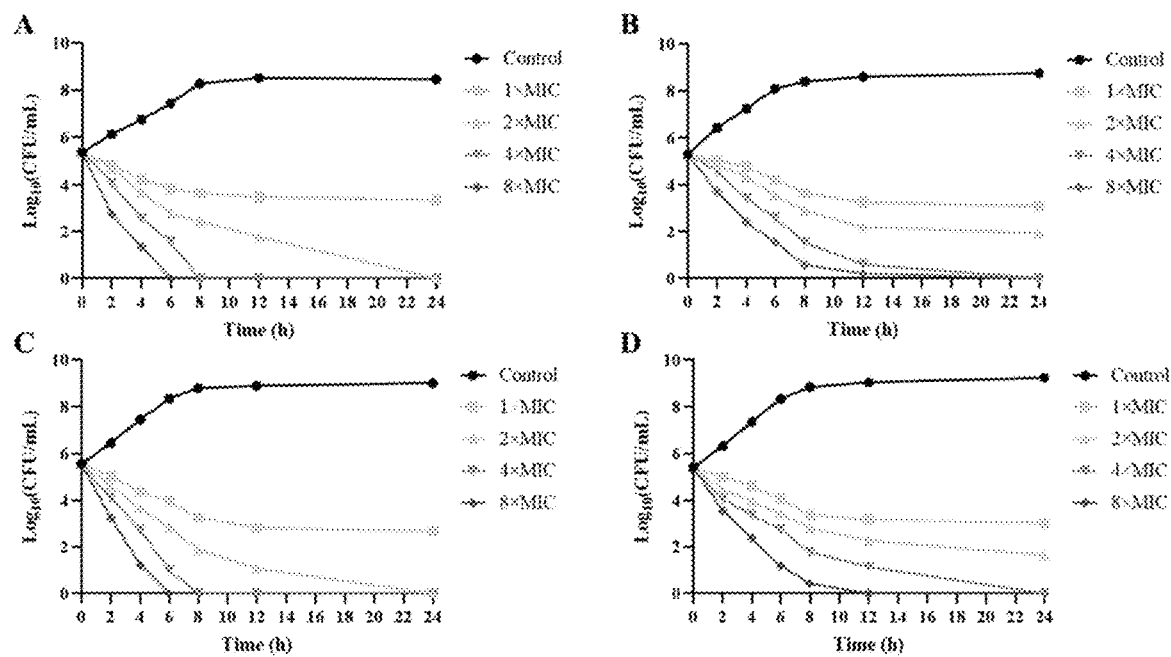
FIG. 1 shows the time-kill curves of Compound i and retapamulin at different concentrations. A shows the time-kill curve of Compound i against MRSA (ATCC 33591); B shows the time-kill curve of retapamulin against MRSA (ATCC 33591); C illustrates the time-kill curve of Compound i against *E. coli* (ATCC 25922); and D shows the time-kill curve of retapamulin against *E. coli* (ATCC 25922).

The following describes the embodiments of the present invention through specific examples, and those skilled in the art can easily understand other advantages and effects of the present invention from the contents disclosed in this specification. The present invention can also be implemented or applied through other different specific embodiments, and the details in this specification can also be modified or changed in various ways based on different viewpoints and applications without departing from the spirit of the present invention.

The pleuromutilin onium salt derivatives containing 3H-imidazo[4,5-C]pyridine side chains of the present invention are compounds having a structural formula as shown in Formula I, or pharmaceutically acceptable salts thereof, or solvent compounds, enantiomers, diastereomers, tautomers or mixtures thereof in any proportion, including racemic mixtures, of the compounds shown in Formula I or pharmaceutically acceptable salts thereof.

Formula I

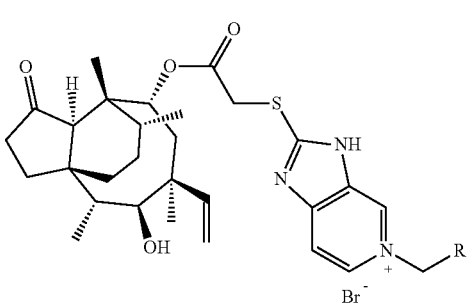

Wherein, R is a phenyl group substituted with an electron-withdrawing group or a phenyl group substituted with an electron-donating group, the electron withdrawing group is a bromine substituent, a trifluoromethyl substituent, a fluorine substituent, a chlorine substituent, a nitro group or a cyano group, and the electron donating group is a methyl group, a phenyl group, a tert-butyl group or a methoxy group.

Wherein, R is selected from the group consisting of the following:

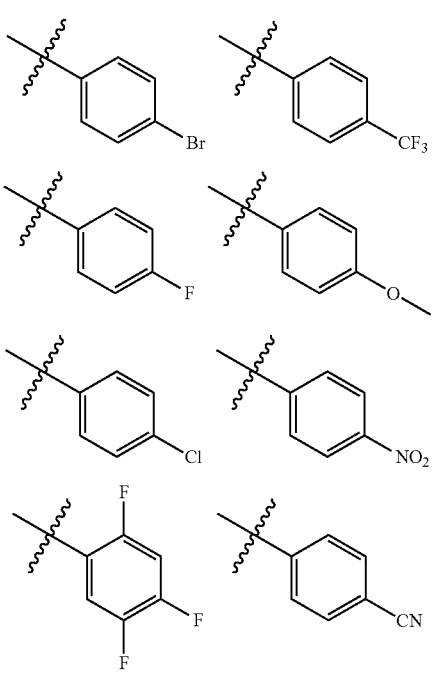

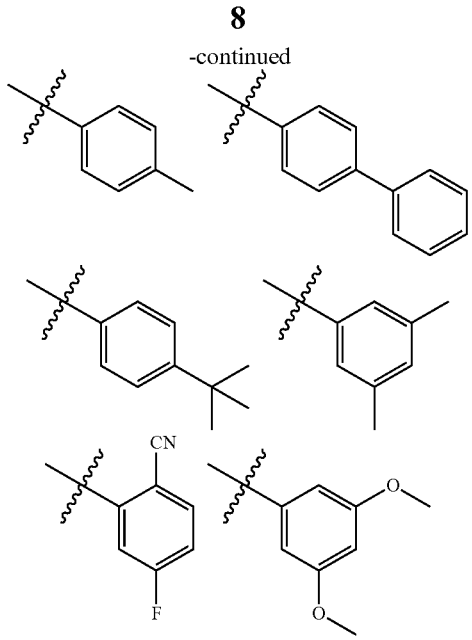

The pharmaceutically acceptable salts includes a salt selected from the group consisting of hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid or aspartic acid.

The compounds of the present application can be synthesized by a method that includes the following operation steps:

(1) Pleuromutilin is reacted with tosyl chloride to obtain intermediate I.

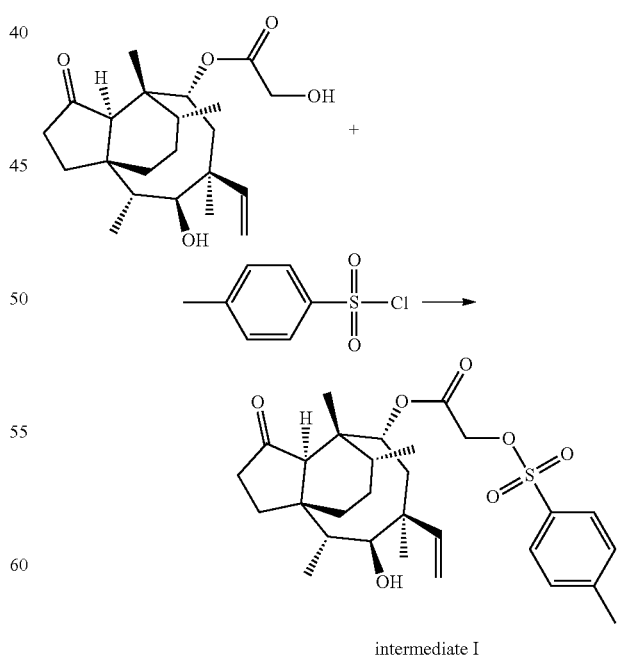

intermediate I (2) 3,4-diaminopyridine is reacted with potassium ethylxanthate to obtain intermediate II.

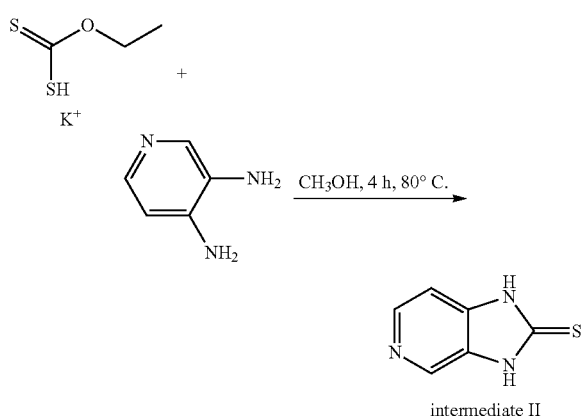

intermediate II (3) Intermediate I is reacted with intermediate II under alkaline catalyst conditions with heating to obtain intermediate III.

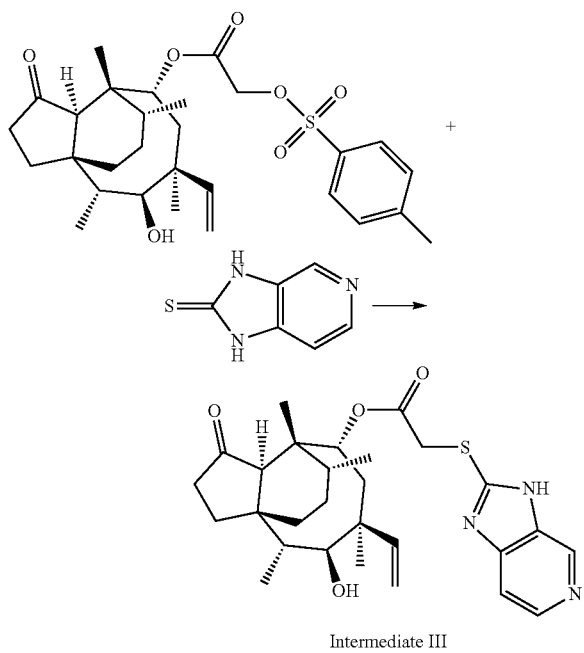

Intermediate III (4) Intermediate III is reacted with a benzene ring compound containing a substituent to obtain a pleuromutilin onium salt derivatives shown in general formula I.

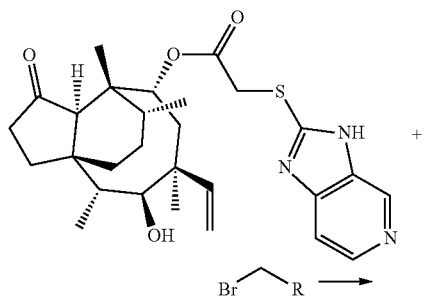

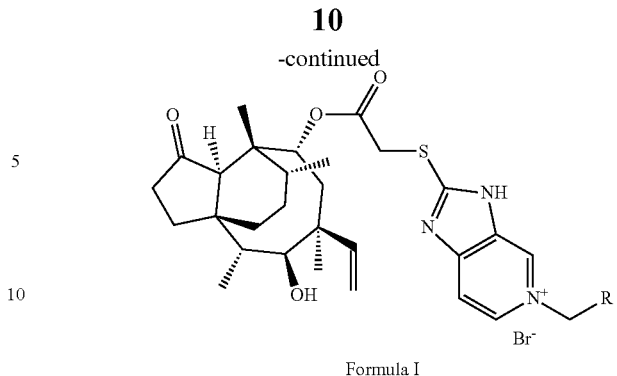

Formula I

Wherein, the reaction solvent can be selected from acetonitrile, toluene or acetone; the reaction is carried out at room temperature for 8 to 12 hours. The aromatic hydrocarbon compound containing a substituent is p-bromobenzyl bromide, 4-(trifluoromethyl)benzyl bromide, p-fluorobenzyl bromide, 4-methoxybenzyl bromide, 4-chlorobenzyl bromide, p-1 bromide, 1-bromo-2,4,5-trifluorobenzene, 4-cyanobenzyl bromide, p-nitrobenzyl methylbenzyl bromide, 4-bromomethylbiphenyl, 4-tert-butylbenzyl bromide, 3,5-dimethylbenzyl bromide, 2-cyano-5-fluorobenzyl bromide or 3,5-dimethoxybenzyl bromide.

In a specific embodiment of the present invention, in step (1), the solution used in the reaction is dichloromethane; the molar ratio of the pleuromutilin to tosyl chloride is 1:1.2; in step (2), the solution used in the reaction is N,N-dimethylformamide, and the molar ratio of the 3,4-diaminopyridine to potassium ethylxanthate is 1:1.2; in step (3), the solvent used in the reaction is N,N-dimethylformamide; in step (4), the solvent used in the reaction is acetonitrile, toluene or acetone. The reaction conditions are room temperature for 8-12 hours.

The pleuromutilin onium salt derivatives containing 3H-imidazo[4,5-C]pyridine side chains of the present invention have the effect of resisting pathogenic microorganisms and can be used for preparing drugs for treating infectious diseases caused by pathogenic microorganisms.

Wherein, the infectious disease is caused by pathogenic microorganisms, the pathogenic microorganism is Gram-positive bacteria, Gram-negative bacteria, drug-resistant bacteria or *mycoplasma*.

Wherein, the Gram-positive bacteria are: Methicillin-resistant *S. aureus* ATCC 33591, Methicillin-resistant *S. aureus* ATCC 43300, *S. aureus* ATCC 29213 or Methicillin-resistant *S. epidermidis* ATCC 51625; the Gram-negative bacteria are *A. baumannii* ATCC 19606, *S. enterica* ATCC14028, *E. coli* ATCC 25922 or *E. coli* CMCC 44103.

Wherein, the drug-resistant bacteria are MRSA-171, MRSA-575, MRSA-206, MRSA-222, MRSA-596, VRE-80, MDR-PA-126, MDR-KP-893 or CR-AB-882.

Wherein, the mycoplasmas are *M. hyopneumoniae* J (NCTC10110), *M. hyopneumoniae* LH (clinical isolate), *M. hyorhinis* BTS-7 (NCTC10130), *M. galliscepticum* (NCTC10115), *M. synoviae* WVU1853 (NCTC10124), *M. pneumoniae* M129 (ATCC29342), *C. pneumoniae* AR39 (ATCC53592), *C. pneumoniae* CWL-029 (VR-1310), *C. pneumoniae* TW183 (VR-2282), *M. hominis* PG-21 (ATCC23114), *M. genitalium* G37 (ATCC33530).

The 3H-imidazo[4,5-C]pyridine pleuromutilin onium salt derivatives are used alone or mixed with pharmaceutically acceptable excipients and diluents to form tablets, capsules, granules, syrups, premixes or pellets for oral administration, or are made into ointments or injections for non-oral administration.

The present invention also discloses a pharmaceutical composition, which contains an effective amount of the above-mentioned 3H-imidazo[4,5-C]pyridine pleuromutilin onium salt derivatives, and the remainder is pharmaceutical adjuvant or other compatible drugs.

Synthesis examples of the compounds are given below.

Example 1

Preparation of Compound a: 5-(4-bromobenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8]cyclo-5-yl)oxy)-2-oxoethyl)thio)-3H-imidazo[4,5-c]pyridin-5-ium (1) Preparation of Compound Intermediate I

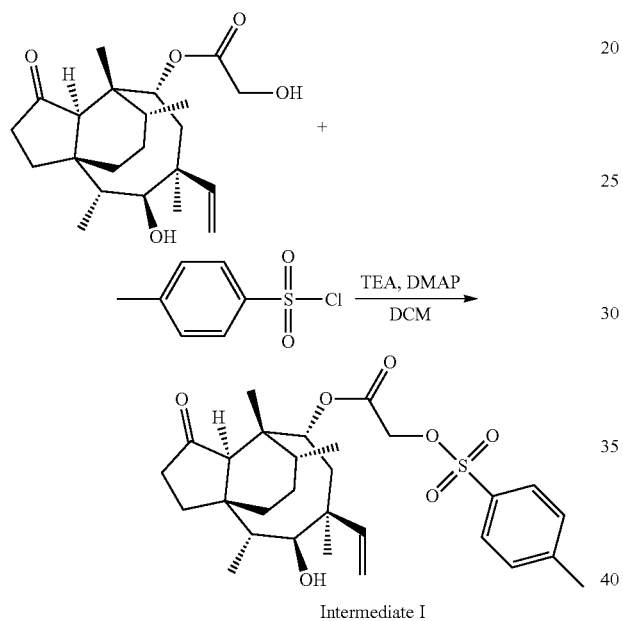

Intermediate I

Pleuromutilin (7.57 g, 20 mmol), tosyl chloride (4.58 g, 24 mmol) and 4-dimethylaminopyridine (0.25 g, 2 mmol) were added to a solvent of dichloromethane (100 mL), stirred to dissolve, and then triethylamine (8.35 mL, 60 mmol) was added, stirred at room temperature for 8 h, and reacted. After the reaction was completed, the reaction solution was concentrated, then washed with a saturated NaHCO$_3$ aqueous solution, and finally vacuum dried to obtain intermediate I with a yield of about 96%.

(2) Preparation of Compound Intermediate II

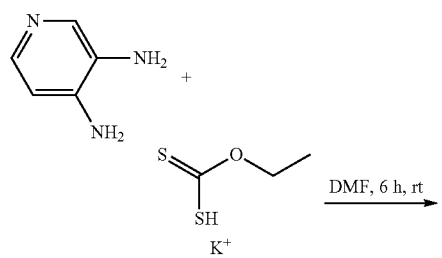

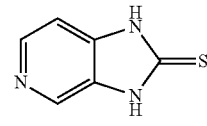

Intermediate II 3,4-diaminopyridine (1.0 g, 9.16 mmol), potassium ethylxanthate (1.1 g, 28 mmol), EtOH (7 mL), and H$_2$O (1 mL) were placed in a reactor, refluxed and stirred at 80° C. overnight, and the solvent in the reaction solution was removed by reduced pressure concentration to obtain a residue. The residue was separated and purified by column chromatography, using 200-300 mesh silica gel as the stationary phase and dichloromethane:methanol (10:1 V/V) as the mobile phase. The solid powder obtained from the column chromatography separation and purification was intermediate II, and the yield was about 94%.

(3) Preparation of Compound Intermediate III

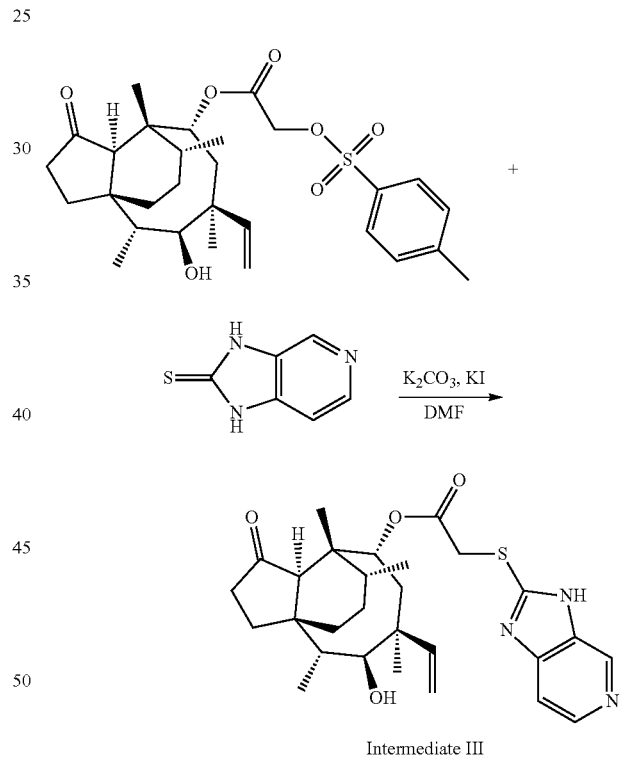

Intermediate III

Intermediate I (5.33 g, 10 mmol), intermediate II (1.82 g, 12 mmol), potassium carbonate (2.77 g, 20 mmol) and potassium iodide (0.16 g, 1 mmol) were added to 50 mL of N,N dimethylformamide solvent, dissolved, and heated to 60° C. for 6 hours. After the reaction, 200 mL of saturated ammonium chloride aqueous solution was added to the reaction solution, and ethyl acetate was used for extraction. The ethyl acetate phase was concentrated and separated by column chromatography to obtain intermediate III. The eluent used for column chromatography was a dichloromethane-methanol mixture with a volume ratio of 18:1, and the yield was 82%.

(4) Preparation of Compound a

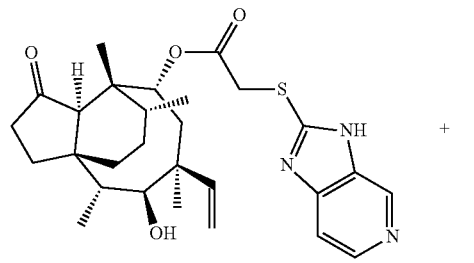

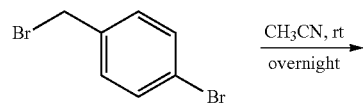

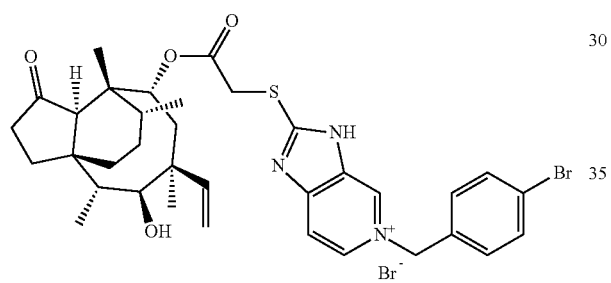

Figure 12:
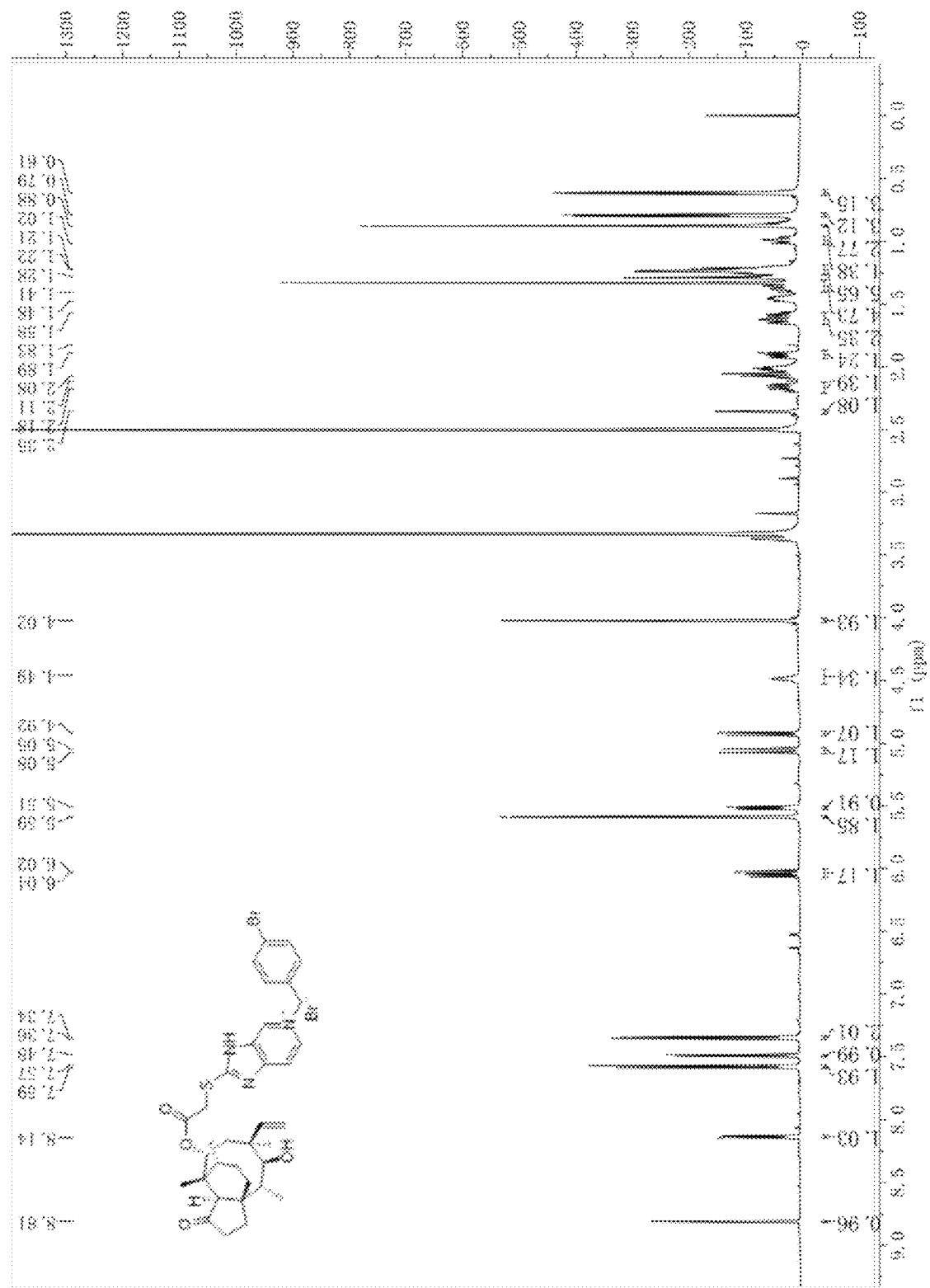
FIG. 12 is a $^1$H NMR spectrum of Compound a of the present invention in deuterated DMSO.
Figure 13:
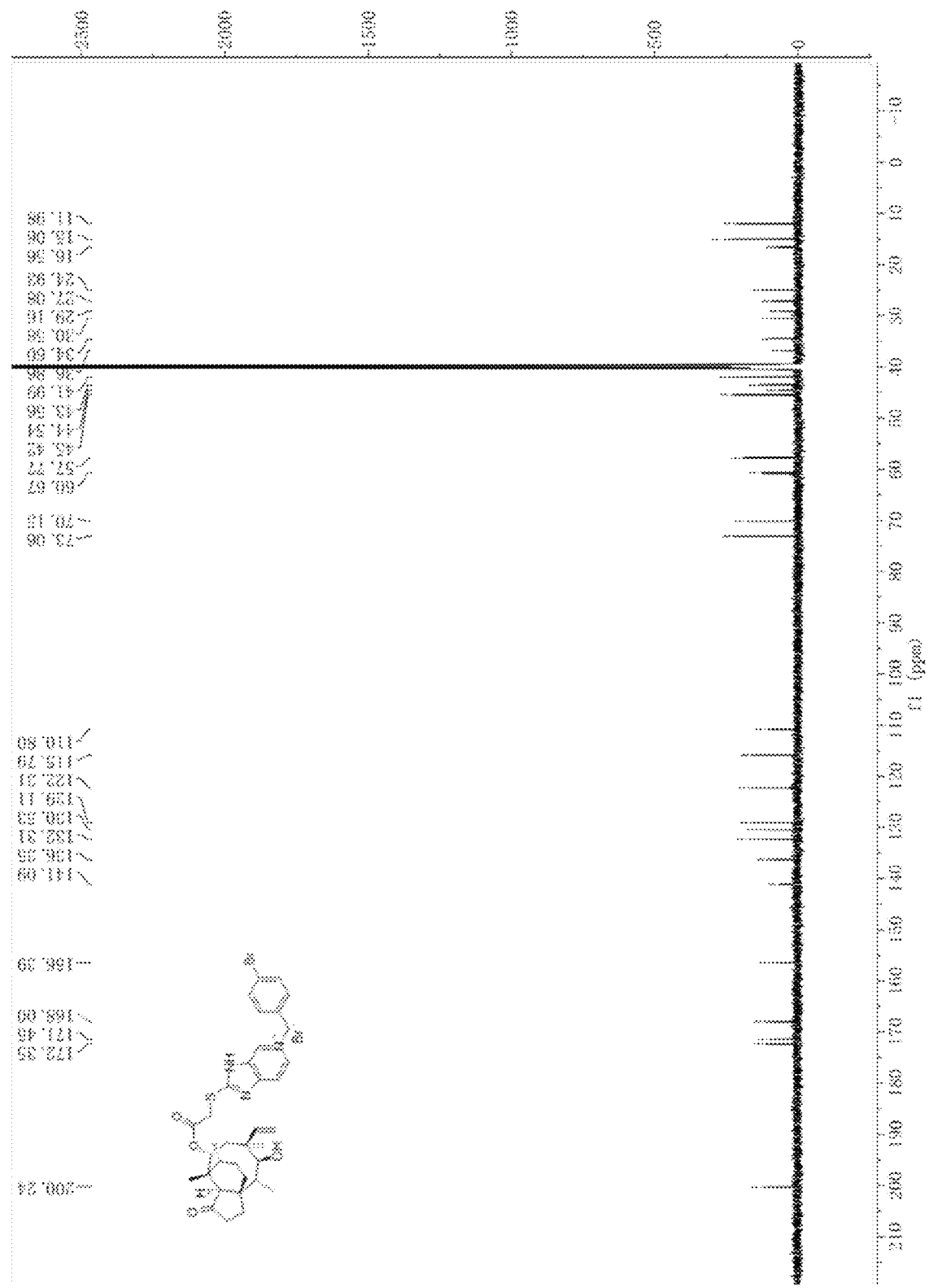
FIG. 13 is a $^{13}$C NMR spectrum of Compound a of the present invention in deuterated DMSO.

Intermediate III (0.256 g, 0.5 mmol) and 4-bromobenzyl bromide (0.375 g, 1.5 mmol) were dissolved in acetonitrile (5 mL), reacted at room temperature for 12 h, concentrated under reduced pressure to remove the solvent, and purified by column chromatography to obtain Compound a. The eluent for column chromatography was dichloromethane:methanol=(12~8): 1, with a yield of 71%. The 1H NMR spectrum of Compound a in deuterated DMSO is as shown in FIG. 12, and the 13C NMR spectrum in deuterated DMSO is as shown in FIG. 13.

$^1$H NMR (600 MHZ, DMSO-d6) δ 8.81 (d, J=1.6 Hz, 1H), 8.14 (dd, J=6.8, Hz, 1H), 7.59-7.57 (m, 2H), 7.49 (d, J=6.7 Hz, 1H), 7.36-7.33 (m, 2H), 6.04 (dd, J=11.2 Hz, 1H), 5.59 (s, 2H), 5.52 (d, J=8.4 Hz, 1H), 5.06 (dd, J=7.8 Hz, 1H), 4.93 (dd, J=11.2, 1.7 Hz, 1H), 4.49 (s, 1H), 4.02 (s, 2H), 2.36 (d, J=2.6 Hz, 1H), 2.17 (dd, J=8.2, 1H), 2.11 (d, J=6.2, 1H), 1.91 (dd, J=8.4 Hz, 2H), 1.62 (dd, J=4.8 Hz, 5H), 1.33 (s, 6H), 1.29-1.18 (m, 1H), 0.88 (s, 3H), 0.79 (d, J=7.0 Hz, 3H), 0.62 (d, J=7.0 Hz, 3H).

$^{13}$C NMR (151 MHz, DMSO-d6) δ 200.24, 172.35, 171.45, 168.00, 156.39, 141.09, 136.35, 132.31, 130.53, 129.11, 122.31, 115.79, 110.80, 73.06, 70.15, 60.67, 57.77, 45.42, 44.54, 43.56, 41.99, 36.86, 34.60, 30.58, 29.16, 27.08, 24.93, 16.56, 15.06, 11.98.

Example 2

Preparation of Compound b: 5-(4-trifluoromethyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8]cyclo-5-yl)oxy)-2-oxoethyl)thio)-3H-imidazo[4,5-C]pyridine-5-ium

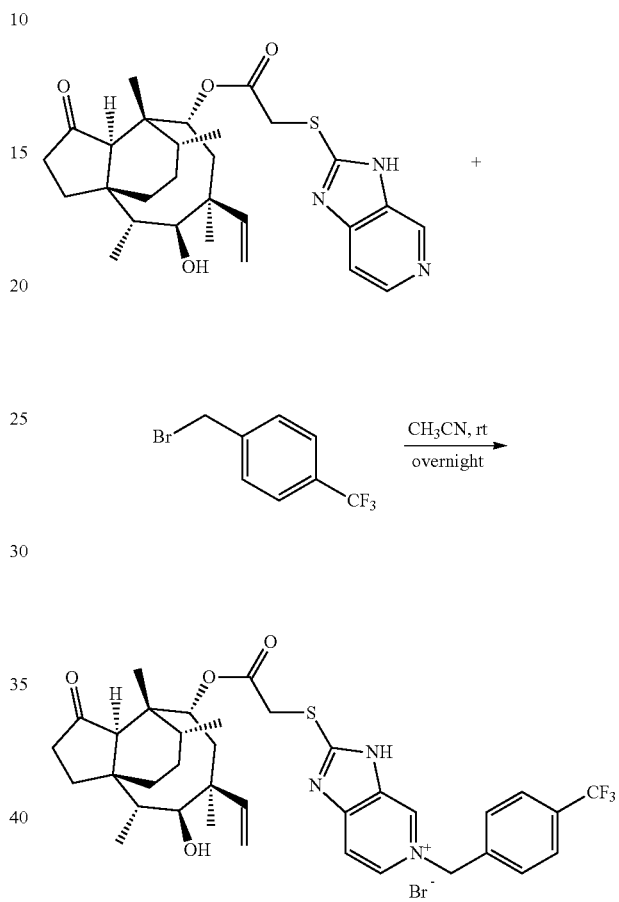

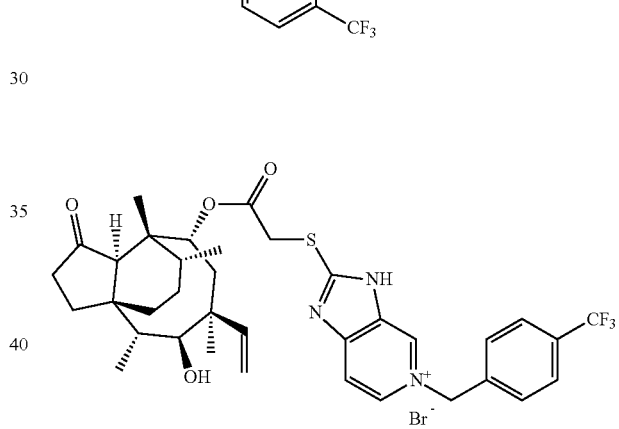

Figure 14:
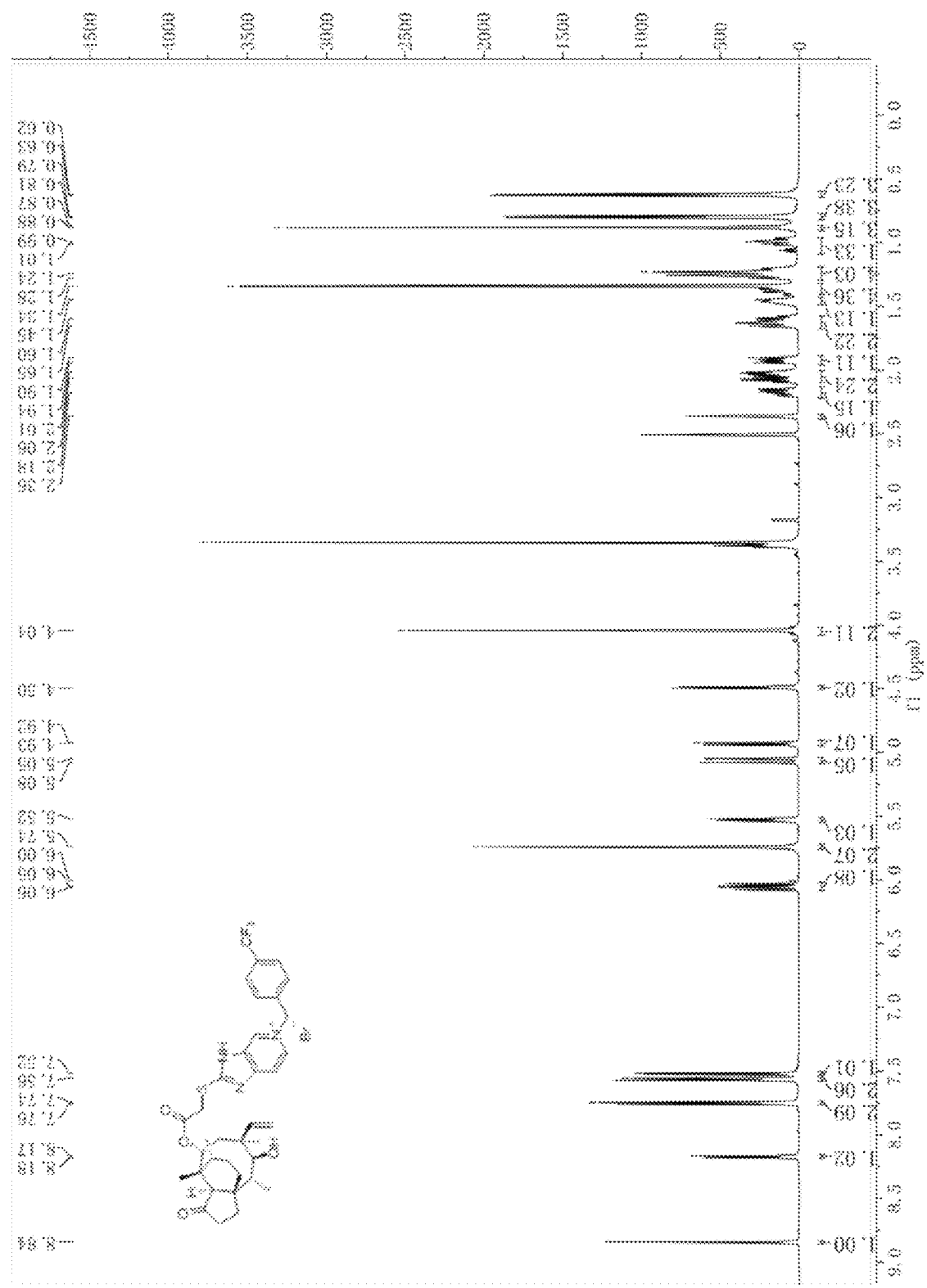
FIG. 14 is a $^1$H NMR spectrum of Compound b of the present invention in deuterated DMSO.
Figure 15:
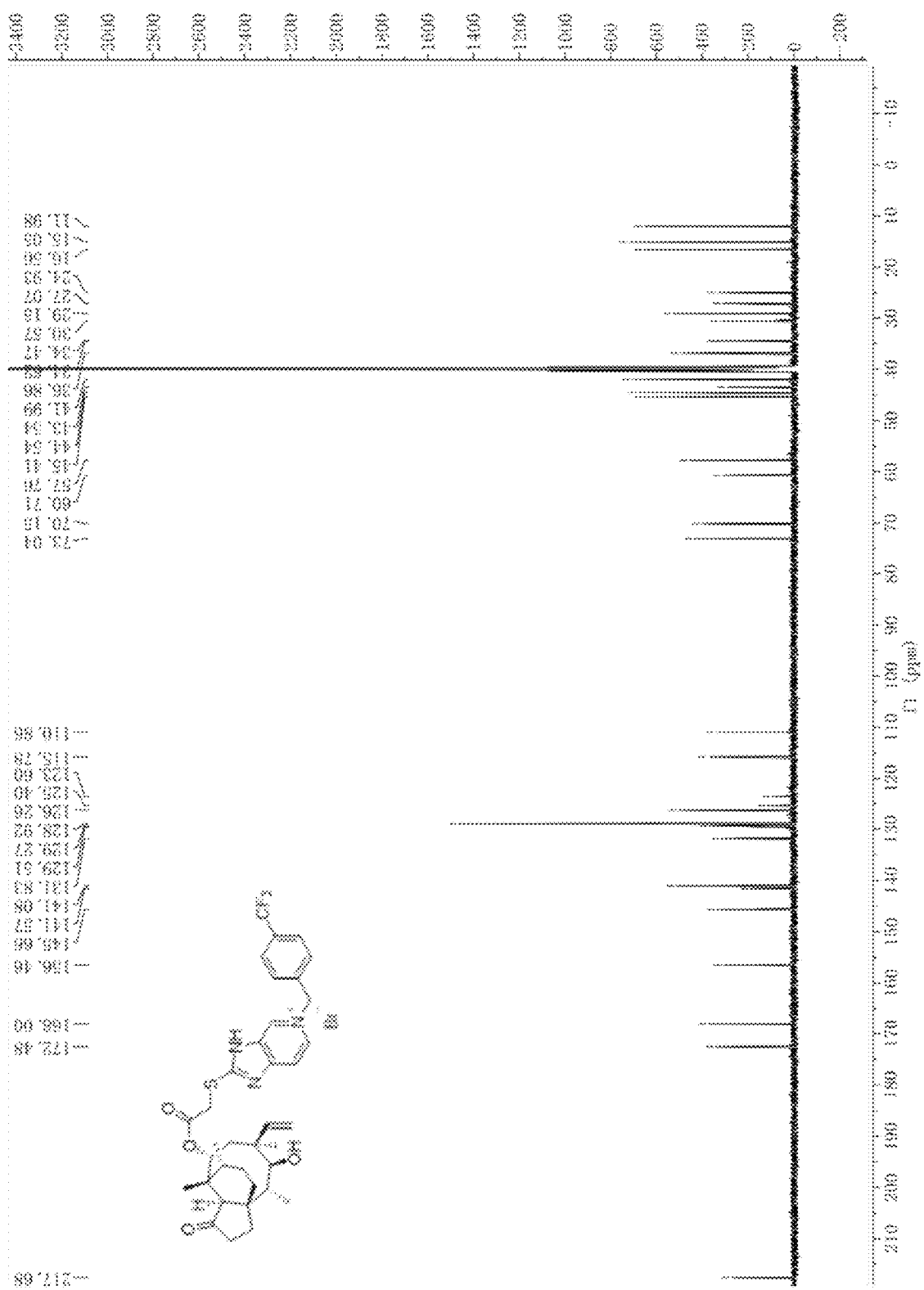
FIG. 15 is a $^{13}$C NMR spectrum of Compound b of the present invention in deuterated DMSO.

The preparation method was as described in Example 1, except that the corresponding raw materials were replaced. Yield of Compound b obtained: 76%. The 1H NMR spectrum of Compound b in deuterated DMSO is as shown in FIG. 14, and the 13C NMR spectrum in deuterated DMSO is as shown in FIG. 15.

$^1$H NMR (600 MHZ, DMSO-d6) δ 8.84 (d, J=1.6 Hz, 1H), 8.18 (dd, J=6.8, 1.6 Hz, 1H), 7.75 (d, J=8.1 Hz, 2H), 7.56 (d, J=8.0 Hz, 2H), 7.52 (d, J=6.7 Hz, 1H), 6.05 (dd, J=17.8, 11.2 Hz, 1H), 5.74 (s, 2H), 5.53 (d, J=8.4 Hz, 1H), 5.07 (dd, J=17.9, 1.8 Hz, 1H), 4.93 (dd, J=11.2, 1H), 4.49 (d, J=6.0 Hz, 1H), 4.04 (s, 2H), 2.36 (d, J=2.7 Hz, 1H), 2.22-2.13 (m, 1H), 2.10-2.00 (m, 2H), 1.92 (dd, J=8.4 Hz, 1H), 1.67-1.58 (m, 2H), 1.46 (dd, J=7.0, Hz, 1H), 1.34 (s, 4H), 1.30-1.19 (m, 4H), 0.99 (td, J=14.0, 4.4 Hz, 1H), 0.88 (s, 3H), 0.80 (d, J=7.0 Hz, 3H), 0.63 (d, J=7.0 Hz, 3H).

$^{13}$C NMR (151 MHZ, DMSO-d6) δ 217.68, 172.48, 168.00, 156.46, 145.66, 141.57, 141.08, 131.83, 129.51, 129.27, 128.92, 126.26, 125.40, 123.60, 115.78, 110.86, 73.04, 70.15, 60.71, 57.76, 45.41, 44.54, 43.54, 41.99, 36.86, 34.62, 34.47, 30.57, 29.15, 27.07, 24.93, 16.56, 15.05, 11.98.

Example 3

Preparation of Compound c: 5-(4-fluorobenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8]cyclo-5-yl)oxy)-2-oxoethyl)thio)-3H-imidazo[4,5-C]pyridine-5-ium

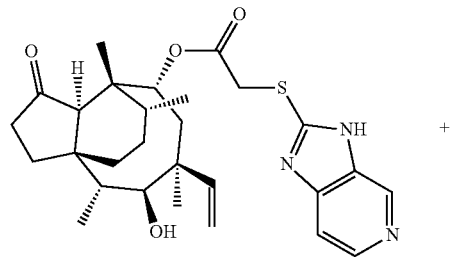

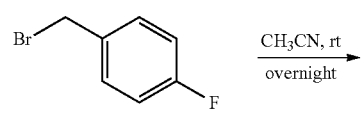

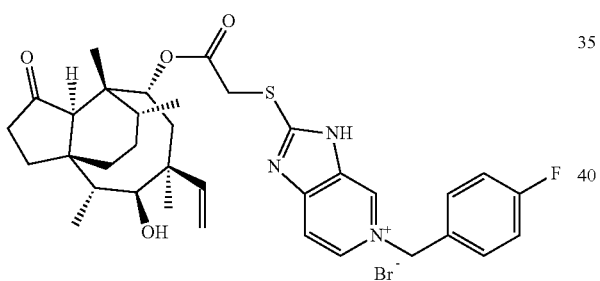

Figure 16:
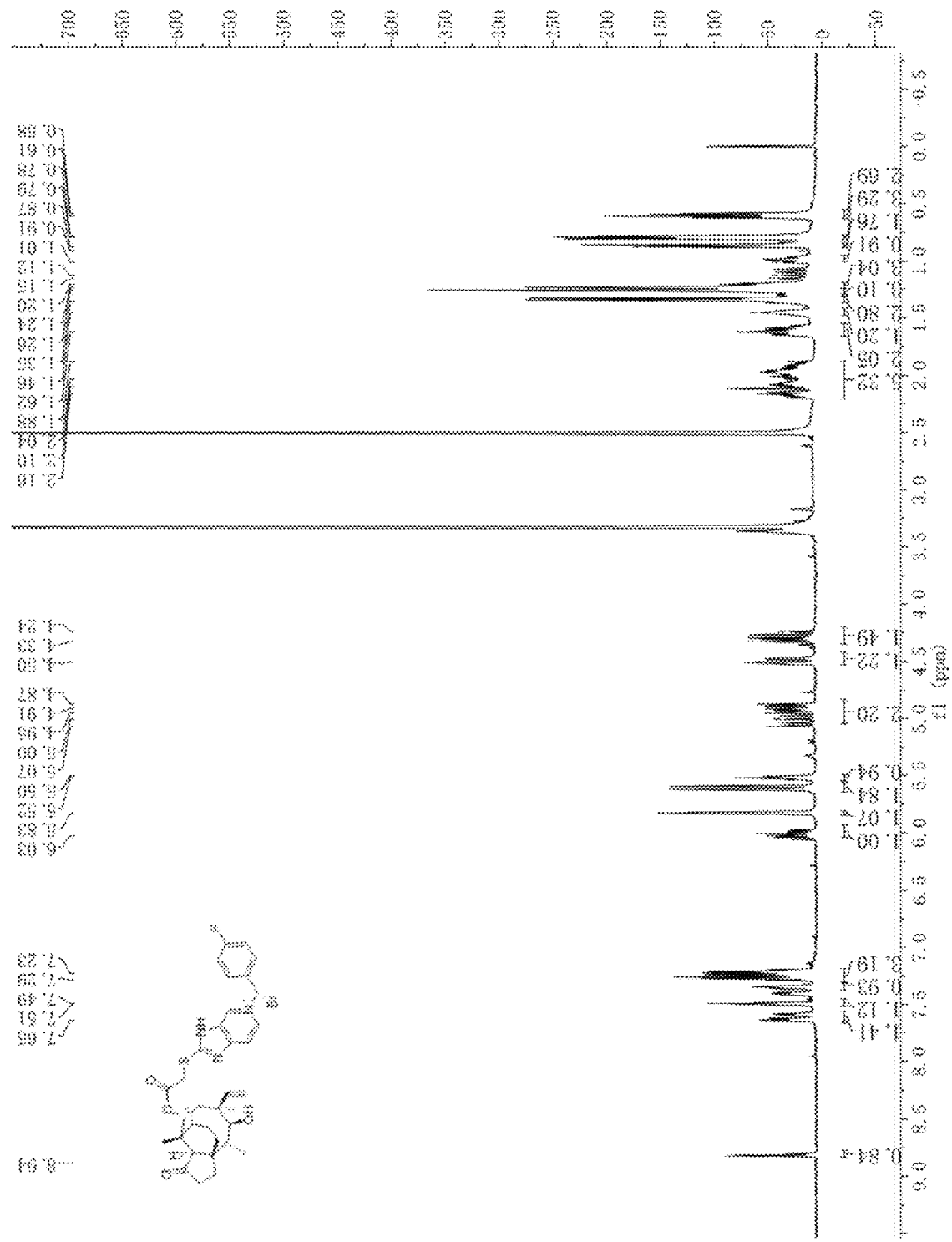
FIG. 16 is a $^1$H NMR spectrum of Compound c of the present invention in deuterated DMSO.
Figure 17:
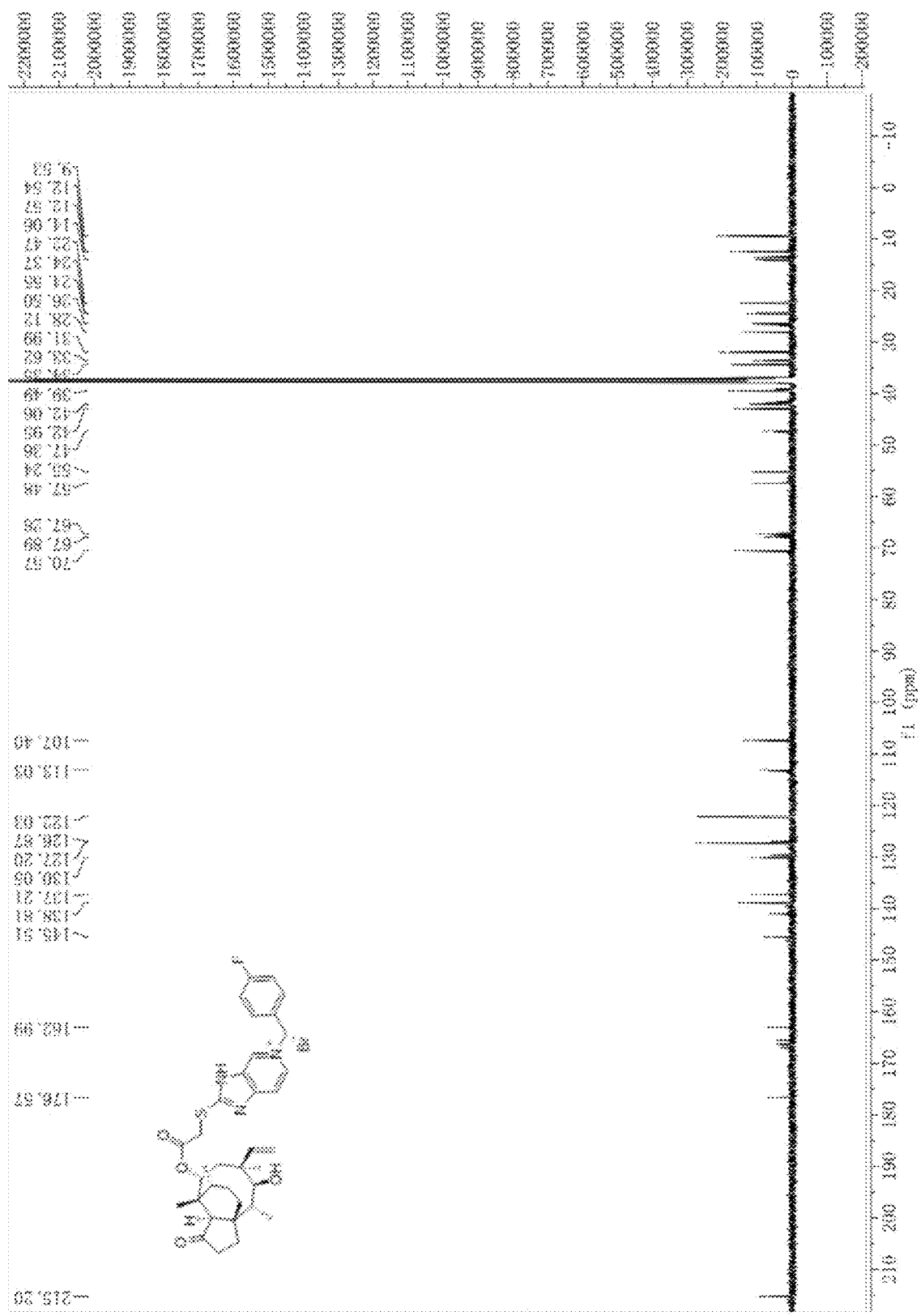
FIG. 17 is a $^{13}$C NMR spectrum of Compound c of the present invention in deuterated DMSO.

The preparation method was as described in Example 1, except that the corresponding raw materials were replaced. Yield of Compound c obtained: 73%. The 1H NMR spectrum of Compound c in deuterated DMSO is as shown in FIG. 16, and the 13C NMR spectrum in deuterated DMSO is as shown in FIG. 17.

$^1$H NMR (600 MHZ, DMSO-d6) δ 8.95 (d, J=7.0 Hz, 1H), 7.67 (m, 1H), 7.55 (m, 1H), 7.32 (m, 1H), 7.27-7.20 (d, J=8.6 Hz, 3H), 6.12-5.96 (d, J=6.4 Hz, 1H), 5.72-5.60 (d, J=6.4 Hz, 1H), 5.57-5.52 (d, J=5.4 Hz, 2H), 5.53-5.49 (m, 1H), 5.12-4.82 (d, J=6.2 Hz, 2H), 4.56-4.42 (m, 1H), 4.32-4.24 (m, 1H), 2.28-1.65 (d, J=9.3 Hz, 5H). 1.58-1.55 (m, 2H). 1.52-1.47 (m, 1H). 1.40-1.37 (m, 3H). 1.35-1.31 (m, 3H). 1.26-1.21 (m, 3H). 0.92 (d, J=8.2 Hz, 1H), 0.87 (d, J=9.3 Hz, 2H), 0.81-0.77 (m, 3H), 0.63-0.57 (m, 3H).

$^{13}$C NMR (151 MHz, DMSO-d6) δ 215.20, 176.57, 162.99, 145.51, 138.81, 137.21, 130.05, 127.20, 126.87, 122.03, 113.03, 107.40, 70.57, 67.89, 67.28, 57.48, 55.24, 47.36, 42.95, 42.06, 39.49, 34.35, 33.62, 31.99, 28.12, 26.50, 24.55, 24.37, 22.47, 14.06, 12.57, 12.54, 9.53.

Example 4

Preparation of Compound d: 5-(4-methoxybenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8]cyclo-5-yl)oxy)-2-oxoethyl)thio)-3H-imidazo[4,5-C]pyridine-5-ium

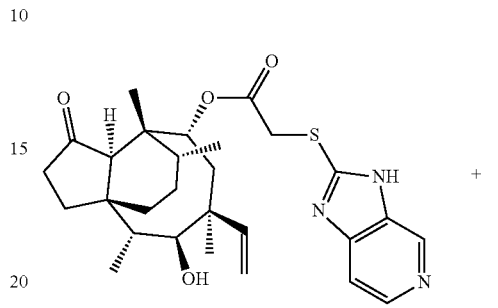

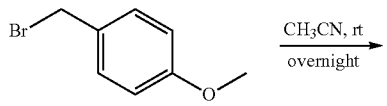

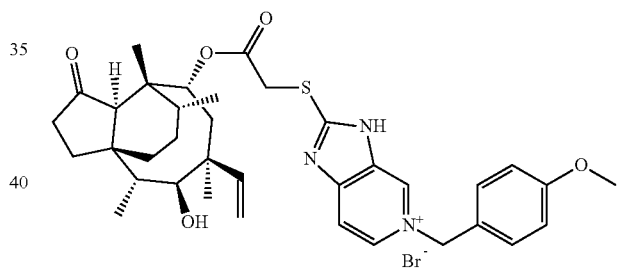

Figure 18:
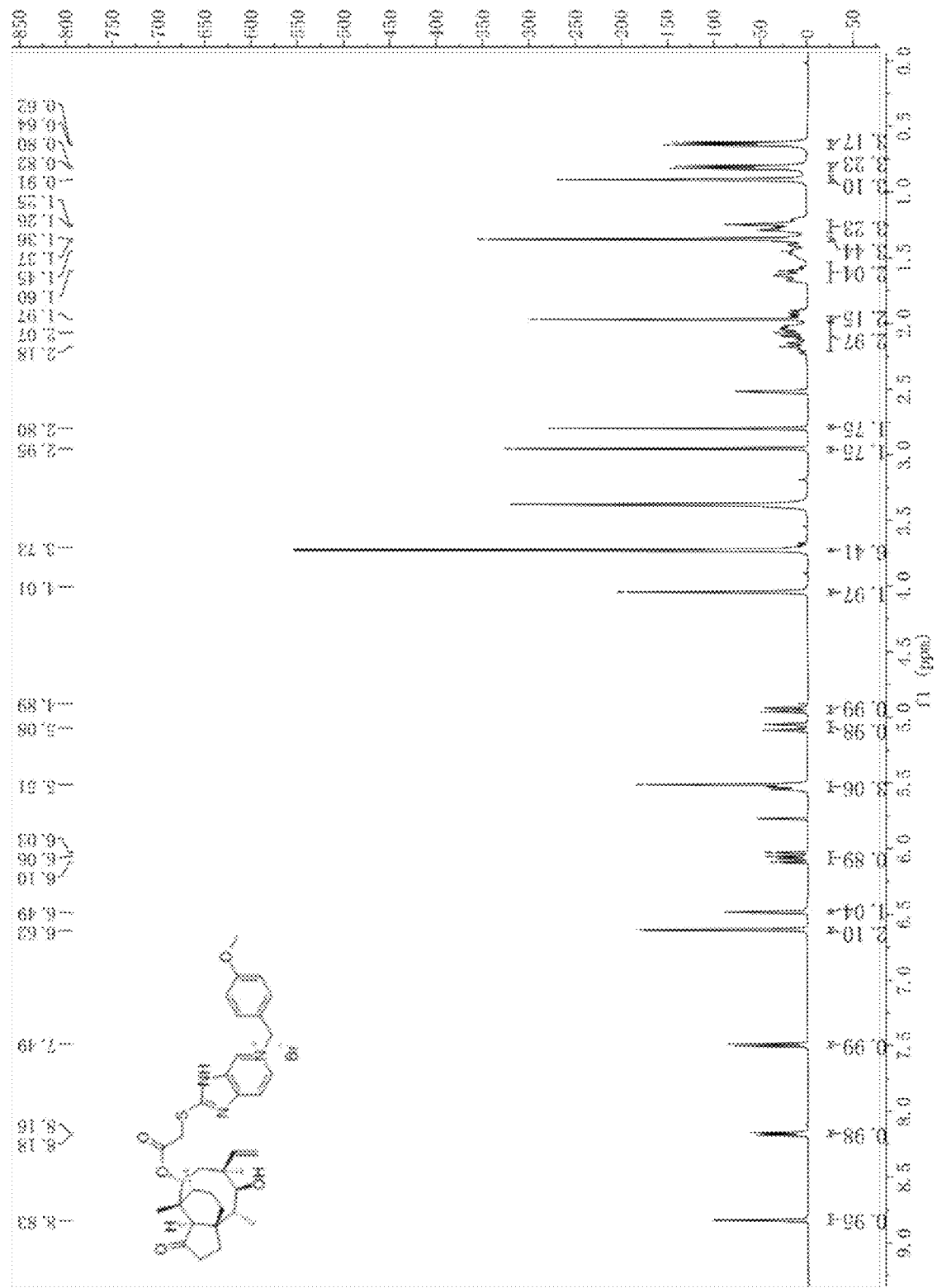
FIG. 18 is a $^1$H NMR spectrum of Compound d of the present invention in deuterated DMSO.
Figure 19:
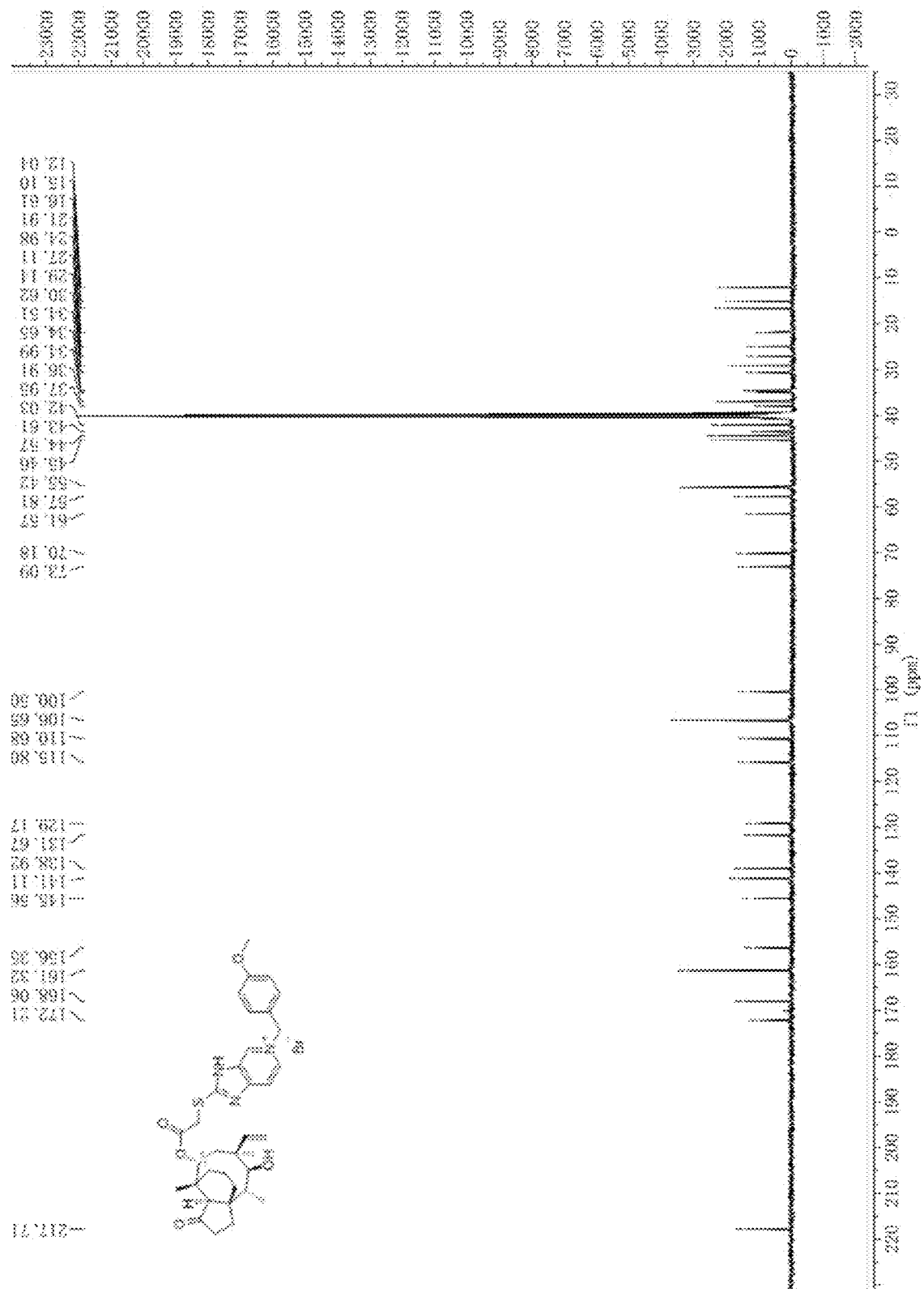
FIG. 19 is a $^{13}$C NMR spectrum of Compound d of the present invention in deuterated DMSO.

The preparation method was as described in Example 1, except that the corresponding raw materials were replaced. Yield of Compound d obtained: 78%. The 1H NMR spectrum of Compound d in deuterated DMSO is as shown in FIG. 18, and the 13C NMR spectrum in deuterated DMSO is as shown in FIG. 19.

$^1$H NMR (600 MHz, DMSO-d6) δ 8.83 (d, J=1.6 Hz, 1H), 8.17 (dd, J=6.8, 1.6 Hz, 1H), 7.50 (d, J=6.7 Hz, 1H), 6.62 (d, J=2.2 Hz, 2H), 6.48 (t, J=2.3 Hz, 1H), 6.07 (dd, J=8.8, 11.2 Hz, 1H), 5.53 (d, J=12.3 Hz, 3H), 5.08 (dd, J=17.8, 1.7 Hz, 1H), 4.94 (dd, J=11.2 Hz, 1H), 4.05 (s, 2H), 3.73 (s, 6H), 2.95 (s, 3H), 2.80 (s, 2H), 2.21-1.97 (d, J=6.6 Hz, 3H), 1.95-1.88 (d, J=6.6 Hz, 2H), 1.65-1.56 (d, J=5.4 Hz, 2H), 1.47 (m, 3H), 1.36 (m, 3H), 0.91 (s, 3H), 0.81 (d, J=6.9 Hz, 3H), 0.63 (d, J=6.8 Hz, 3H).

$^{13}$C NMR (151 MHZ, DMSO-d6) δ 217.71, 172.21, 168.06, 161.32, 156.35, 145.56, 141.11, 138.92, 131.67, 129.17, 115.80, 110.68, 106.65, 100.50, 73.09, 70.18, 61.57, 57.81, 55.42, 45.46, 44.57, 43.61, 42.03, 37.95, 36.91, 34.99, 34.65, 34.51, 30.62, 29.14, 27.11, 24.98, 21.91, 16.61, 15.10, 12.04.

Example 5

Preparation of Compound e: 5-(4-chlorobenzyl)-2-((2-(((3aR,4R,5R,7S,8S,9R,9aS,12R)-8-hydroxy-4,7,9,12-tetramethyl-3-oxo-7-vinyldecahydro-4,9a-propanocyclopenta[8]cyclo-5-yl)oxy)-2-oxoethyl)thio)-3H-imidazo[4,5-C]pyridine-5-ium

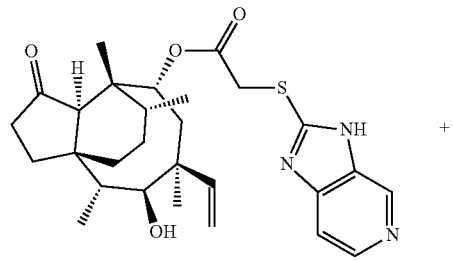

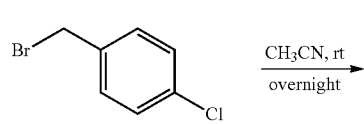

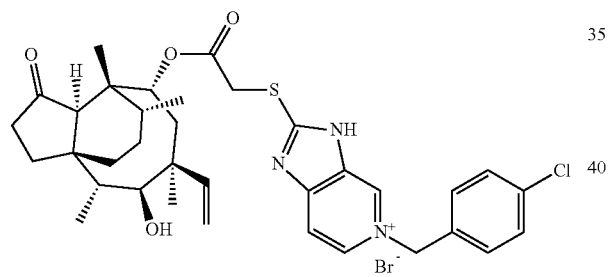

Figure 20:
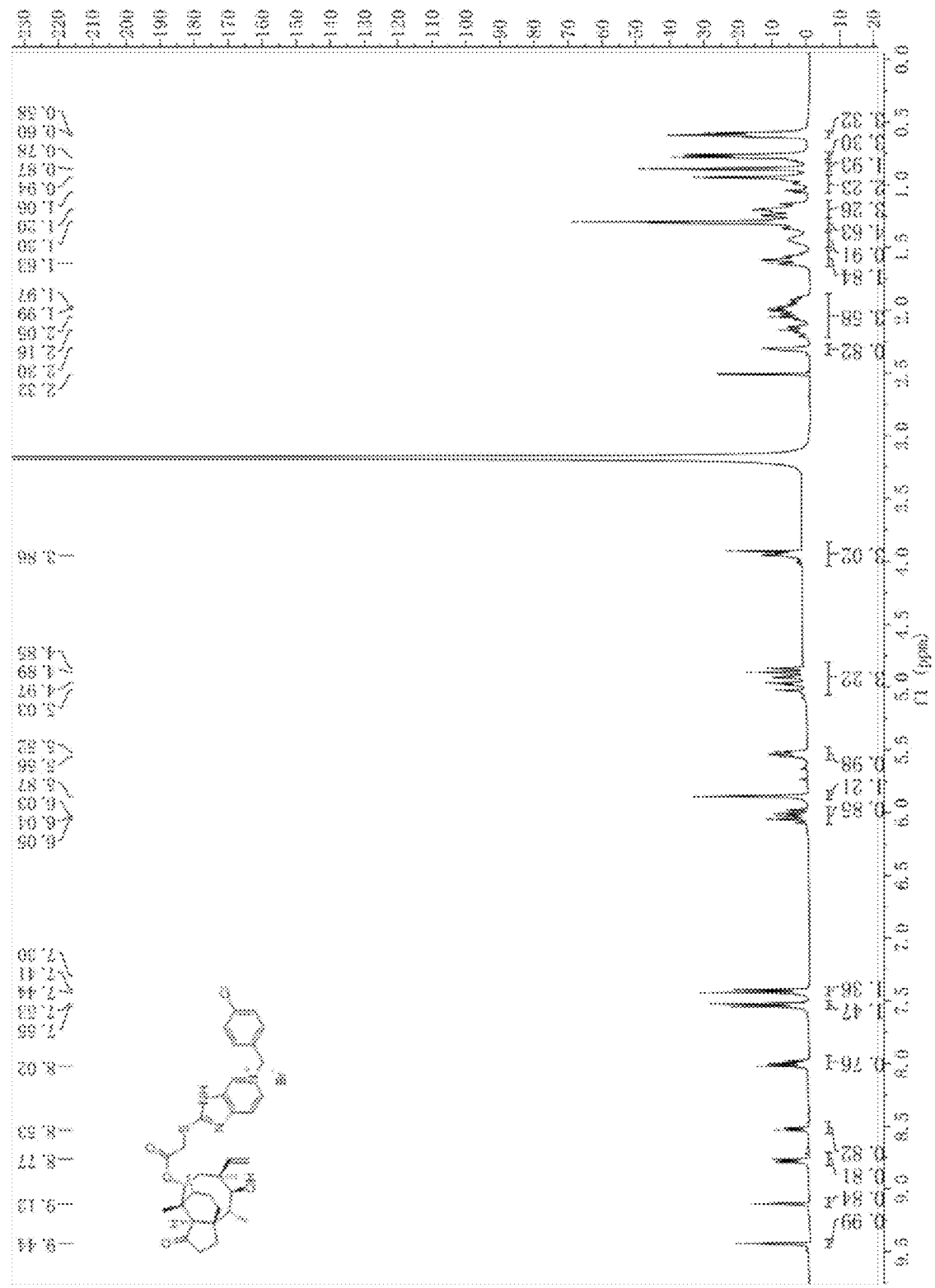
FIG. 20 is a $^1$H NMR spectrum of Compound e of the present invention in deuterated DMSO.
Figure 21:
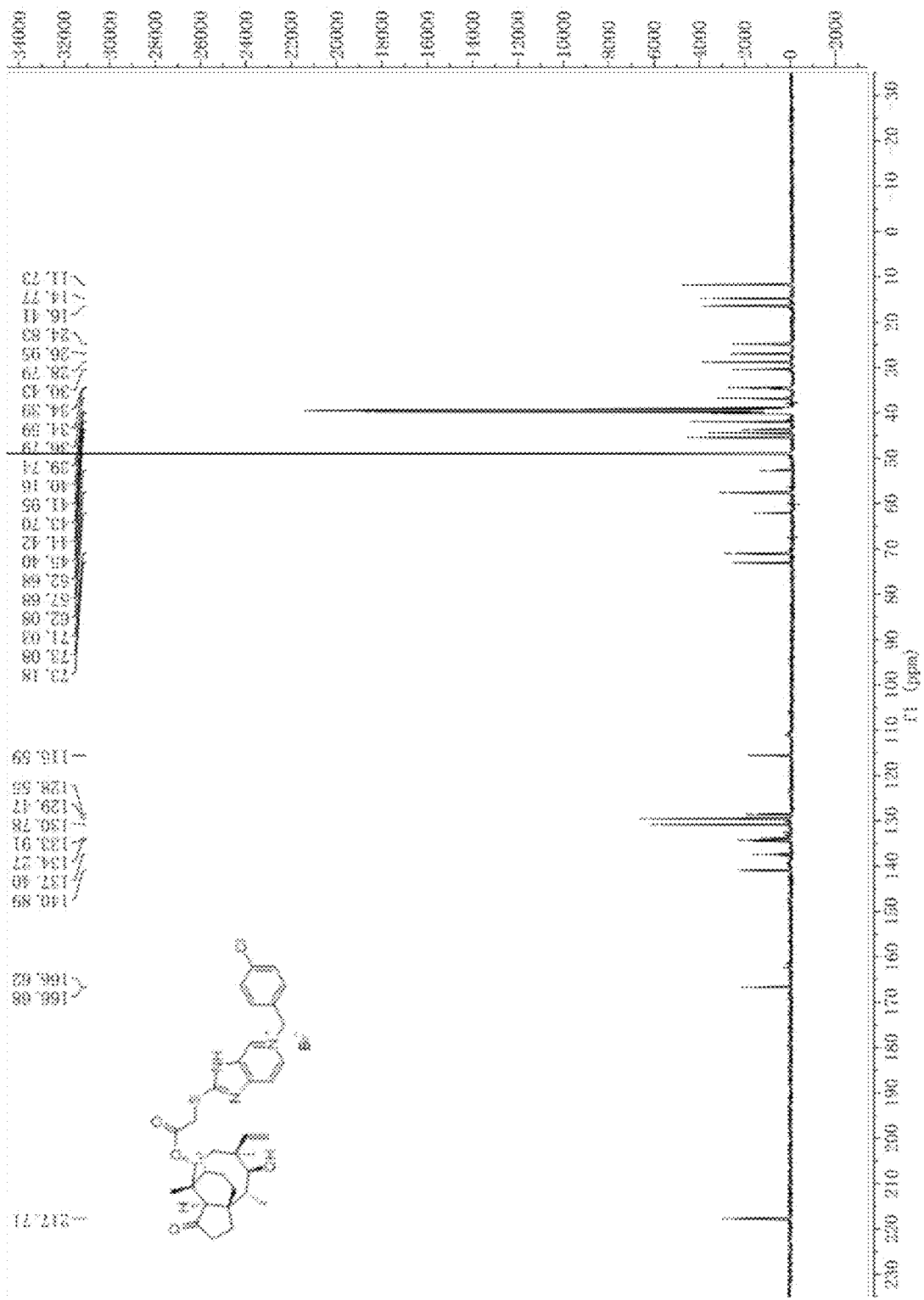
FIG. 21 is a $^{13}$C NMR spectrum of Compound e of the present invention in deuterated DMSO.

The preparation method was as described in Example 1, except that the corresponding raw materials were replaced. Yield of Compound e obtained: 75%. The 1H NMR spectrum of Compound e in deuterated DMSO is as shown in FIG. 20, and the 13C NMR spectrum in deuterated DMSO is as shown in FIG. 21.

$^1$H NMR (600 MHZ, DMSO-d6) δ 9.44 (s, 1H), 9.12 (s, 1H), 8.77 (d, J=1.4 Hz, 1H), 8.52 (d, J=6.5 Hz, 1H), 8.02 (dd, J=11.6 Hz, 1H), 7.56-7.52 (m, 1H), 7.44-7.02 (m, 1H), 6.06-5.96 (dd, J=9.2 Hz, 1H), 5.83 (s, 1H), 5.56-5.46 (d, J=4.2 Hz, 1H), 5.10-4.83 (d, J=6.8 Hz, 3H), 3.86 (s, 3H), 2.32 (s, 1H), 2.24-1.83 (d, J=7.2 Hz, 4H), 1.62-1.52 (d, J=4.2 Hz, 2H), 1.32-1.26 (dd, J=8.2 Hz, 5H), 1.21-1.15 (d, J=8.2 Hz, 3H), 1.12-0.96 (d, J=6.2 Hz, 2H), 0.82-0.76 (d, J=6.6 Hz, 2H), 0.70-0.65 (t, J=6.2 Hz, 3H) 0.60 (t, J=6.3 Hz, 3H).

$^{13}$C NMR (151 MHz, DMSO-d6) δ 217.71, 166.68, 166.62, 140.89, 137.40, 134.27, 133.91, 130.78, 129.47, 128.55, 115.59, 73.18, 73.08, 71.03, 62.08, 57.68, 52.68, 45.40, 44.42, 43.70, 41.95, 40.16, 39.74, 36.79, 34.59, 34.39, 30.43, 28.79, 26.95, 24.83, 16.41, 14.77, 11.73.

Example 6

Preparation of Compound f: 5-(4-nitrobenzyl)-2-((2-(((3aR,4R,5R,7S,8S,9R,9aS,12R)-8-hydroxy-4,7,9,12-tetramethyl-3-oxo-7-vinyldecahydro-4,9a-propanocyclopenta[8]cyclo-5-yl)oxy)-2-oxoethyl)thio)-3H-imidazo[4,5-C]pyridine-5-ium

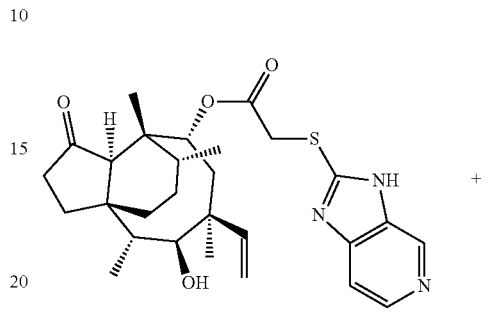

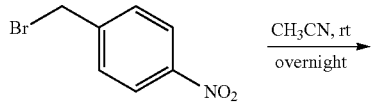

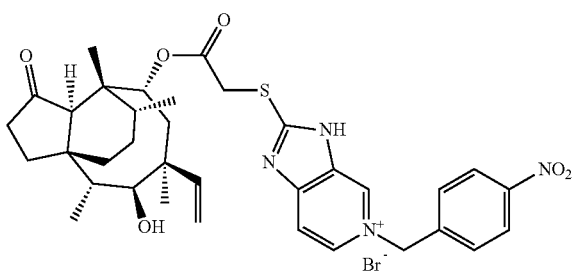

Figure 22:
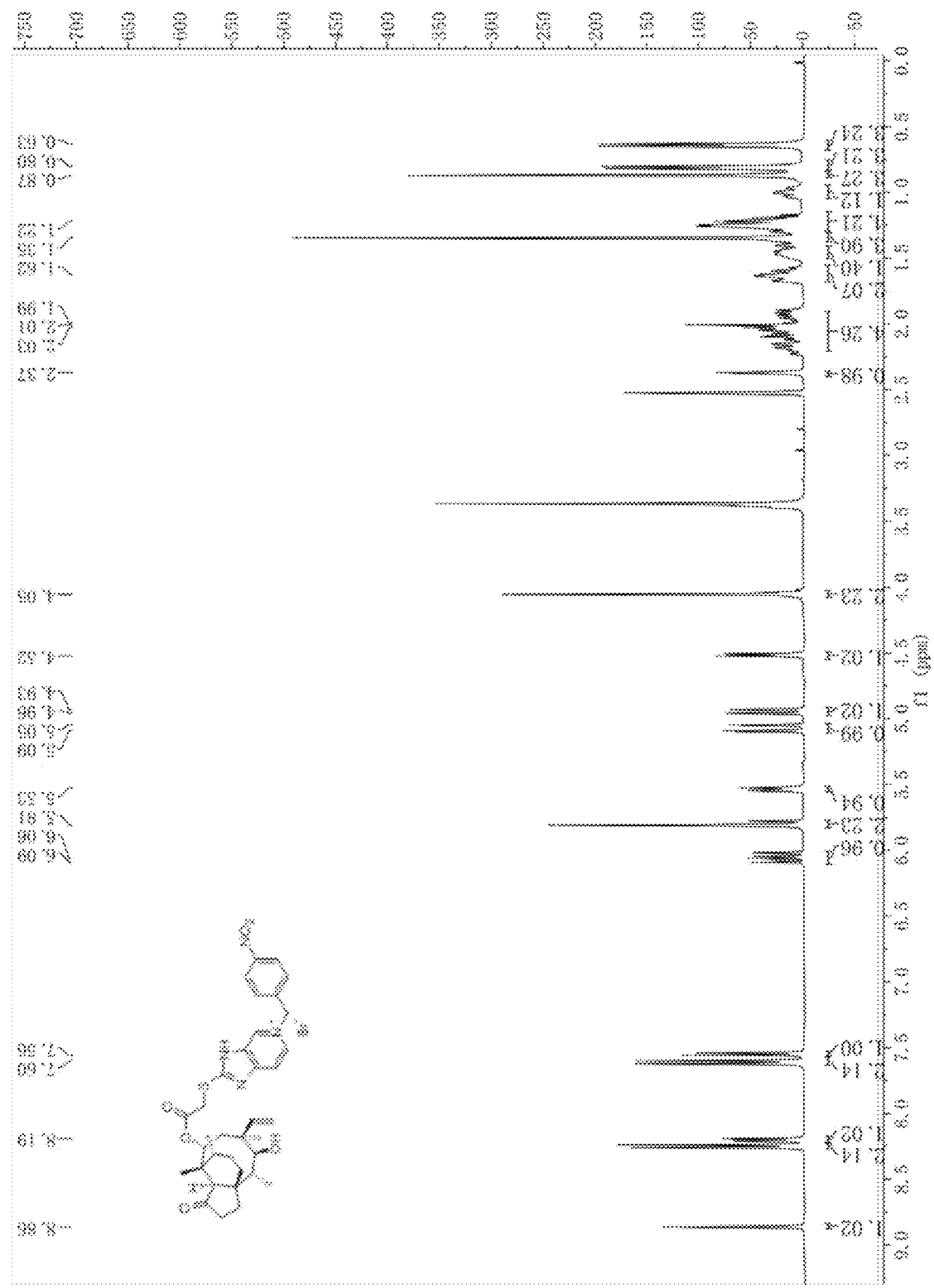
FIG. 22 is a $^1$H NMR spectrum of Compound f of the present invention in deuterated DMSO.
Figure 23:
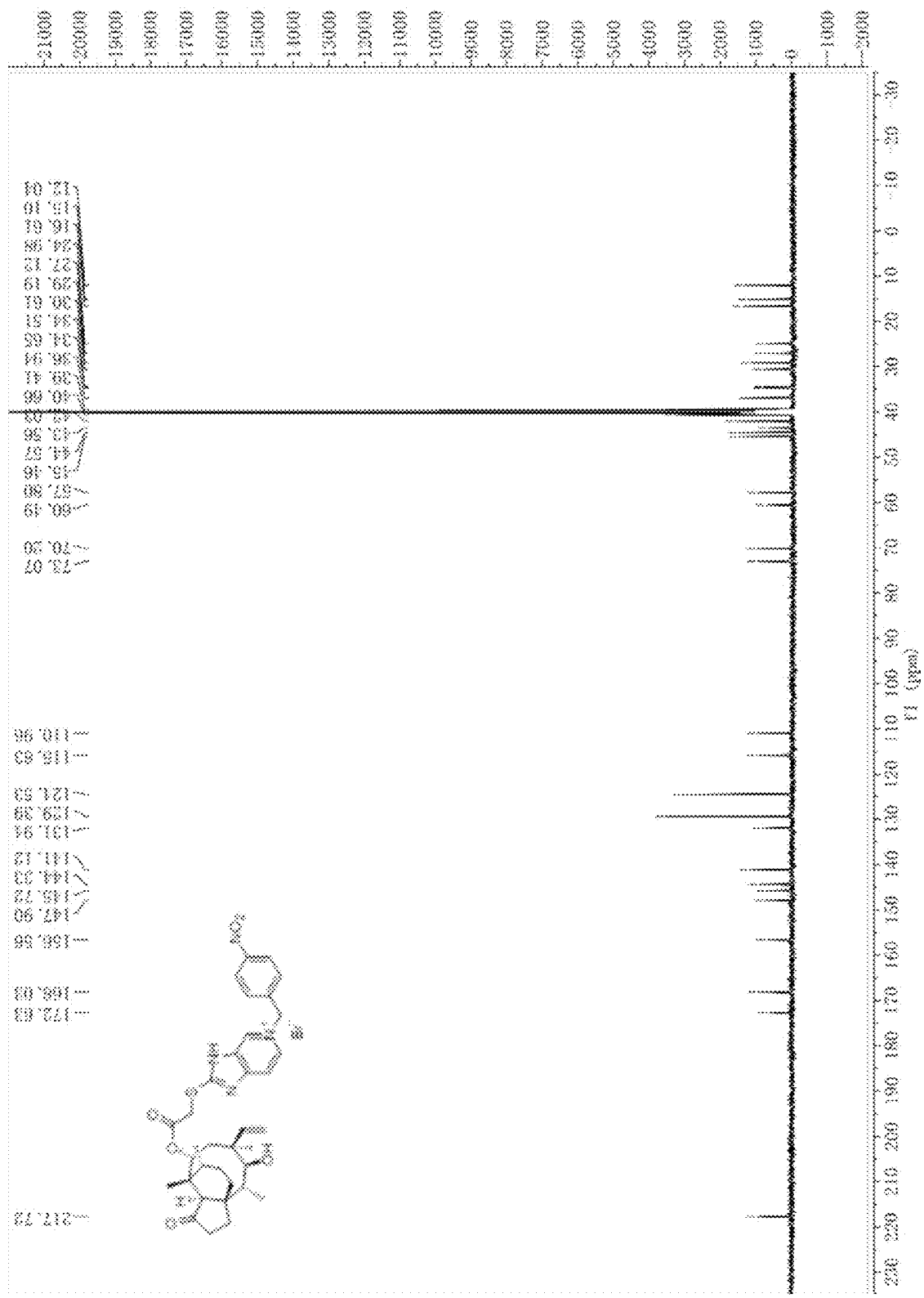
FIG. 23 is a $^{13}$C NMR spectrum of Compound f of the present invention in deuterated DMSO.

The preparation method was as described in Example 1, except that the corresponding raw materials were replaced. Yield of Compound f obtained: 79%. The 1H NMR spectrum of Compound f in deuterated DMSO is as shown in FIG. 22, and the 13C NMR spectrum in deuterated DMSO is as shown in FIG. 23.

$^1$H NMR (600 MHZ, DMSO-d6) δ 8.86 (d, J=1.6 Hz, 1H), 8.27-8.23 (m, 2H), 8.20 (dd, J=6.8, 1.6 Hz, 1H), 7.63-7.57 (m, 2H), 7.55 (d, J=6.7 Hz, 1H), 6.05 (dd, J=17.8, 11.2 Hz, 1H), 5.79 (d, J=12.5 Hz, 2H), 5.54 (d, J=8.2 Hz, 1H), 5.07 (dd, J=17.8, 1.8 Hz, 1H), 4.95 (dd, J=11.2, 1.7 Hz, 1H), 4.51 (d, J=6.0 Hz, 1H), 4.05 (s, 2H), 2.37 (s, 1H), 2.21-1.90 (m, 4H), 1.64-1.56 (m, 2H), 1.52-1.42 (m, 1H), 1.39-1.32 (m, 4H), 1.30-1.15 (m, 4H), 1.00 (td, J=13.8, Hz, 1H), 0.87 (s, 3H), 0.81 (d, J=6.9 Hz, 3H), 0.64 (d, J=6.7 Hz, 3H).

$^{13}$C NMR (151 MHZ, DMSO-d6) δ 217.72, 172.63, 168.03, 156.56, 147.90, 145.72, 144.33, 141.12, 131.94, 129.39, 124.53, 115.83, 110.96, 73.07, 70.20, 60.49, 57.80, 45.46, 44.57, 43.56, 42.03, 40.66, 39.41, 36.94, 34.65, 34.51, 30.61, 29.19, 27.12, 24.98, 16.61, 15.10, 12.04.

Example 7

Preparation of Compound g: 5-(2,4,5-trifluorobenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8]cyclo-5-yl)oxy)-2-oxoethyl)thio)-3H-imidazo[4,5-C]pyridine-5-ium

Example 8

Preparation of Compound h: 5-(4-cyanobenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8]cyclo-5-yl)oxy)-2-oxoethyl)thio)-3H-imidazo[4,5-C]pyridine-5-ium

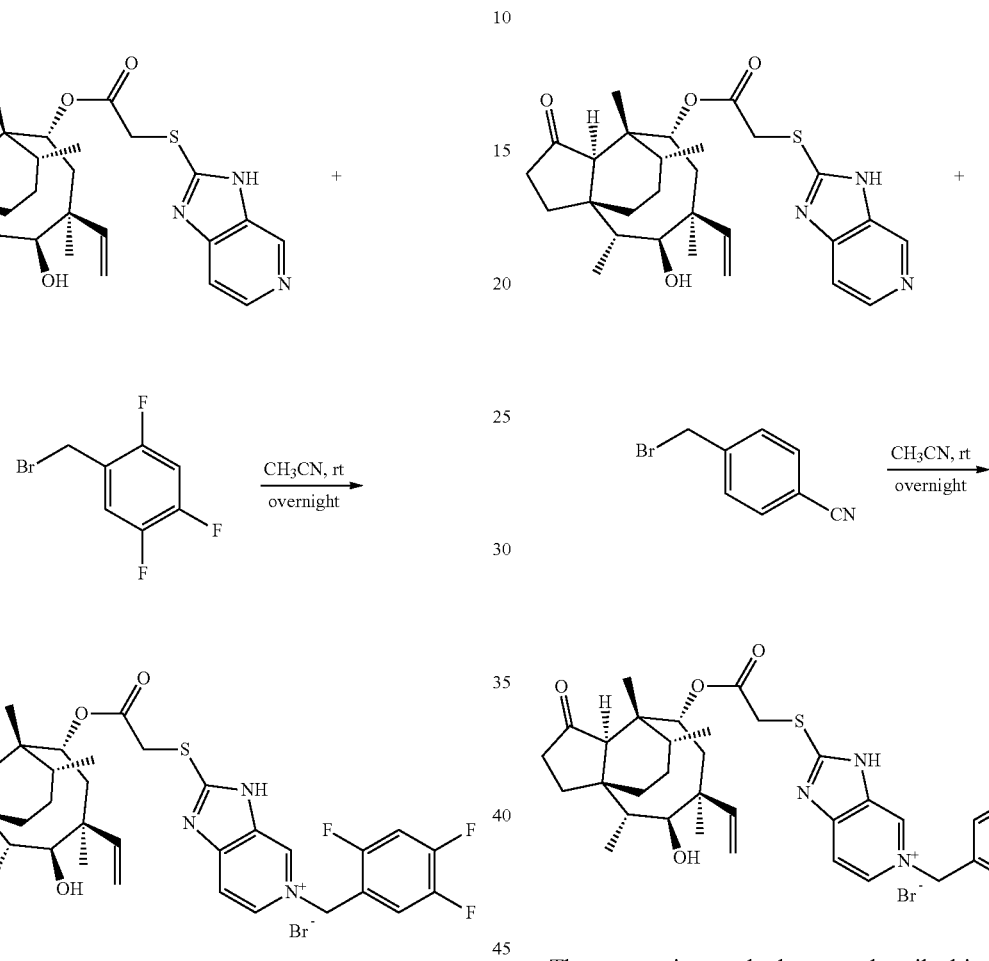

Figure 24:
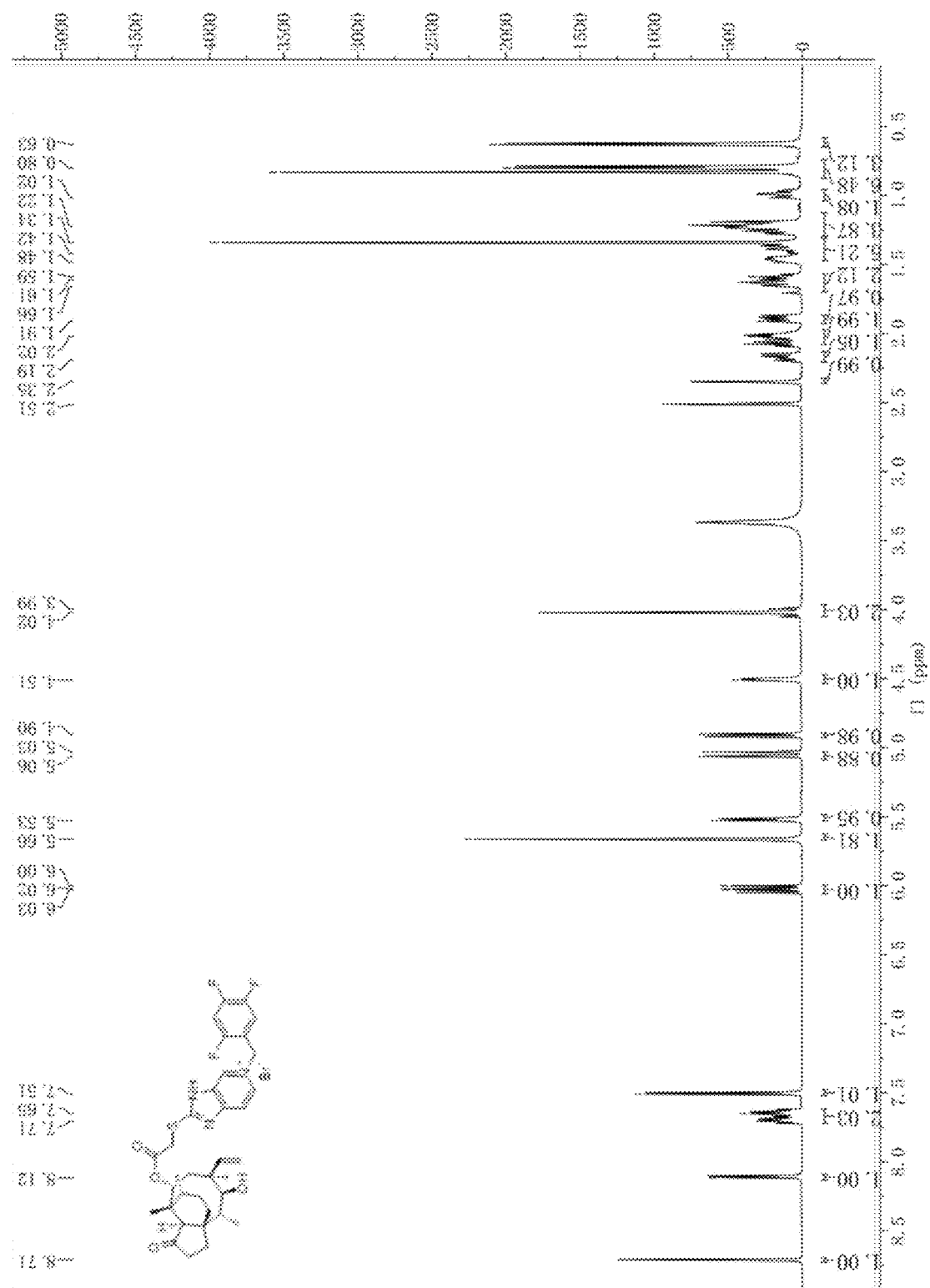
FIG. 24 is a $^1$H NMR spectrum of Compound g of the present invention in deuterated DMSO.
Figure 25:
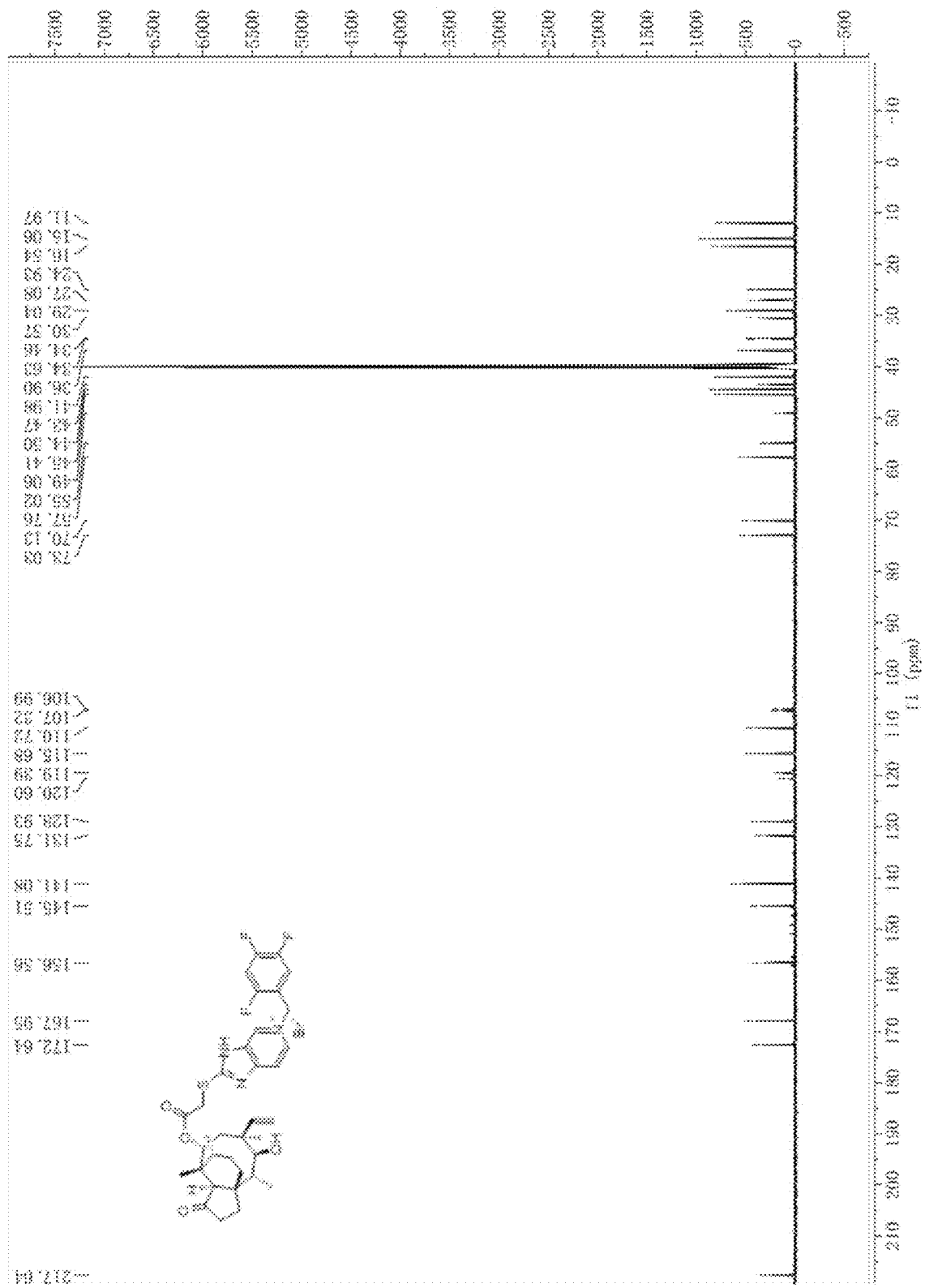
FIG. 25 is a $^{13}$C NMR spectrum of Compound g of the present invention in deuterated DMSO.

The preparation method was as described in Example 1, except that the corresponding raw materials were replaced. Yield of Compound f obtained: 80%. The 1H NMR spectrum of Compound f in deuterated DMSO is as shown in FIG. 24, and the 13C NMR spectrum in deuterated DMSO is as shown in FIG. 25.

$^1$H NMR (600 MHz, DMSO-d6) δ 8.71 (d, J=1.6 Hz, 1H), 8.11 (dd, J=6.8, 1.6 Hz, 1H), 7.72-7.62 (m, 2H), 7.51 (d, J=6.8 Hz, 1H), 6.03 (dd, J=17.8, 11.3 Hz, 1H), 5.66 (s, 2H), 5.52 (d, J=8.4 Hz, 1H), 5.09-5.03 (m, 1H), 4.91 (dd, J=11.2, 1.7 Hz, 1H), 4.51 (d, J=5.9 Hz, 1H), 4.02 (d, J=2.3 Hz, 1H), 2.35 (d, J=2.7 Hz, 1H), 2.21-2.13 (m, 1H), 2.08-1.97 (m, 2H), 1.89 (dd, J=15.8, 8.4 Hz, 1H), 1.70-1.57 (m, 2H), 1.47-1.31 (m, 5H), 1.30-1.12 (m, 4H), 0.99 (td, J=14.1, 4.4 Hz, 1H), 0.88-0.74 (m, 6H), 0.63 (d, J=7.0 Hz, 3H).

$^{13}$C NMR (151 MHz, DMSO-d6) δ 217.64, 172.64, 167.95, 156.56, 145.51, 141.08, 131.75, 128.93, 120.60, 119.39, 115.68, 110.72, 107.32, 106.99, 73.03, 70.13, 57.76, 55.02, 49.06, 45.41, 44.50, 43.47, 41.98, 36.90, 34.63, 34.46, 30.57, 29.04, 27.08, 24.93, 16.54, 15.06, 11.97.

Figure 26:
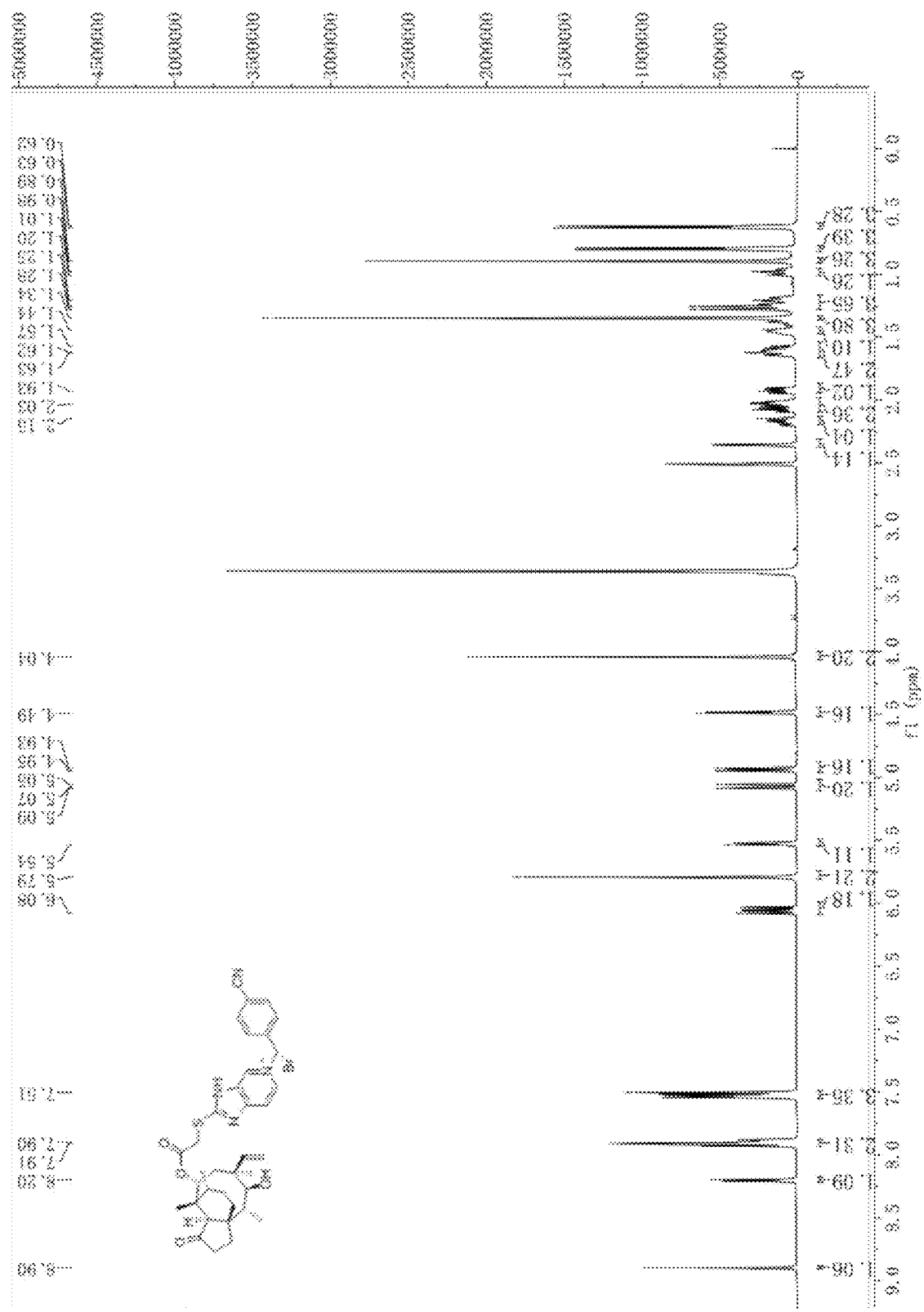
FIG. 26 is a $^1$H NMR spectrum of Compound h of the present invention in deuterated DMSO.
Figure 27:
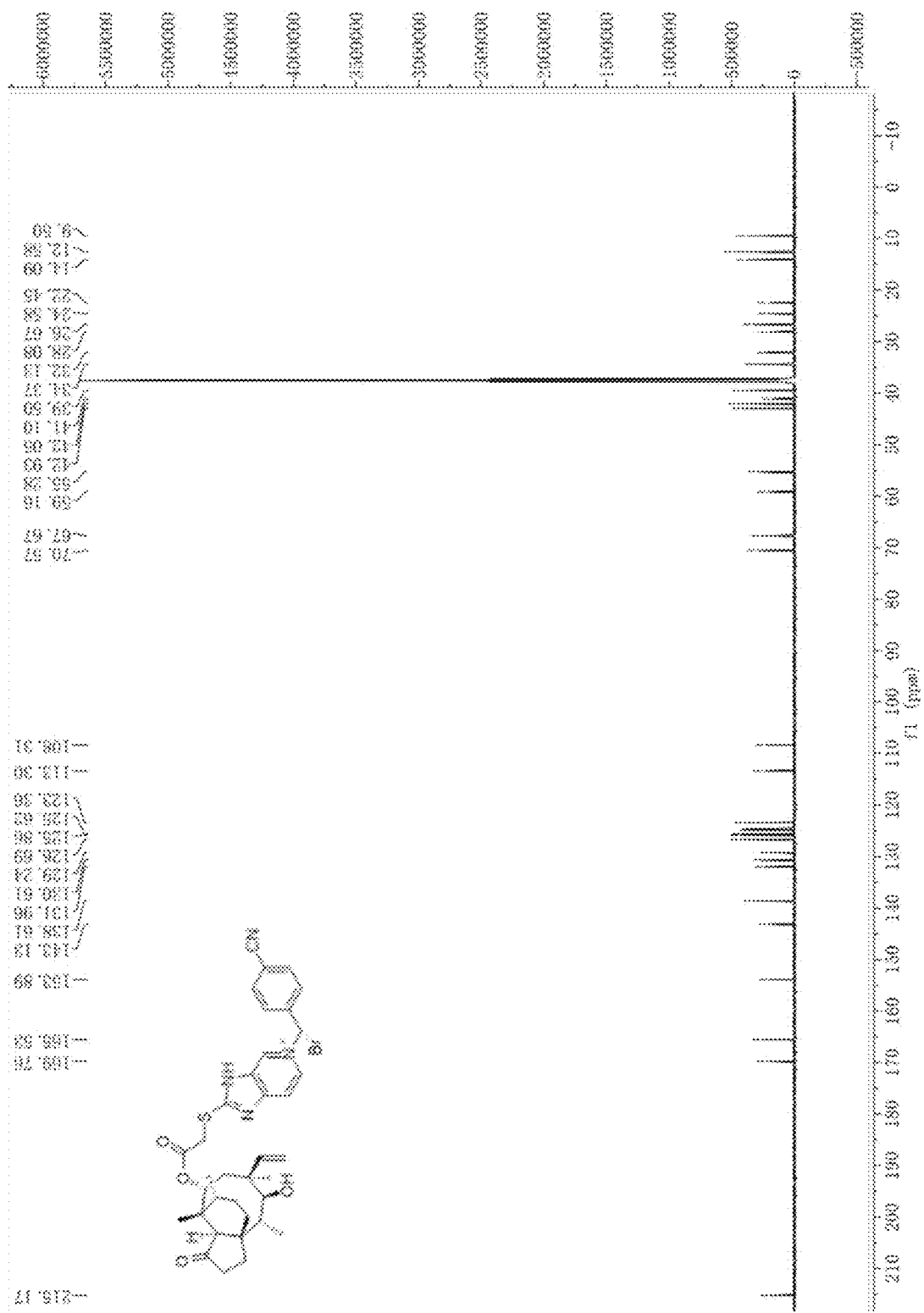
FIG. 27 is a $^{13}$C NMR spectrum of Compound h of the present invention in deuterated DMSO.

The preparation method was as described in Example 1, except that the corresponding raw materials were replaced. Yield of Compound h obtained: 81%. The 1H NMR spectrum of Compound h in deuterated DMSO is as shown in FIG. 26, and the 13C NMR spectrum in deuterated DMSO is as shown in FIG. 27.

$^1$H NMR (600 MHZ, DMSO-d6) δ 8.90 (d, J=1.6 Hz, 1H), 8.20 (dd, J=6.8, 1.6 Hz, 1H), 7.94-7.86 (m, 2H), 7.56-7.49 (m, 3H), 6.06 (dd, J=17.8, 11.2 Hz, 1H), 5.79 (s, 2H), 5.53 (d, J=8.4 Hz, 1H), 5.07 (dd, J=17.8, 1.7 Hz, 1H), 4.94 (dd, J=11.3, 1.7 Hz, 1H), 4.48 (d, J=6.1 Hz, 1H), 4.04 (s, 2H), 2.35 (d, J=2.6 Hz, 1H), 2.19-2.13 (m, 1H), 2.09-1.98 (m, 2H), 1.94-1.86 (m, 1H), 1.64-1.54 (m, 2H), 1.47-1.40 (m, 1H), 1.34 (s, 4H), 1.28-1.14 (m, 4H), 0.98 (td, J=14.0, 4.4 Hz, 1H), 0.89 (s, 3H), 0.80 (d, J=7.0 Hz, 3H), 0.62 (d, J=7.0 Hz, 3H).

$^{13}$C NMR (151 MHZ, DMSO-d6) δ 215.17, 169.76, 165.53, 153.89, 143.13, 138.61, 131.96, 130.61, 129.24, 126.69, 125.86, 125.62, 123.36, 113.30, 108.31, 70.57, 67.67, 59.16, 55.28, 42.93, 42.05, 41.10, 39.50, 34.37, 32.13, 28.08, 26.67, 24.58, 22.45, 14.09, 12.58, 9.50.

Example 9

Preparation of Compound i: 5-(4-methylbenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8]cyclo-5-yl)oxy)-2-oxoethyl)thio)-3H-imidazo[4,5-C]pyridine-5-ium

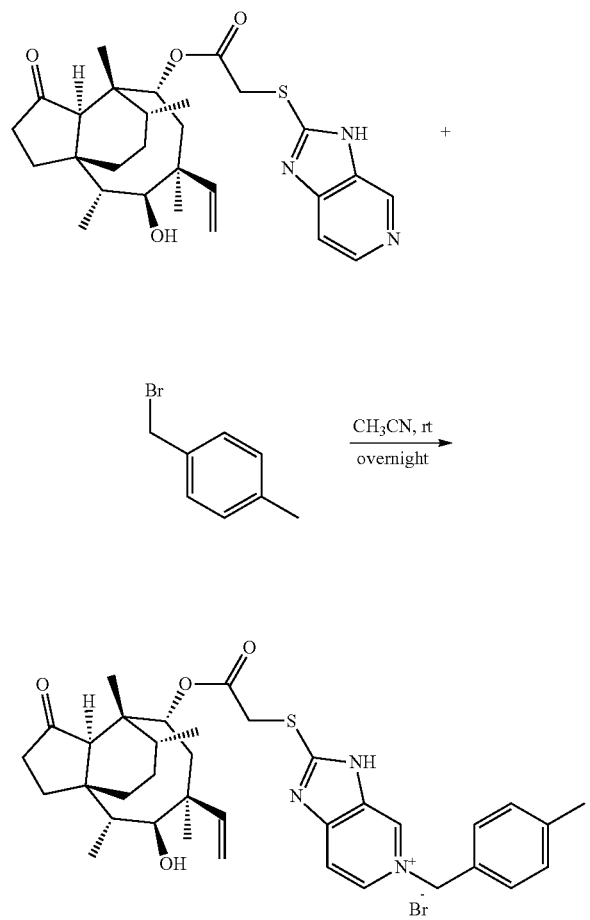

Figure 28:
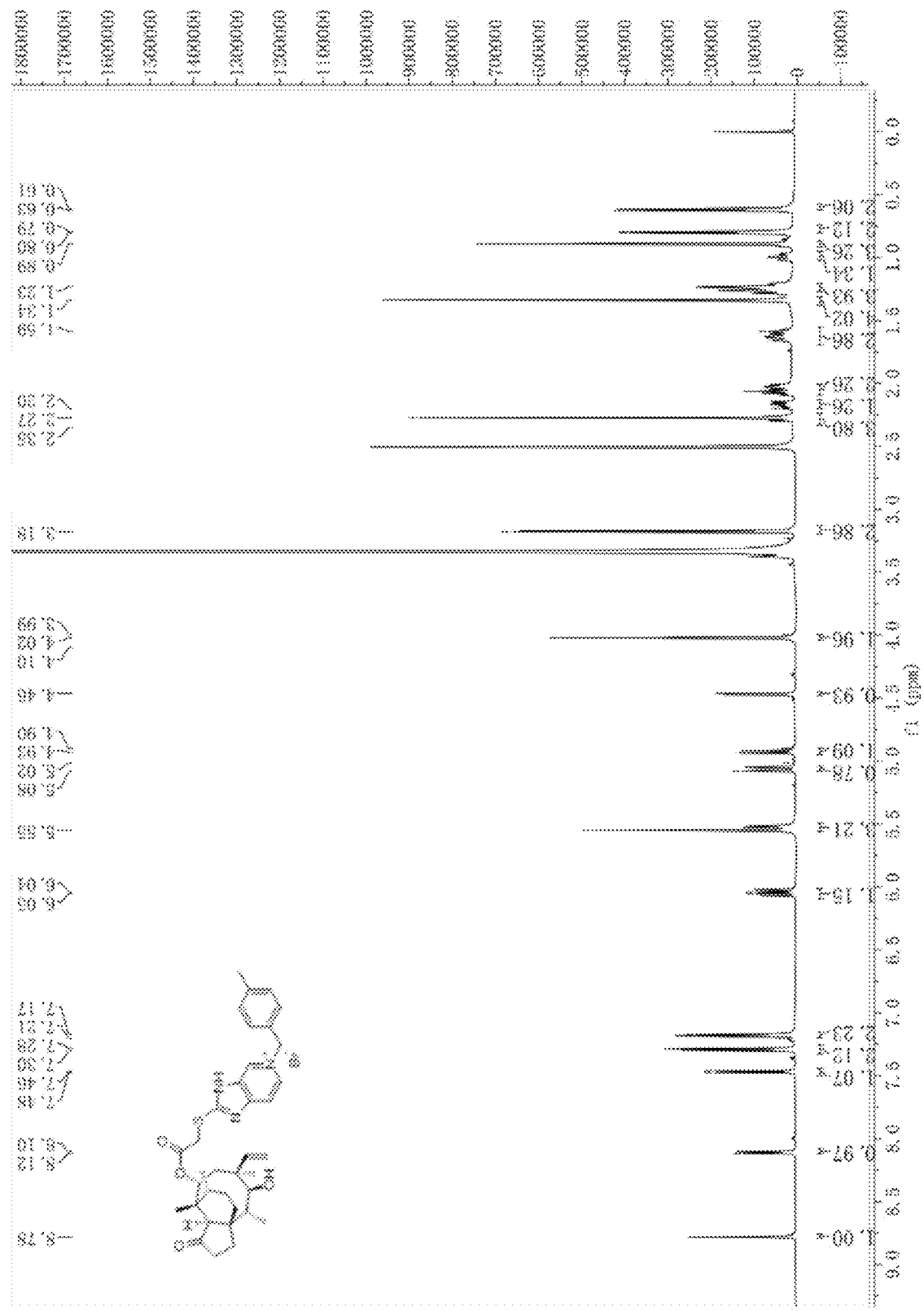
FIG. 28 is a $^1$H NMR spectrum of Compound i of the present invention in deuterated DMSO.
Figure 29:
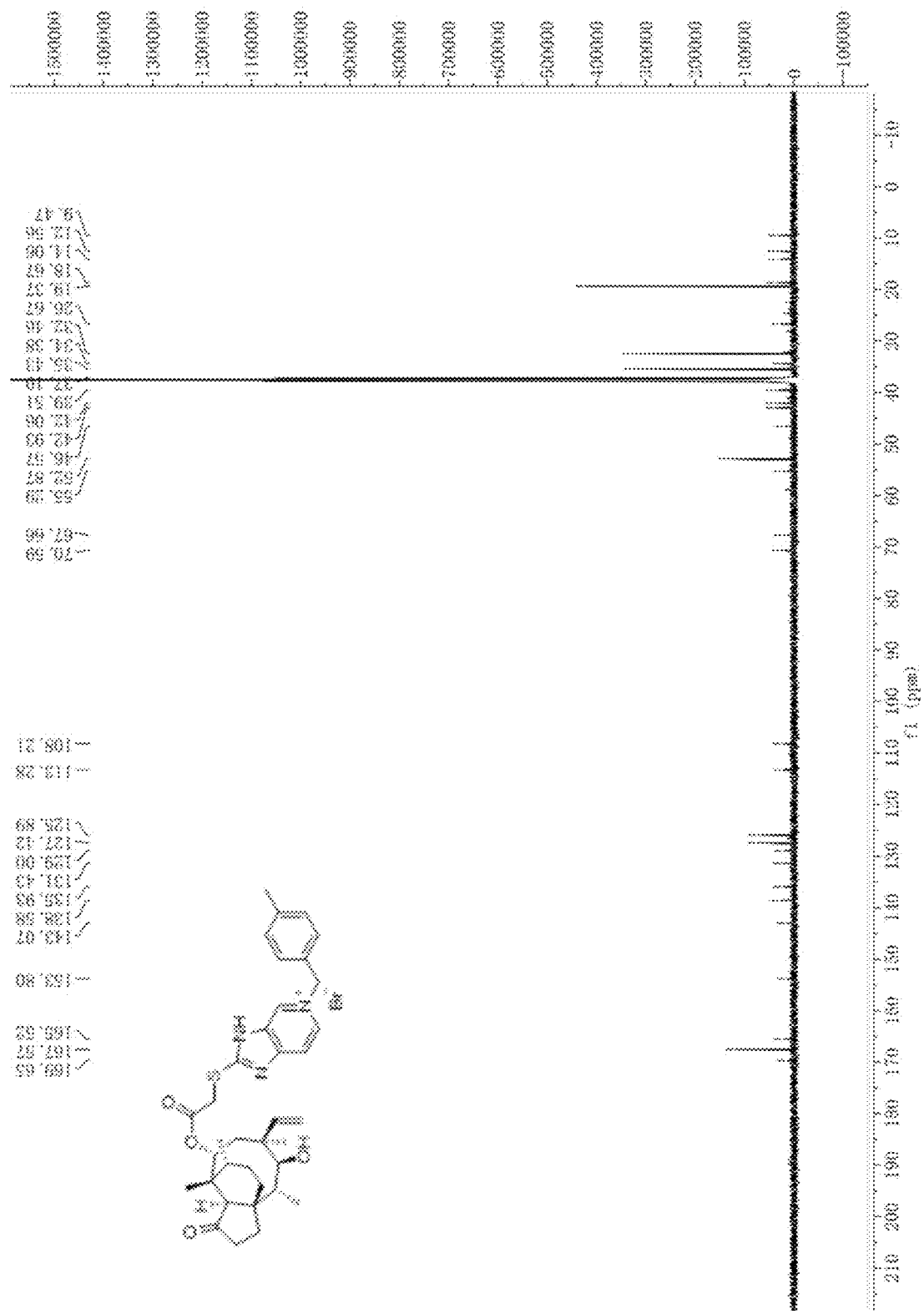
FIG. 29 is a $^{13}$C NMR spectrum of Compound i of the present invention in deuterated DMSO.

The preparation method was as described in Example 1, except that the corresponding raw materials were replaced. Yield of Compound i obtained: 87%. The 1H NMR spectrum of Compound i in deuterated DMSO is as shown in FIG. 28, and the 13C NMR spectrum in deuterated DMSO is as shown in FIG. 29.

$^1$H NMR (600 MHZ, DMSO-d6) δ 8.78 (d, J=1.5 Hz, 1H), 8.11 (dd, J=6.7, 1.6 Hz, 1H), 7.47 (d, J=6.7 Hz, 1H), 7.33-7.26 (m, 2H), 7.18 (d, J=7.9 Hz, 2H), 6.09-6.01 (m, 1H), 5.56-5.50 (m, 3H), 4.92 (dd, J=11.2, 1.7 Hz, 1H), 4.47 (d, J=6.0 Hz, 1H), 4.10 (d, J=5.3 Hz, 1H), 4.02 (s, 2H), 3.17 (d, J=5.2 Hz, 3H), 2.44-2.31 (d, J=8.2 Hz, 3H), 2.21-2.18 (d, J=4.2 Hz, 1H), 2.16-2.09 (d, J=6.2 Hz, 2H), 1.62-1.56 (m, 3H), 1.46-1.34 (m, 4H), 1.34 (s, 4H), 1.27-1.20 (m, 1H), 0.89 (s, 3H), 0.79 (s, 2H), 0.61 (s, 2H).

$^{13}$C NMR (151 MHZ, DMSO-d6) δ 169.65, 167.57, 165.52, 153.80, 143.07, 138.58, 135.93, 131.43, 129.00, 127.42, 125.89, 113.28, 108.21, 70.59, 67.66, 55.29, 52.87, 46.57, 42.93, 42.06, 39.51, 37.10, 35.43, 34.38, 32.46, 26.67, 19.37, 18.67, 14.06, 12.56, 9.47.

Example 10

Preparation of Compound j: 5-([1,1'-biphenyl]-4-ylmethyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8]cyclo-5-yl)oxy)-2-oxoethyl)thio)-3H-imidazo[4,5-C]pyridine-5-ium

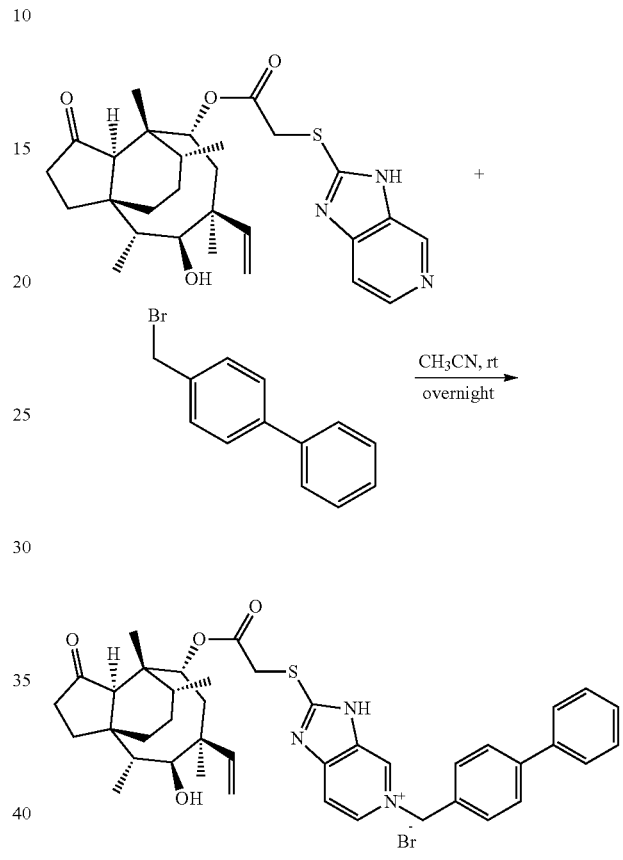

Figure 30:
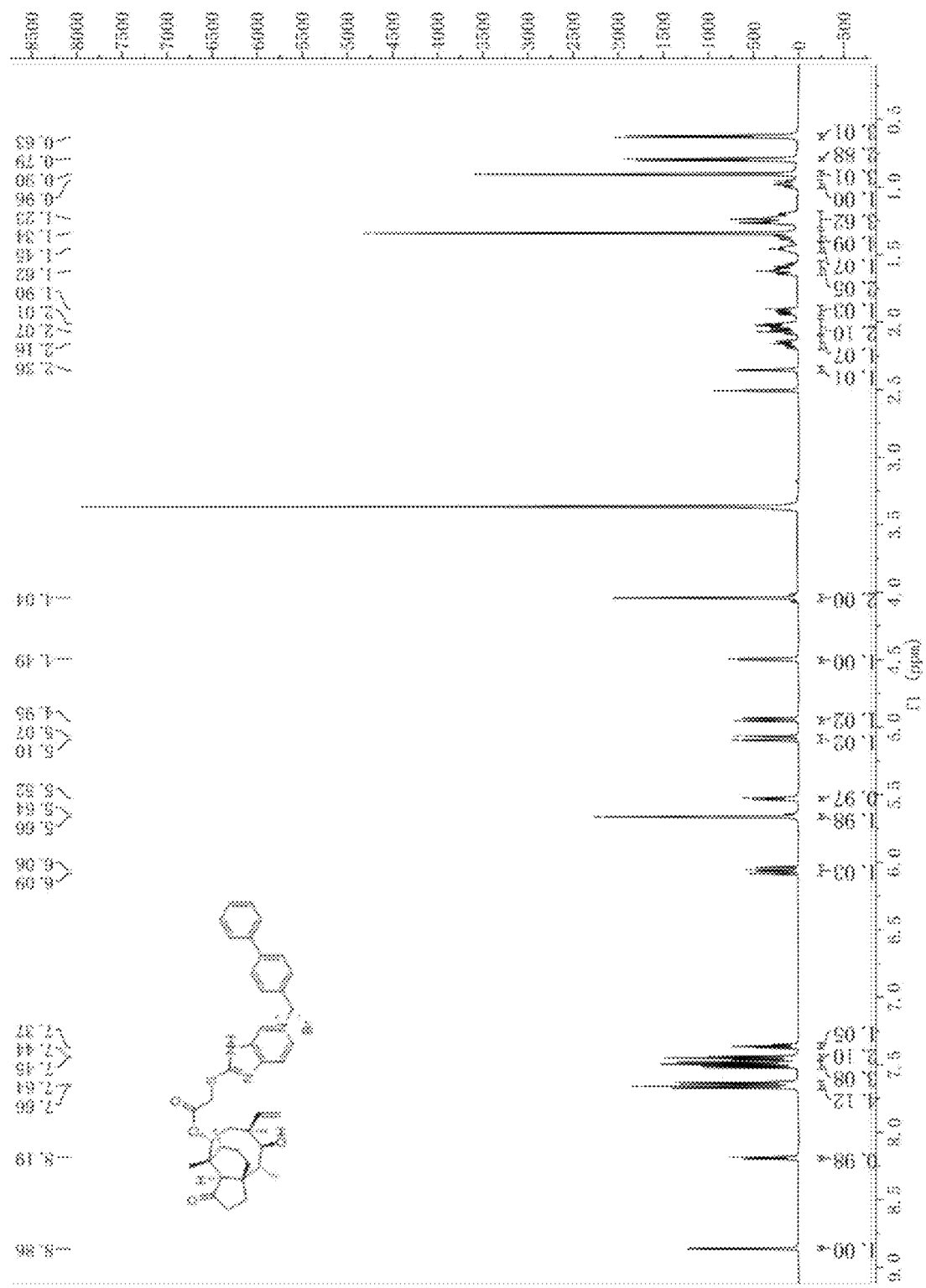
FIG. 30 is a $^1$H NMR spectrum of Compound j of the present invention in deuterated DMSO.
Figure 31:
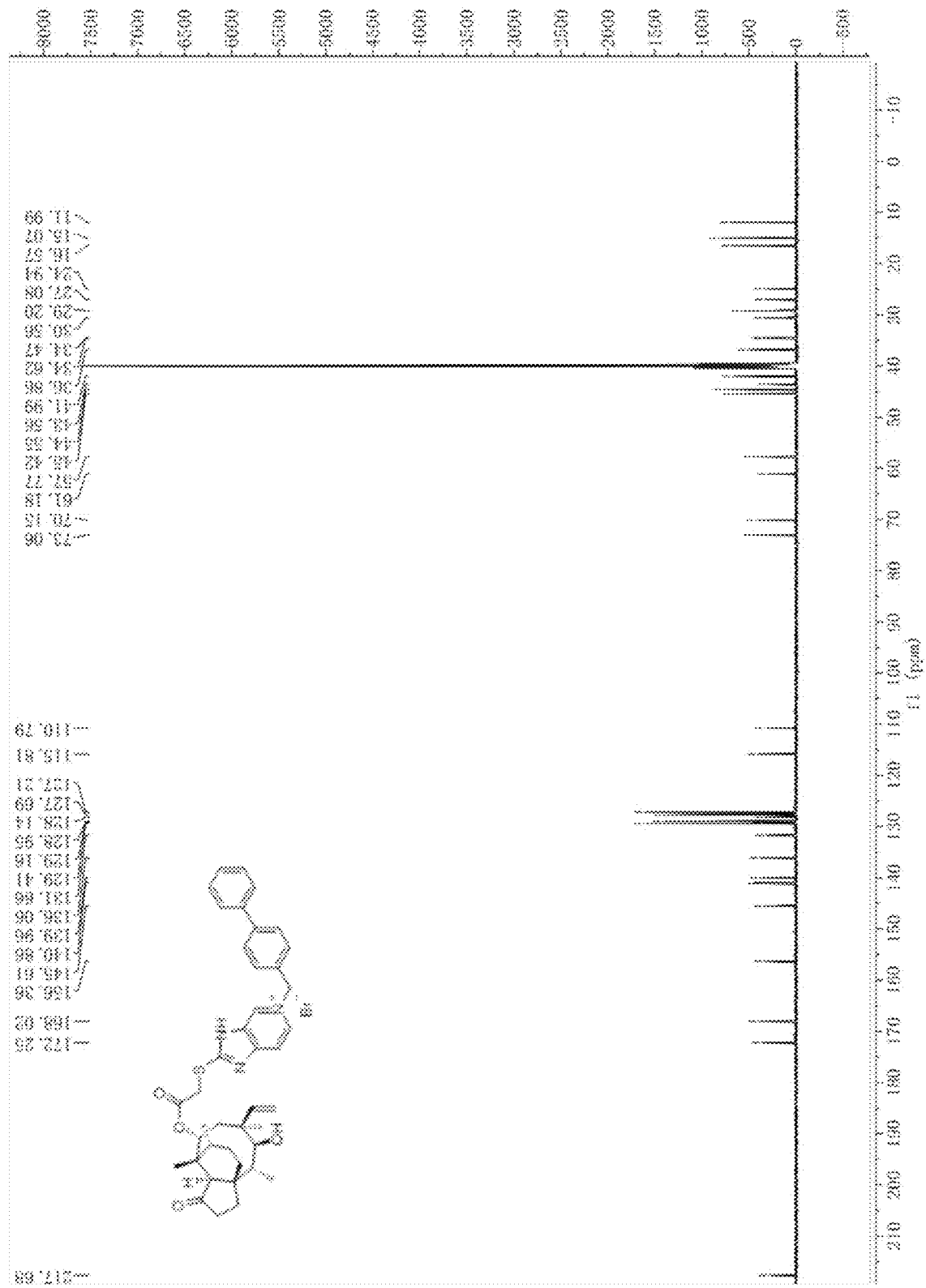
FIG. 31 is a $^{13}$C NMR spectrum of Compound j of the present invention in deuterated DMSO.
Figure 32:
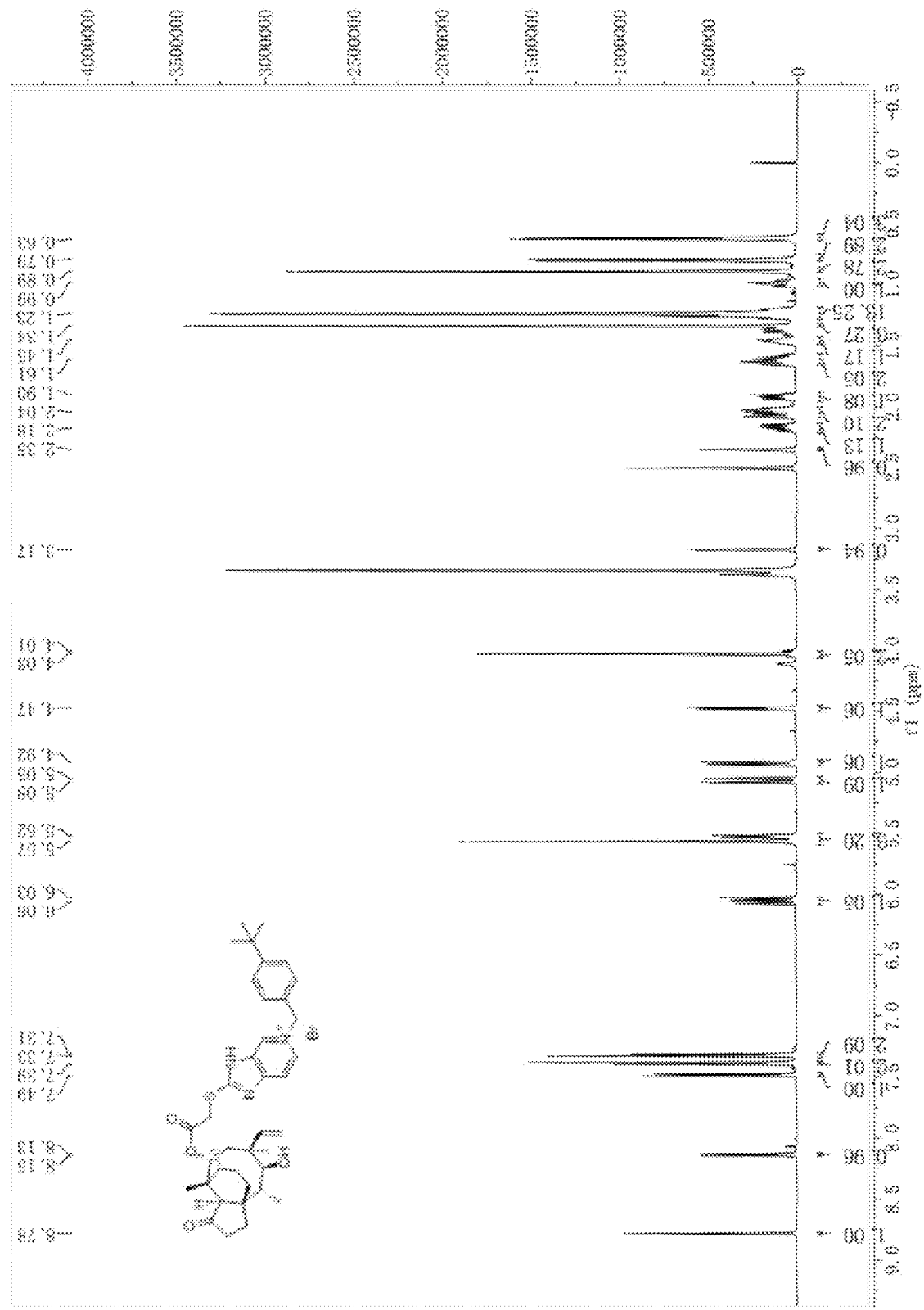
FIG. 32 is a $^1$H NMR spectrum of Compound k of the present invention in deuterated DMSO.
Figure 33:
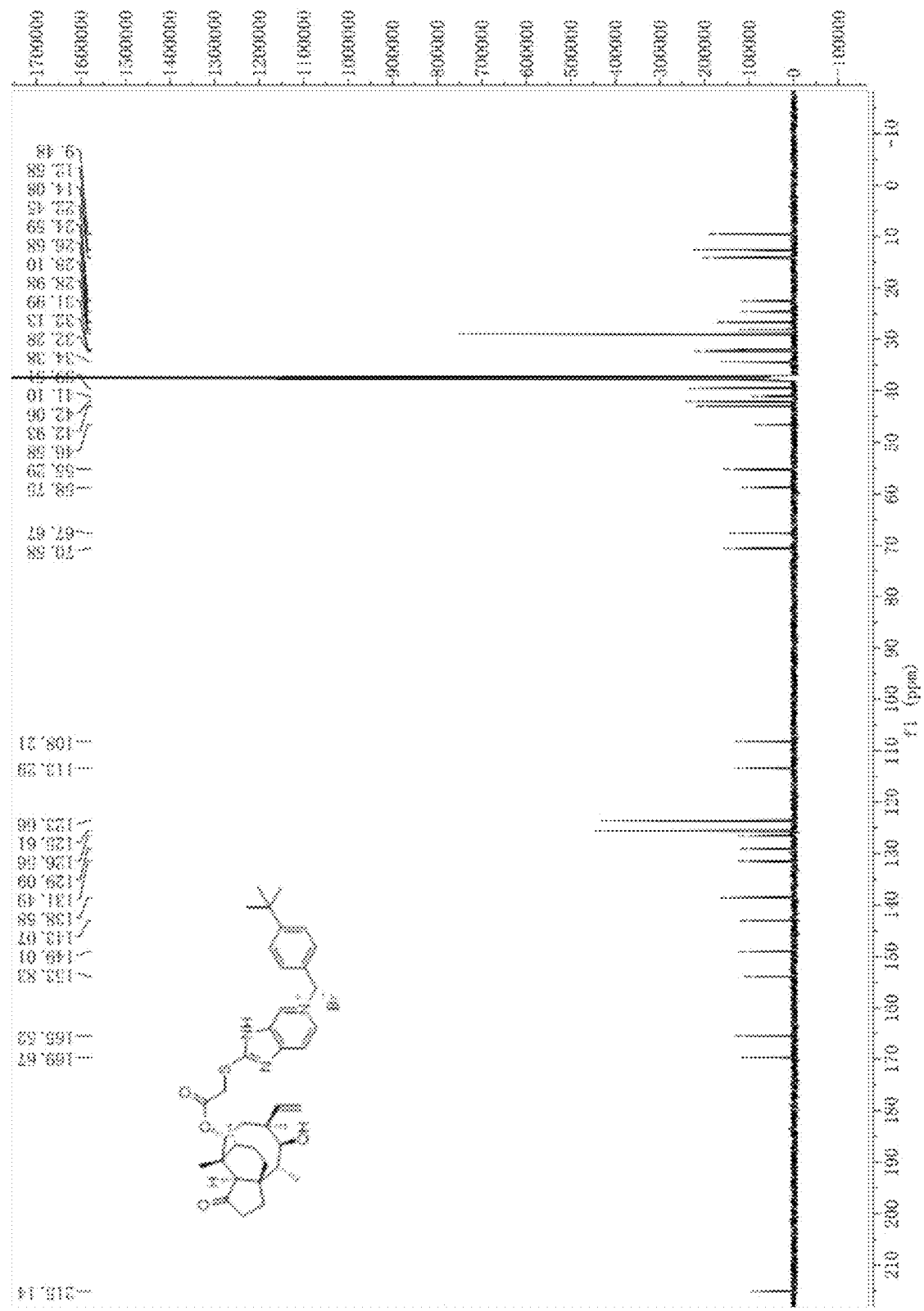
FIG. 33 is a $^{13}$C NMR spectrum of Compound k of the present invention in deuterated DMSO.

The preparation method was as described in Example 1, except that the corresponding raw materials were replaced. Yield of Compound j obtained: 85%. The 1H NMR spectrum of Compound j in deuterated DMSO is as shown in FIG. 30, and the 13C NMR spectrum in deuterated DMSO is as shown in FIG. 31.

$^1$H NMR (600 MHZ, DMSO-d6) δ 8.86 (d, J=1.5 Hz, 1H), 8.19 (dd, J=6.8, 1.6 Hz, 1H), 7.68-7.62 (m, 4H), 7.53-7.47 (m, 3H), 7.45 (t, J=7.7 Hz, 2H), 7.38-7.34 (m, 1H), 6.06 (dd, J=17.8, 11.2 Hz, 1H), 5.66 (s, 2H), 5.53 (d, J=8.4 Hz, 1H), 5.08 (dd, J=17.8, 1.7 Hz, 1H), 4.94 (dd, J=11.2, 1.7 Hz, 1H), 4.50 (d, J=6.0 Hz, 1H), 4.04 (d, J=1.4 Hz, 2H), 2.36 (d, J=2.7 Hz, 1H), 2.20-2.10 (m, 1H), 2.09-1.98 (m, 2H), 1.92 (dd, J=15.8, 8.4 Hz, 1H), 1.65-1.55 (m, 2H), 1.46 (dd, J=3.2 Hz, 1H), 1.34 (s, 4H), 1.30-1.18 (m, 4H), 0.98 (td, J=14.0, 4.4 Hz, 1H), 0.90 (s, 3H), 0.80 (d, J=7.0 Hz, 3H), 0.63 (d, J=7.0 Hz, 3H).

$^{13}$C NMR (151 MHZ, DMSO-d6) δ 217.68, 172.25, 168.02, 156.36, 145.61, 140.86, 139.96, 136.06, 131.66, 129.41, 129.16, 128.95, 128.14, 127.69, 127.21, 115.81, 110.79, 73.06, 70.15, 61.18, 57.77, 45.42, 44.55, 43.56, 41.99, 36.86, 34.62, 34.47, 30.56, 29.20, 27.08, 24.94, 16.57, 15.07, 11.99.

Example 11

Preparation of Compound k: 5-(4-(tert-butyl)benzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8]cyclo-5-yl)oxy)-2-oxoethyl)thio)-3H-imidazo[4,5-C]pyridine-5-ium

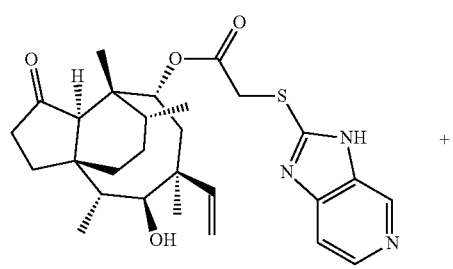

+

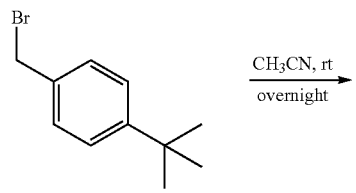

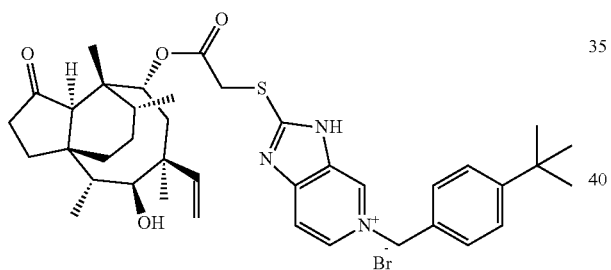

The preparation method was as described in Example 1, except that the corresponding raw materials were replaced. Yield of Compound k obtained: 84%. The 1H NMR spectrum of Compound k in deuterated DMSO is as shown in FIG. 21, and the 13C NMR spectrum in deuterated DMSO is as shown in FIG. 22.

$^1$H NMR (600 MHZ, DMSO-d6) δ 8.78 (d, J=1.6 Hz, 1H), 8.14 (dd, J=6.8, 1.6 Hz, 1H), 7.48 (d, J=6.7 Hz, 1H), 7.40-7.37 (m, 2H), 7.34-7.30 (m, 2H), 6.05 (dd, J=17.8, 11.2 Hz, 1H), 5.59-5.50 (m, 3H), 5.07 (dd, J=17.8, 1.7 Hz, 1H), 4.93 (dd, J=11.2, 1.7 Hz, 1H), 4.48 (d, J=6.0 Hz, 1H), 4.03 (d, J=1.2 Hz, 2H), 3.18 (d, J=4.6 Hz, 1H), 2.36-2.34 (m, 1H), 2.22-2.14 (m, 1H), 2.09-2.00 (m, 2H), 1.92 (dd, J=15.8, 8.4 Hz, 1H), 1.66-1.57 (m, 2H), 1.46 (dd, J=14.0, 10.2, 5.1 Hz, 1H), 1.34 (s, 3H), 1.24 (s, 13H), 1.01-0.95 (m, 1H), 0.89 (s, 3H), 0.80 (d, J=7.0 Hz, 3H), 0.62 (d, J=7.1 Hz, 3H).

$^{13}$C NMR (151 MHZ, DMSO-d6) δ 215.14, 169.67, 165.52, 153.83, 149.01, 143.07, 138.58, 131.49, 129.09, 126.56, 125.61, 123.66, 113.29, 108.21, 70.58, 67.67, 58.75, 55.29, 46.58, 42.93, 42.06, 41.10, 39.51, 34.38, 32.28, 32.13, 31.99, 28.98, 28.10, 26.68, 24.59, 22.45, 14.08, 12.58, 9.48.

Example 12

Preparation of Compound l: 5-(3,5-dimethylbenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8]cyclo-5-yl)oxy)-2-oxoethyl)thio)-3H-imidazo[4,5-C]pyridine-5-ium

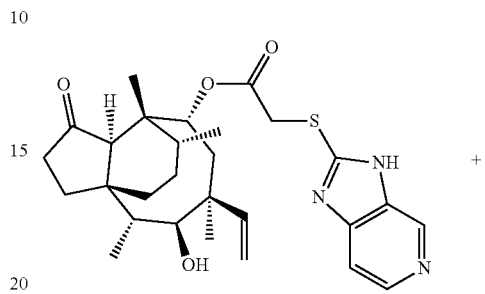

+

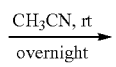

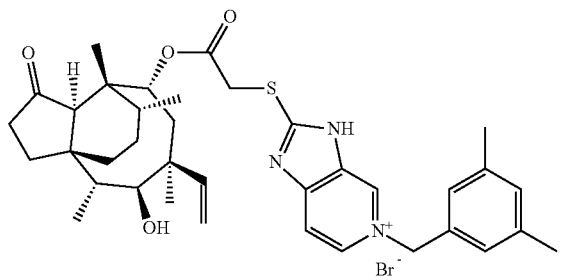

Figure 34:
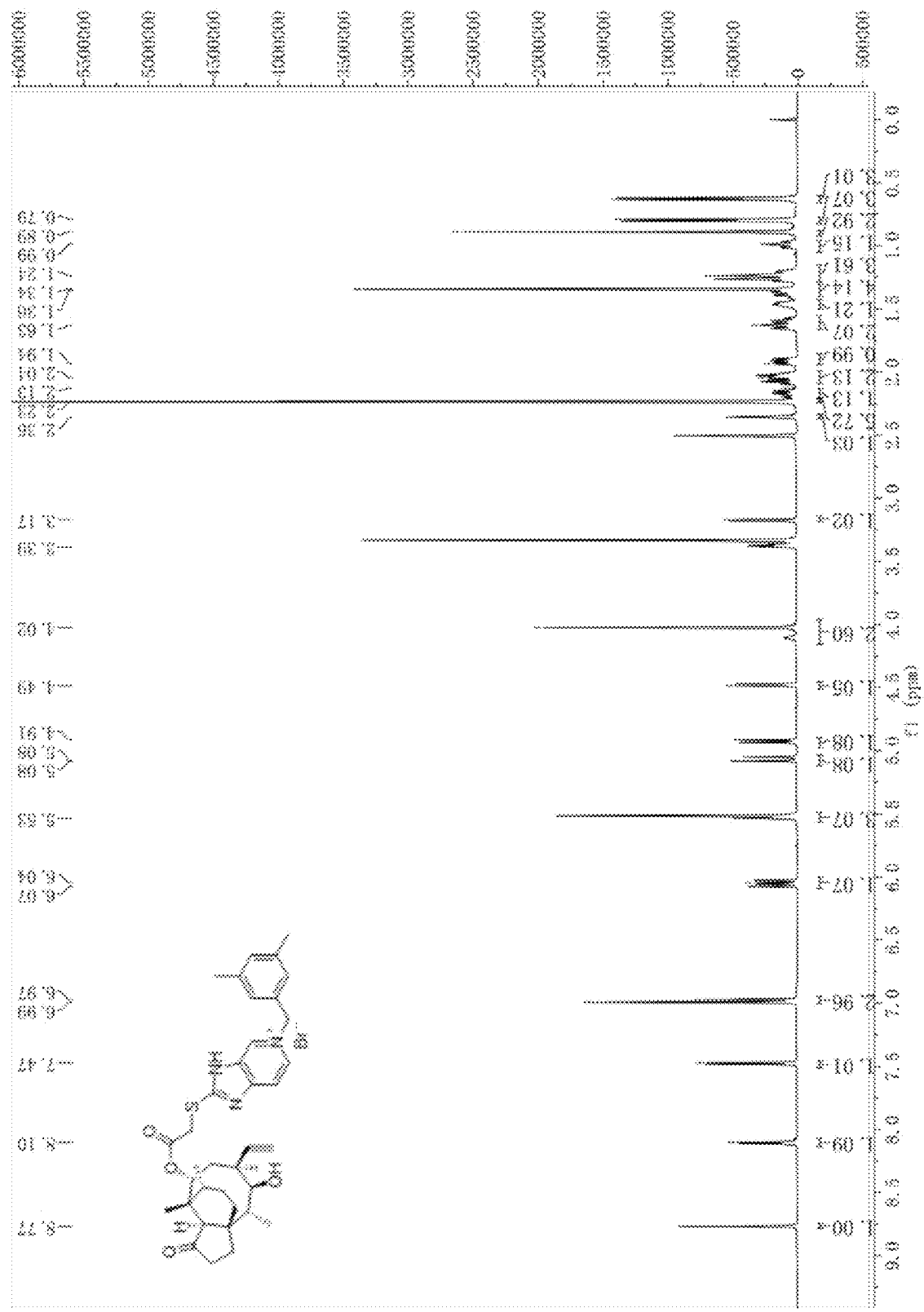
FIG. 34 is a $^1$H NMR spectrum of Compound l of the present invention in deuterated DMSO.
Figure 35:
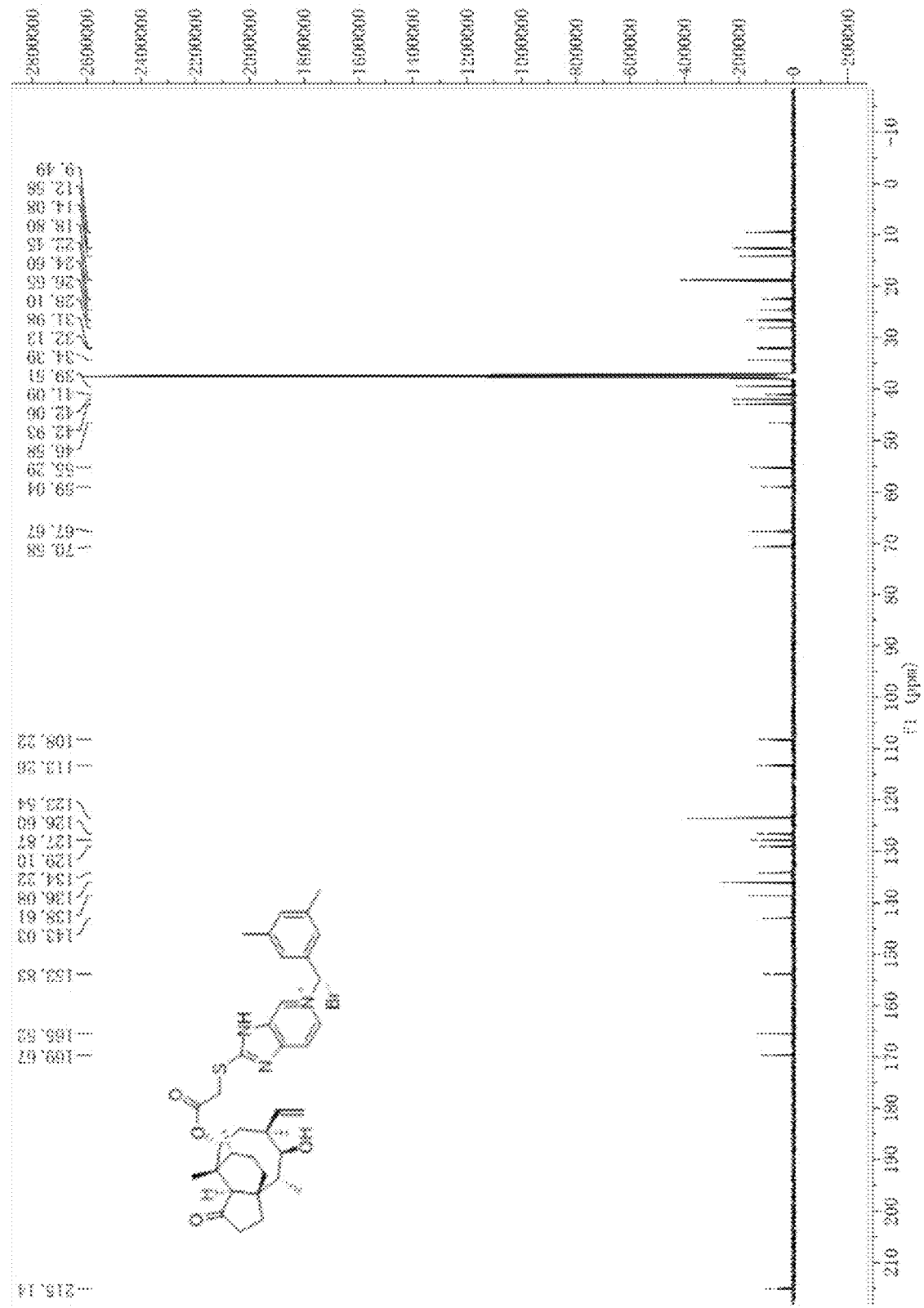
FIG. 35 is a $^{13}$C NMR spectrum of Compound l of the present invention in deuterated DMSO.

The preparation method was as described in Example 1, except that the corresponding raw materials were replaced. Yield of Compound l obtained: 75%. The 1H NMR spectrum of Compound l in deuterated DMSO is as shown in FIG. 34, and the 13C NMR spectrum in deuterated DMSO is as shown in FIG. 35.

$^1$H NMR (600 MHZ, DMSO-d6) δ 8.77 (d, J=1.6 Hz, 1H), 8.10 (dd, J=6.8, 1.6 Hz, 1H), 7.48 (d, J=6.7 Hz, 1H), 6.98 (d, J=12.5 Hz, 3H), 6.05 (dd, J=17.8, 11.2 Hz, 1H), 5.52 (d, J=10.8 Hz, 3H), 5.07 (dd, J=1.8 Hz, 1H), 4.93 (dd, J=1.2 Hz, 1H), 4.48 (d, J=6.0 Hz, 1H), 4.02 (s, 3H), 3.17 (d, J=4.3 Hz, 1H), 2.36 (d, J=2.7 Hz, 1H), 2.23 (s, 6H), 2.17 (dd, J=10.6 Hz, 1H), 2.09-1.99 (m, 2H), 1.92 (dd, J=15.8, 8.4 Hz, 1H), 1.66-1.55 (m, 2H), 1.46 (dtd, J=14.1, 7.1, 3.5 Hz, 1H), 1.34 (s, 4H), 1.25 (qd, J=6.2 Hz, 4H), 0.99 (td, J=4.2 Hz, 1H), 0.89 (s, 3H), 0.80 (d, J=7.0 Hz, 3H), 0.62 (d, J=7.0 Hz, 3H).

$^{13}$C NMR (151 MHz, DMSO-d6) δ 215.14, 169.67, 165.52, 153.83, 143.03, 138.61, 136.08, 134.22, 129.10, 127.87, 126.60, 123.54, 113.26, 108.22, 70.58, 67.67, 59.04, 55.29, 46.58, 42.93, 42.06, 41.09, 39.51, 34.39, 32.13, 31.98, 28.10, 26.65, 24.60, 22.45, 18.80, 14.08, 12.58, 9.49.

Example 13

Preparation of Compound m: 5-(2-cyano-5-fluorobenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8]cyclo-5-yl)oxy)-2-oxoethyl)thio)-3H-imidazo[4,5-C]pyridine-5-ium

Example 14

Preparation of Compound n: 5-(3,5-dimethoxybenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8]cyclo-5-yl)oxy)-2-oxoethyl)thio)-3H-imidazo[4,5-C]pyridine-5-ium

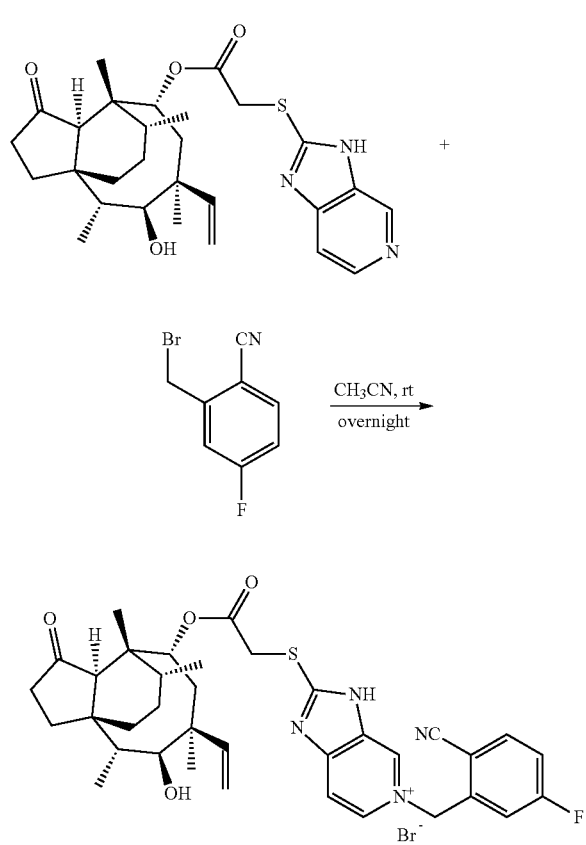 [SMILES: C=C[C@]1(C)C[C@@H](OC(=O)CSc2nc3ccncc3[nH]2)[C@]2(C)[C@H](C)CC[C@]3(CCC(=O)[C@H]32)[C@@H](C)[C@@H]1O ; N#Cc1ccc(F)cc1CBr ; "overnight" ; C=C[C@]1(C)C[C@@H](OC(=O)CSc2nc3cc[n+](Cc4cc(F)ccc4C#N)cc3[nH]2)[C@]2(C)[C@H](C)CC[C@]3(CCC(=O)[C@H]32)[C@@H](C)[C@@H]1O ; Br]

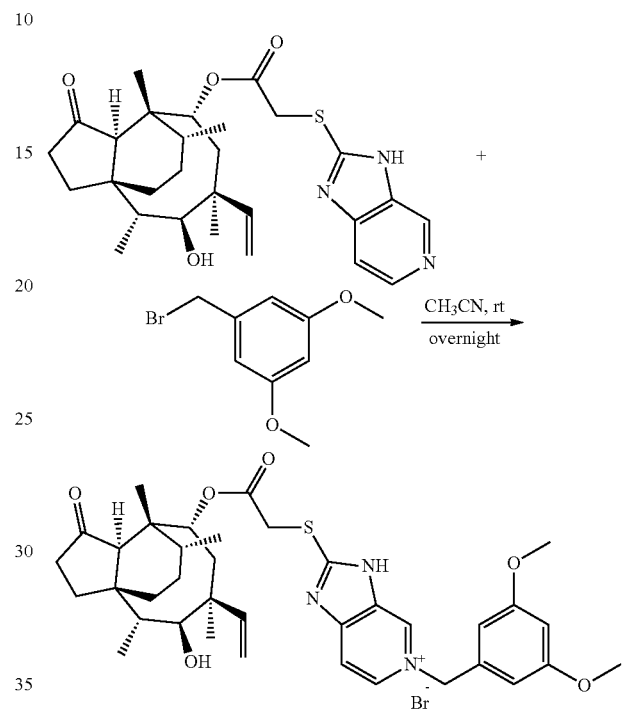

Figure 36:
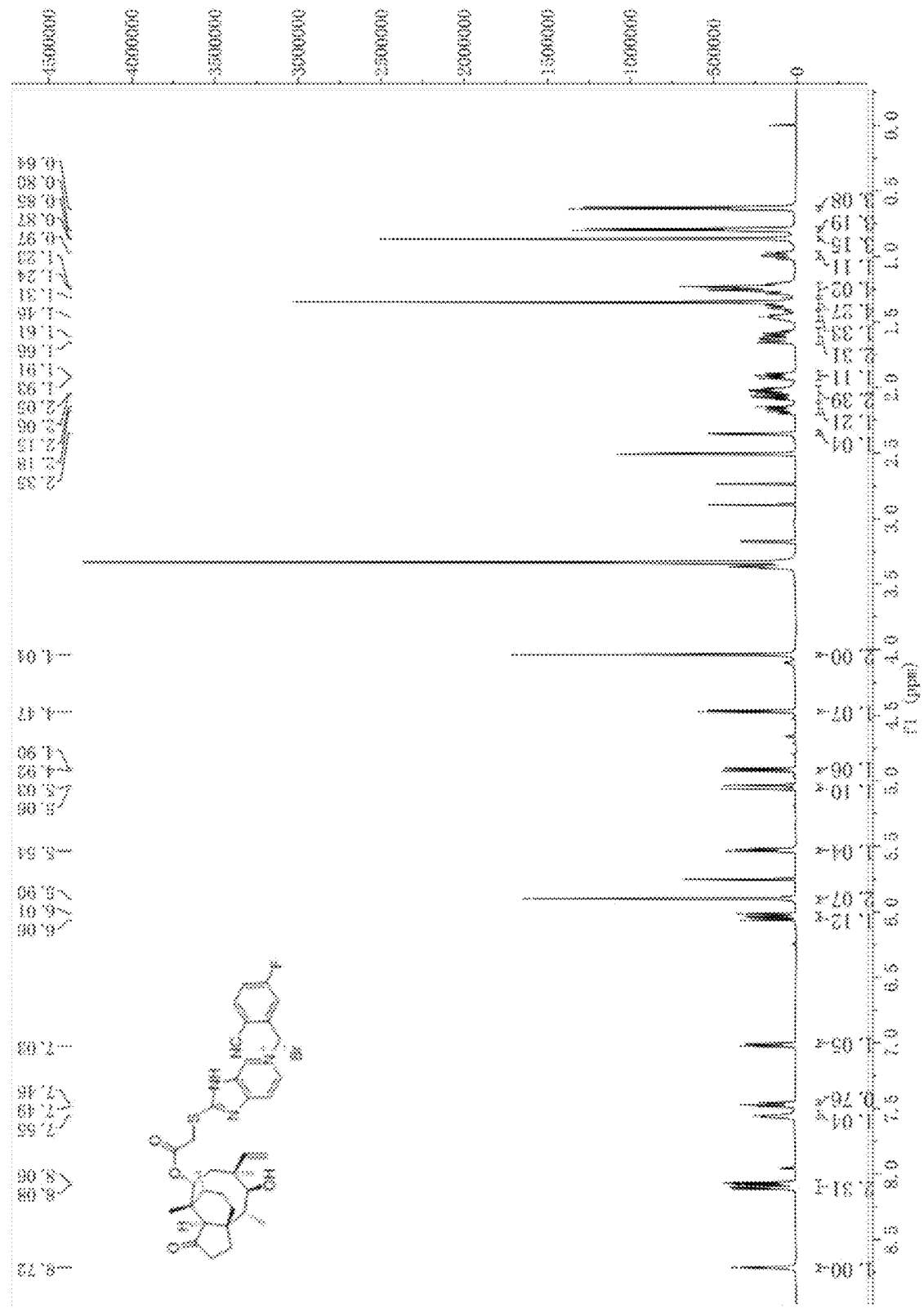
FIG. 36 is a $^1$H NMR spectrum of Compound m of the present invention in deuterated DMSO.
Figure 37:
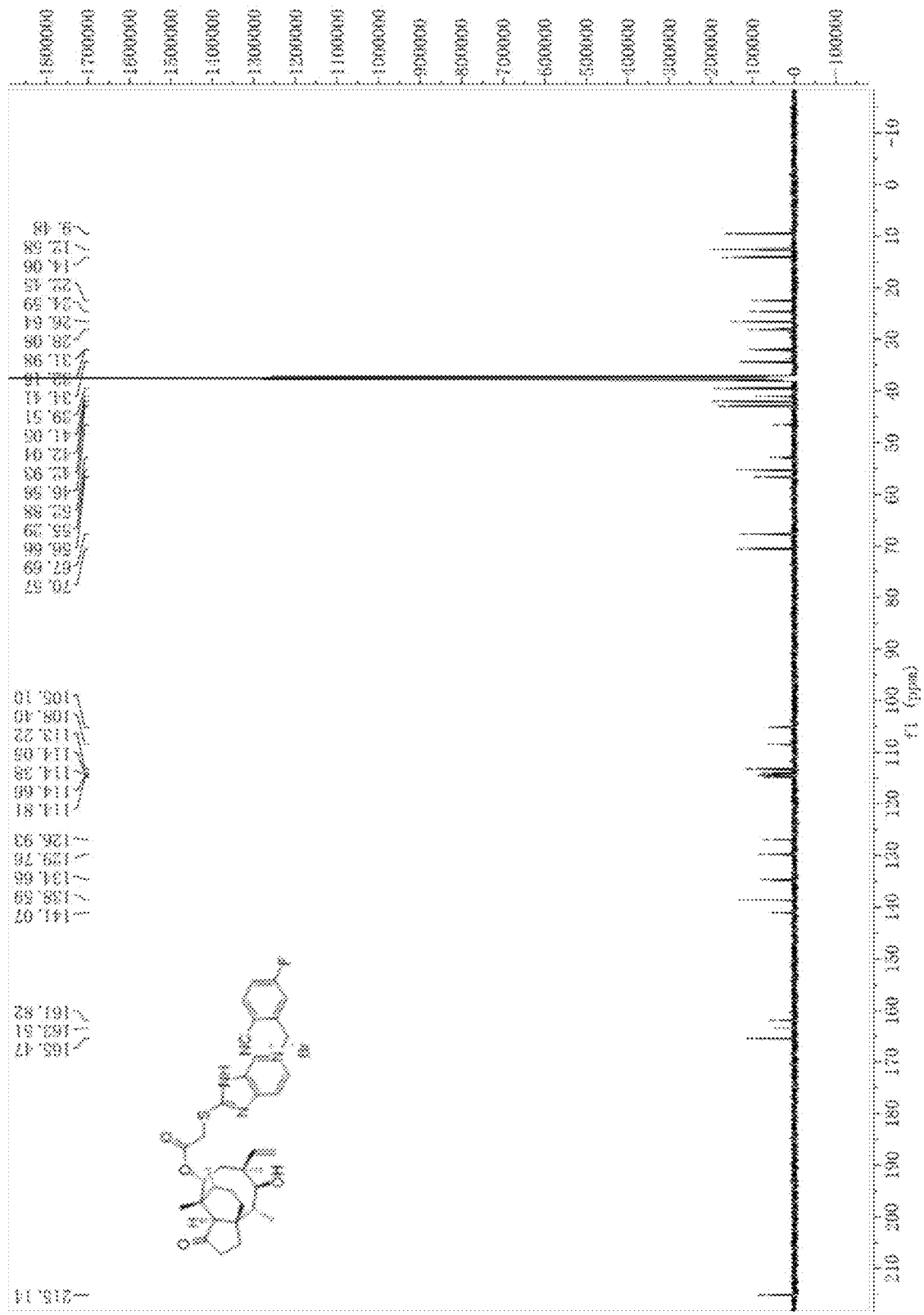
FIG. 37 is a $^{13}$C NMR spectrum of Compound m of the present invention in deuterated DMSO.

The preparation method was as described in Example 1, except that the corresponding raw materials were replaced. Yield of Compound m obtained: 72%. The 1H NMR spectrum of Compound m in deuterated DMSO is as shown in FIG. 36, and the $^{13}$C NMR spectrum in deuterated DMSO is as shown in FIG. 37.

$^1$H NMR (600 MHZ, DMSO-d6) δ 8.72 (s, 1H), 8.15-8.04 (m, 2H), 7.56 (d, J=6.8 Hz, 1H), 7.46 (dd, J=8.5, 2.6 Hz, 1H), 7.02 (dd, J=9.3, 2.6 Hz, 1H), 6.04 (dd, J=17.8, 11.2 Hz, 1H), 5.90 (s, 2H), 5.53 (d, J=8.4 Hz, 1H), 5.05 (dd, J=17.8, 1.7 Hz, 1H), 4.92 (dd, J=11.2, 1.7 Hz, 1H), 4.47 (d, J=6.1 Hz, 1H), 4.04 (s, 2H), 2.35 (d, J=2.7 Hz, 1H), 2.21-2.12 (m, 1H), 2.10-1.99 (m, 2H), 1.91 (dd, J=15.8, 8.4 Hz, 1H), 1.67-1.55 (m, 2H), 1.46 (ddt, J=14.9, 7.8, 4.1 Hz, 1H), 1.35 (s, 4H), 1.25 (ddt, J=18.8, 15.0, 6.9 Hz, 4H), 0.99 (td, J=14.0, 4.4 Hz, 1H), 0.87 (s, 3H), 0.80 (d, J=7.0 Hz, 3H), 0.63 (d, J=7.0 Hz, 3H).

$^{13}$C NMR (151 MHZ, DMSO-d6) δ 215.14, 165.47, 163.51, 161.82, 141.07, 138.59, 134.66, 129.76, 126.93, 114.81, 114.66, 114.38, 114.05, 113.22, 108.40, 105.10, 70.57, 67.69, 56.66, 55.29, 52.88, 46.58, 42.93, 42.04, 41.05, 39.51, 34.41, 32.15, 31.98, 28.08, 26.64, 24.59, 22.45, 14.06, 12.58, 9.48.

Figure 38:
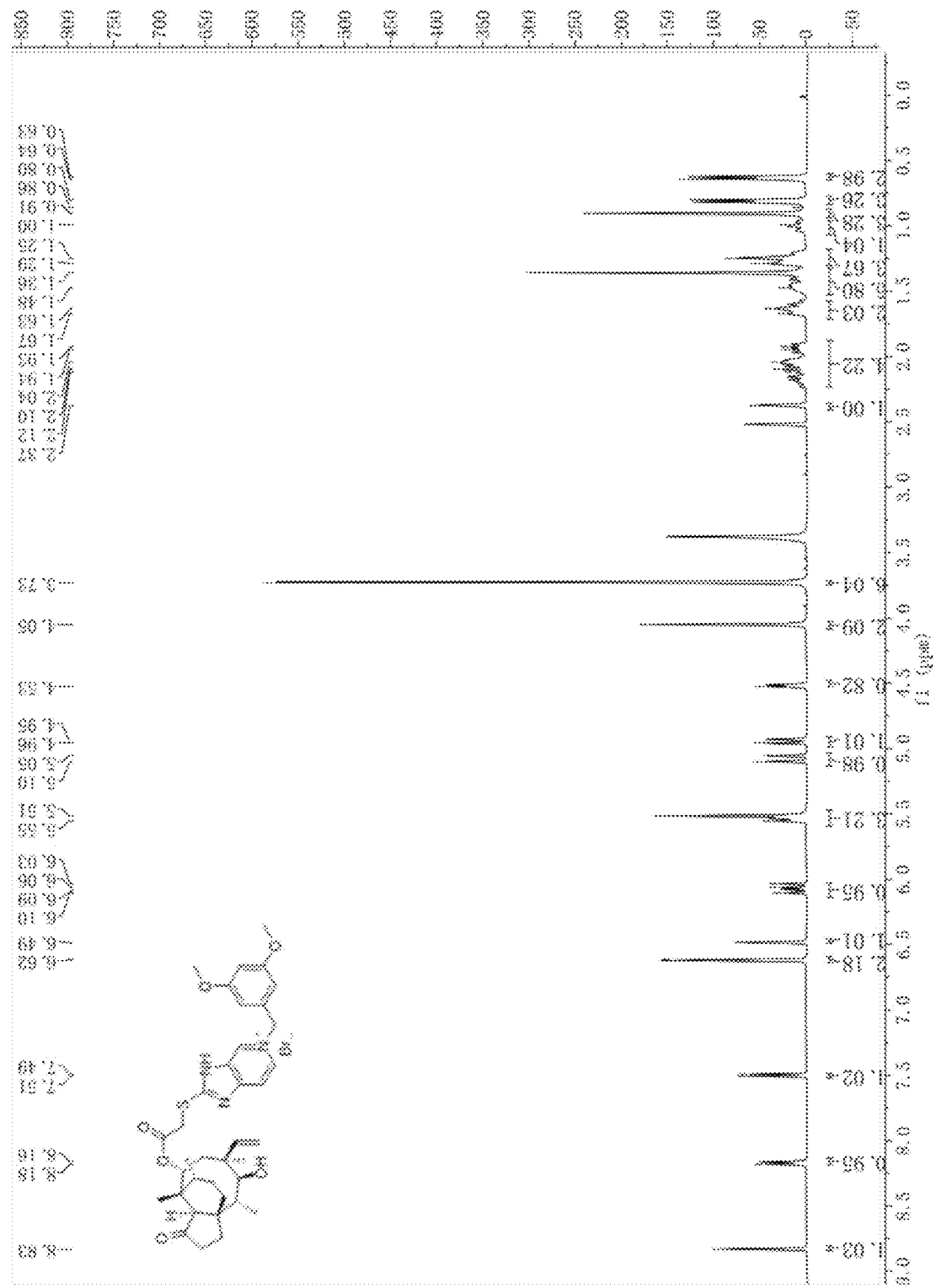
FIG. 38 is a $^1$H NMR spectrum of Compound n of the present invention in deuterated DMSO.
Figure 39:
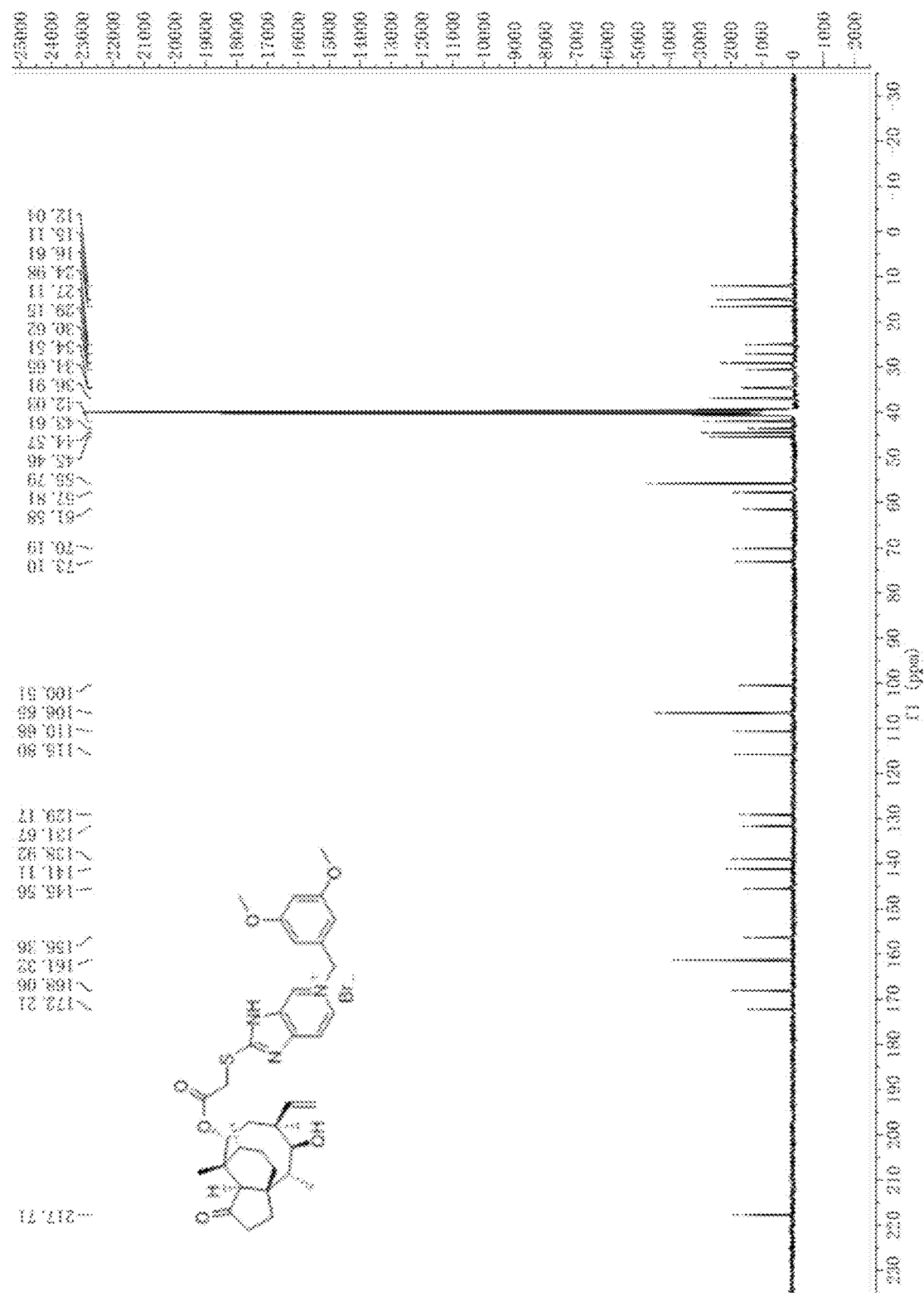
FIG. 39 is a $^{13}$C NMR spectrum of Compound n of the present invention in deuterated DMSO.

The preparation method was as described in Example 1, except that the corresponding raw materials were replaced. Yield of Compound n obtained: 76%. The 1H NMR spectrum of Compound n in deuterated DMSO is as shown in FIG. 38, and the 13C NMR spectrum in deuterated DMSO is as shown in FIG. 39.

$^1$H NMR (600 MHZ, DMSO-d6) δ 8.83 (d, J=1.7 Hz, 1H), 8.17 (dd, J=6.8, 1.6 Hz, 1H), 7.50 (d, J=6.7 Hz, 1H), 6.62 (d, J=2.3 Hz, 2H), 6.48 (t, J=2.2 Hz, 1H), 6.07 (dd, J=17.8, 11.2 Hz, 1H), 5.59-5.47 (m, 3H), 5.08 (dd, J=17.8, 1.8 Hz, 1H), 4.94 (dd, J=11.2, 1.8 Hz, 1H), 4.52 (d, J=6.1 Hz, 1H), 4.05 (s, 2H), 3.73 (d, J=1.4 Hz, 6H), 2.37 (s, 1H), 2.23-1.88 (m, 4H), 1.64 (t, J=14.6 Hz, 2H), 1.53-1.32 (m, 6H), 1.30-1.18 (m, 4H), 1.07-0.96 (m, 1H), 0.91 (s, 3H), 0.81 (d, J=6.8 Hz, 3H), 0.63 (d, J=6.7 Hz, 3H).

$^{13}$C NMR (151 MHz, DMSO-d6) δ 217.71, 172.21, 168.06, 161.32, 156.36, 145.56, 141.11, 138.92, 131.67, 129.17, 115.80, 110.68, 106.65, 100.51, 73.10, 70.19, 61.58, 57.81, 55.79, 45.46, 44.57, 43.61, 42.03, 36.91, 34.65, 34.51, 30.62, 29.15, 27.11, 24.98, 16.61, 15.11, 12.04.

Example 15

In Vitro Antibacterial Activity Assay of Compounds

The minimum inhibitory concentration of 3H-imidazo[4,5-C]pyridine pleuromutilin onium salt derivatives against the tested pathogenic microorganisms were determined by broth microdilution method, with valnemulin and retapamulin as positive controls.

The experimental strains included resistant Gram-positive bacteria: Methicillin-resistant *S. aureus* ATCC 33591; Methicillin-resistant *S. aureus* ATCC 43300; *S. aureus* ATCC 29213; Methicillin-resistant *S. epidermidis* ATCC 51625. Resistant Gram-negative bacteria: *A. baumannii* ATCC 19606; *S. enterica* ATCC14028; *E. coli* ATCC 25922; *E. coli* CMCC 44103. 9 clinically isolated resistant strains: MRSA-171; MRSA-575; MRSA-206; MRSA-222; MRSA-596; VRE-80; MDR-PA-126; MDR-KP-893; CR-AB-882.

The experimental strains were provided by Huashan Hospital Affiliated to Fudan University (Institute of Antibiotics, Fudan University) and used after identification by conventional methods.

The specific steps are as follows:

(1) Preparation of MHB medium: Weigh 18.0 g of MHB medium pre-made powder, add it to 1 L of distilled water, heat and boil until completely dissolved, divide it into conical bottles, sterilize it by high pressure at 121° C. for 15 minutes, and set aside.

(2) Cultivate the experimental strain to the logarithmic growth phase: Under sterile conditions, inoculate the experimental strain into fresh MHB medium and culture it in a 37° C. constant temperature and humidity incubator for 16-24 hours. Adjust the bacterial solution concentration to $1.5 \times 10^8$ CFU/mL and then dilute it 200 times for later use.

(3) Preparation of storage solution: Weigh the sample to be tested, dissolve it in 1% DMSO solution, and prepare a storage solution with a concentration of 2560 μg/mL; weigh the positive control, dissolve it in sterile distilled water, and prepare a storage solution with a concentration of 2560 μg/mL.

(4) Preparation of bacterial suspension: Under sterile conditions, the experimental strain cultured to the logarithmic growth phase was calibrated to a 0.5 McFarland unit turbidity standard using MHB medium and then diluted at a ratio of 1:200 to prepare a bacterial suspension with a concentration of $5 \times 10^5$ CFU/mL for later use.

(5) Determination of MIC by two-fold microdilution method: Take a sterile 96-well plate, add 10 μL of the test compound at a concentration of 2560 μg/mL, and perform serial dilutions by the two-fold dilution method. At the same time, set up a negative control group without drug. Then add 190 μL of diluted bacterial solution to each well, so that the final bacterial solution concentration in each well is $5 \times 10^5$ CFU/mL, and incubate in a 37° C. constant temperature and humidity chamber for 24 hours.

(6) MIC endpoint interpretation: The concentration that can completely inhibit the growth of bacteria in a 96-well plate observed by naked eye under a black background is the minimum inhibitory concentration of the sample for that type of bacteria. The results are recorded in TABLE 1 and TABLE 2.

TABLE 1

Minimum inhibitory concentration of the drug of the present invention and the positive control drug (μg · mL$^{-1}$)

| Compound | Gram-positive bacteria | | | | Gram-negative bacteria | | | |
|---|---|---|---|---|---|---|---|---|
| | MRSA[b] | MRSA[c] | S.a.[d] | MRSE[e] | A.b.[f] | S.e.[g] | E.c.[h] | E.c.[i] |
| a | 8 | 4 | 8 | 16 | 32 | 4 | 16 | 8 |
| b | 32 | 64 | 64 | 32 | 64 | 16 | 32 | 16 |
| c | 8 | 16 | 4 | 16 | 32 | 16 | 8 | 8 |
| d | 16 | 8 | 32 | 16 | 16 | 16 | 4 | 32 |
| e | 32 | 16 | 8 | 16 | 16 | 32 | 32 | 16 |
| f | 8 | 2 | 4 | 4 | 8 | 4 | 16 | 8 |
| g | 128 | 64 | 64 | 64 | 64 | 128 | 64 | 128 |
| h | 2 | 0.5 | 0.5 | 0.25 | 1 | 2 | 0.5 | 2 |
| i | 0.125 | 0.0625 | 0.0625 | 0.0625 | 0.25 | 0.25 | 0.125 | 0.125 |
| j | 32 | 16 | 4 | 32 | 16 | 8 | 64 | 8 |
| k | 8 | 32 | 16 | 8 | 16 | 32 | 32 | 32 |
| l | 64 | 32 | 64 | 64 | 64 | 32 | 64 | 64 |
| m | 64 | 32 | 32 | 64 | 64 | 32 | 64 | 32 |
| n | 64 | 32 | 32 | 64 | 64 | 128 | 64 | 32 |
| Valnemulin | 64 | 8 | 4 | 64 | 2 | 64 | 16 | 64 |
| Retapamulin | 32 | 16 | 4 | 32 | 4 | 128 | 32 | 32 |

MRSA[b]: [b]Methicillin-resistant *S. aureus* ATCC 33591;

MRSA[c]: [c]Methicillin-resistant *S. aureus* ATCC 43300;

S.a.[d]: [d]*S. aureus* ATCC 29213;

MRSE[e]: [e]Methicillin-resistant *S. epidermidis* ATCC 51625;

A.b.[f]: [f]*A. baumannii* ATCC 19606;

S.e.[g]: [g]*S. enterica* ATCC14028;

E.c.[h]: [h]*E. coli* ATCC 25922;

E.c.[i]: [i]*E.coli* CMCC 44103.

TABLE 2

Antibacterial activity of compounds I-8 and I-9 against 9 clinical isolates (µg · mL⁻¹)

| Compound | Clinical isolates | | | | | | | | |
|---|---|---|---|---|---|---|---|---|---|
| | MRSA[b] | MRSA[c] | MRSA[d] | MRSE[e] | MRSA[f] | VRE[g] | MDR-PA[h] | MDR-KP[i] | CR-AB[j] |
| h | 16 | 32 | 4 | 16 | 8 | 2 | 32 | 16 | 64 |
| i | 4 | 1 | 1 | 4 | 2 | 4 | 4 | 2 | 4 |
| Retapamulin | 128 | 32 | 64 | 128 | 32 | >128 | 64 | 128 | 64 |

[b]MRSA: methicillin-resistant *Staphylococcus aureus*-171;
[c]MRSA: methicillin-resistant *Staphylococcus aureus*-575;
[d]MRSA: methicillin-resistant *Staphylococcus aureus*-206;
[e]MRSA: methicillin-resistant *Staphylococcus aureus*-222;
[f]MRSA: methicillin-resistant *Staphylococcus aureus*-596;
[g]VRE: vancomycin-resistant *Enterococcus*-80;
[h]MDR-PA: multidrug-resistant *Pseudomonas aeruginosa*-126;
[i]MDR-KP: multidrug-resistant *Klebsiella pneumoniae*-893;
[j]CR-AB: carbapenem-resistant *Acinetobacter baumannii*-882.

As shown in TABLE 1, compounds a-n of the present invention have antibacterial effects on Gram-positive bacteria Methicillin-resistant *S. aureus* ATCC 33591, Methicillin-resistant *S. aureus* ATCC 43300, *S. aureus* ATCC 29213, Methicillin-resistant *S. epidermidis* ATCC 51625 and Gram-negative bacteria *A. baumannii* ATCC 19606, *S. enterica* ATCC14028, *E. coli* ATCC 25922, and *E. coli* CMCC 44103. Among them, the antibacterial effects of compounds h and i are significantly better than those of positive drugs valnemulin and retapamulin, and compound i has the best effect.

As shown in TABLE 2, compounds h and i of the present invention have antibacterial effects on 9 clinically isolated drug-resistant bacterial strains, and the antibacterial effects are significantly better than those of positive drugs valnemulin and retapamulin, and compound i has the best effect.

Example 16

In Vitro Anti-*Mycoplasma* Activity Assay of Compounds i

The antimycoplasma activity was quantified using the colony change units method. Retapamulin was used as a positive control to test the minimum inhibitory concentration of 3H-imidazo[4,5-C]pyridine pleuromutilin onium salt derivatives.

(1) Preparation of KM2 medium: Weigh 38.9 g of KM2 medium, add it to 800 mL of distilled water, boil to dissolve, sterilize under high pressure at 115° C. for 20 min, and set aside.

(2) Preparation of bacterial stock solution: Take 0.5 mL of Mhp-J[a], Mhp-LH[b], Mhr-BTS-7[c], MG-R[d], MS-WVU1853[e], MP-M129[f], CP-AR-39[g], CP-CWL-029[h], CP-TW-183[i], MH-PG-21[j], MG-G37[k] cultured to the logarithmic phase and transfer it to 4.5 mL of KM2 liquid culture medium. When the culture medium turns yellow, divide each bacterium into 0.5 mL per tube and store it at −70° C. as bacterial stock solution.

(3) Determination of bacterial titer (color change unit, CCU): Take out the bacterial stock solution stored at −70° C., melt and balance to room temperature, add 0.18 mL KM2 medium to each well of the middle 4 rows of the 96-well plate (i.e. 4 parallels), take 0.02 mL and add it to the first column, dilute 10 times to 10⁻¹¹, and set up a negative control containing only KM2 medium (12th column). After sealing, put it in a 37° C. incubator and observe the results every day. The highest dilution at which the color of the medium changes is the CCU/mL of the strain.

(4) Determination of MIC: Prepare a mother solution of 2560 µg/mL for each drug to be tested (retapamulin and the compound synthesized by the present invention), dilute each drug mother solution 2 times with KM2 liquid culture medium, and the test concentration range is 0.000004-128 µg/mL. Take an appropriate amount of seed bacterial solution and dilute it to 10⁴ CCU/mL in turn according to its titer. Add drugs of each dilution in a 96-well plate in turn, and then add an equal amount of diluted bacterial solution. Set 200 µL of diluted *mycoplasma* bacterial solution as a positive control, 200 µL of KM2 liquid culture medium as a negative control, and set a solvent control group (10 µL of drug solvent+190 µL of *mycoplasma* bacterial solution). Each experiment is set up in 3 parallels. After all culture plates are sealed, they are cultured at 37° C., observed daily, and the final MIC value is recorded. The results are recorded as shown in TABLE 3.

TABLE 3

Antimycoplasma activity of compound i (μg · mL$^{-1}$)

| Compound | Mhp-J[a] | Mhp-LH[b] | Mhr-BTS-7[c] | MG-R[d] | MS-WVU1853[e] | MP-M129[f] | CP-AR39[g] | CP-CWL-029[h] | CP-TW-183[i] | MH-PG-21[j] | MG-G37[k] |
|---|---|---|---|---|---|---|---|---|---|---|---|
| i | 0.02 | 0 | 0.03 | 0.04 | 0.015 | 0.008 | 0.002 | 0 | 0.01 | 0.015 | 0.03 |
| Retapamulin | 0.03 | 0 | 0.03 | 0.125 | 2 | 0.015 | 0.125 | 0.03 | 0.03 | 0.25 | 0.03 |

[a]*M. hyopneumoniae* J, NCTC10110.
[b]*M. hyopneumoniae* LH, clinicalisolate.
[c]*M. hyorhinis* BTS-7, NCTC10130.
[d]*M. gallisepticum*, NCTC10115.
[e]*M. synoviae* WVU1853, NCTC10124.
[f]*M. pneumoniae* M129, ATCC29342.
[g]*C. pneumoniae* AR39, ATCC53592.
[h]*C. pneumoniae* CWL-029, VR-1310.
[i]*C. pneumoniae* TW183, VR-2282.
[j]*M. hominis* PG-21, ATCC23114.
[k]*M. genitalium* G37, ATCC33530.

As shown in TABLE 3, compound i of the present invention has an inhibitory effect on 11 types of *mycoplasma*, and its inhibitory effect is better than that of the positive drug retapamulin.

Example 17

Study on the Time-Killing Curve of Compound i Against MRSA

Based on the MIC test results, the best performing active compounds were selected for time-kill curve studies.
(1) Preparation of mixed solution: Mix the test compound with the diluted bacterial solution to make the final concentrations 1×MIC, 2×MIC, 4×MIC and 8×MIC respectively. Incubate at 37° C.
(2) Sampling: At 0, 2, 4, 6, 8, 12, and 24 hours, aspirate 100 μL of the mixture
(3) Serial dilution and coating: Use 10 mM PBS buffer to dilute 10 times continuously, and evenly coat the diluted liquid on the agar plate
(4) Incubation and counting: Incubate in a 37° C. incubator for 24 hours and count the colonies.
(5) Sterilization curve drawing: Draw the curve of colony count change over time at different compound concentrations, and record the results as shown in FIG. 1.
As shown in FIG. 1, for MRSA (ATCC 33591) and *E. coli* (ATCC 25922), at each compound concentration, compared with retapamulin, compound i of the present invention can achieve the same bactericidal effect in a shorter time, that is, compound i of the present invention has a higher bactericidal efficiency.

Example 18

Figure 2:
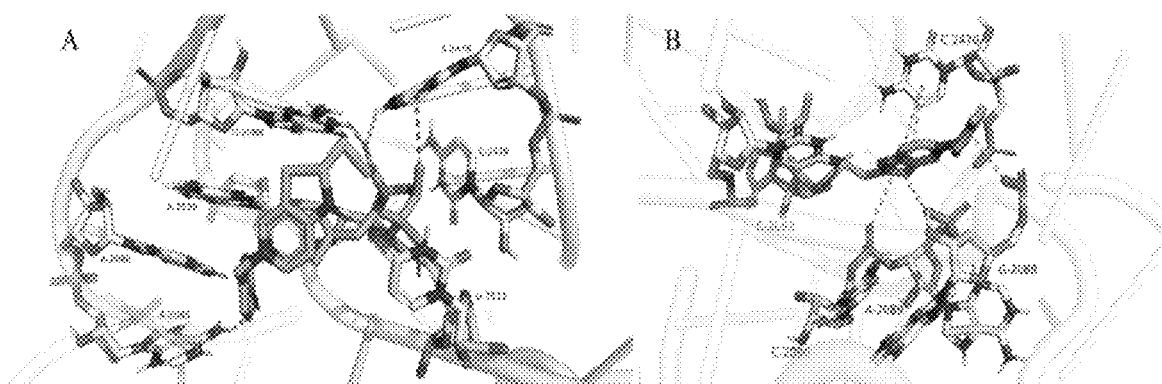
FIG. 2 is a docking diagram of compounds h, i and processed peptidyl transferase center (PDB code: 5HL7); A is a docking diagram of Compound h and 5HL7, and B is a docking diagram of Compound i and 5HL7.

Molecular Docking Study of Compounds h and i with Target Proteins (1) Data preparation: First, the three-dimensional structure of the macromolecular receptor (PDB ID: 5HL7) downloaded from the RCSB database was collected and prepared, based on the crystal structure of the complex of *S. aureus* and lefamulin. At the same time, the structural data of the small molecule drug (ligand) were obtained.
(2) Protein preparation: The structure of the target protein is processed, which includes removing water molecules, ions and other non-protein parts.
(3) Ligand preparation: Optimization and preparation of preferred small molecule drugs, which involves optimization of geometric structure, charge distribution, etc.
(4) Grid generation: Generate a three-dimensional grid around the active site of the protein to accelerate the calculation of the docking algorithm. This step is crucial to computational efficiency. The grid required for efficient docking calculations is generated by professional software.
(5) Docking calculation: AutoDock molecular docking software was used to perform calculations to predict the binding mode between ligand and protein.
(6) Binding mode analysis: After obtaining the docking results, the binding mode analysis is performed to see which binding modes are the most stable. The binding mode with the lowest energy is selected based on the energy score.
(7) Evaluate the results: Perform statistical analysis on the docking results to evaluate binding affinity, predict ligands with higher affinity, etc. This step is combined with experimental data and other computational results to ensure the reliability of the results. Use molecular visualization tools such as PyMOL, Chimera, etc. to visualize the final docking results, as shown in FIG. 2.
The binding free energy of a compound to a receptor molecule is usually less than −7 kcal/mol to show a strong antibacterial effect. The binding free energies of the test compound and the control drug valnimulin are both less than −7 kcal/mol. Compound 8i has a higher degree of compatibility with the cavity containing residues near the peptidyl transferase center, and its binding free energy is the lowest among the tested drugs, forming two hydrogen bonds and four Anion-π interactions, and the distances to the residues are all less than or equal to 2.6 Å, which may be the reason why compound i has stronger antibacterial activity.

Example 19

Effects of Compound i on Intracellular and Extracellular ATP Concentrations in Bacteria The intracellular and extracellular ATP levels refer to the concentration of ATP inside and outside the cell. Under normal physiological conditions, ATP is mainly produced inside the cell and released outside the cell when needed. This dynamic change is very important for maintaining normal biological homeostasis.

Determine the intracellular ATP concentration using the ATP assay kit:

First, samples were taken from MRSA and *E. coli* cultures in the logarithmic growth phase, and bacterial suspensions were prepared by high-speed centrifugation and washing with PBS buffer to remove the culture medium and residues, and then the optical density values were adjusted for subsequent experiments. Secondly, the bacterial suspension was treated with different concentrations of compound i, and a blank control group was set up. Next, the samples were incubated at 37° C. and the cells were lysed by ultrasound to extract ATP. After that, the supernatant was collected by high-speed centrifugation and ATP detection was performed, which involved adding the detection solution and compound to a 96-well plate and using a reader to measure the light intensity. Finally, data analysis and statistics were performed to evaluate the effects of the compound by comparing the ATP levels of different treatment groups. The results are shown in FIG. 3.

Figure 3:
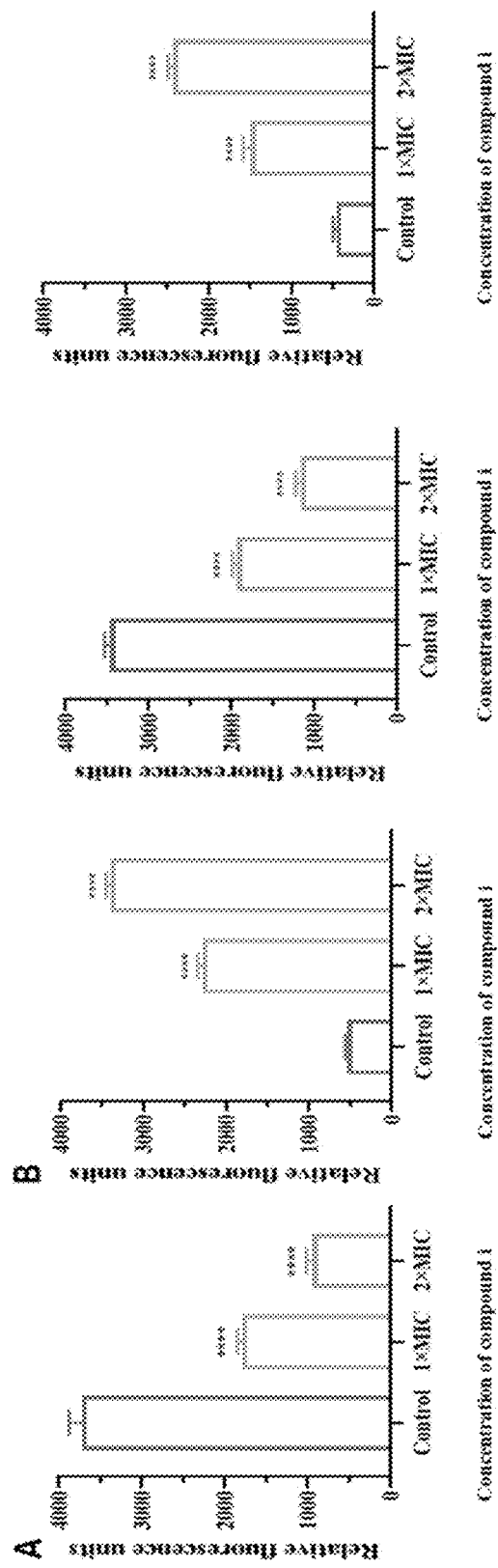
FIG. 3 shows the effect of different concentrations of Compound i on the concentration of ATP inside and outside bacterial cells. A shows the effect of Compound i on the concentration of ATP inside MRSA (ATCC 33591); B shows the effect of compound i on the concentration of ATP outside MRSA (ATCC 33591); C shows the effect of Compound i on the concentration of ATP inside *E. coli* (ATCC 25922); D shows the effect of Compound i on the concentration of ATP outside *E. coli* (ATCC 25922). ***$p<0.0001$ vs Control.

As shown in FIG. 3, compared with the blank control group, compound i showed a significant effect, significantly reducing the intracellular ATP concentration of bacteria ($p<0.0001$) and increasing the extracellular ATP concentration ($p<0.0001$). The results of the treatment of MRSA (ATCC 33591) and *E. coli* (ATCC 25922) at a concentration of 1×MIC showed that after treatment with i, the intracellular fluorescence intensity decreased by 51.92% and 50.75%, respectively, while the extracellular fluorescence intensity increased by 3.27 times and 4.34 times, respectively. At a concentration of 2×MIC, the intracellular fluorescence intensity decreased by 74.76% and 67.87%, respectively, while the extracellular fluorescence intensity increased by 2.28 times and 5.35 times, respectively. These results indicate that i can significantly change the permeability of bacterial cell membranes, leading to the leakage of intracellular ATP and exerting an antibacterial effect.

Example 20

Effects of Compound i on Intracellular pH of Bacteria

The definition of $pH_{in}$ is based on the ratio of the pH-sensitive wavelength (490 nm) to the pH-insensitive wavelength (440 nm).

First, prepare fluorescently labeled bacterial cells. MRSA and *E. coli* bacteria were removed from the culture in the logarithmic growth phase, and after high-speed centrifugation and washing with HEPES buffer, the bacteria were labeled with carboxyfluorescein succinimidyl ester (cFDA-SE), and the fluorescent dye was bound to the cells by incubation.

Next, PBS buffer was used to wash and remove the unbound fluorescent dye, and then the cells were suspended in the buffer and stored in a low-temperature environment. The second step was to determine the intracellular pH. The fluorescently labeled cell suspension was added to a test tube containing different concentrations of compound i and transferred to a black opaque 96-well plate for incubation. The fluorescence value was measured at specific excitation and emission wavelengths using a full-wavelength scanning multifunctional reader to calculate the intracellular pH. The last step is the calibration of the intracellular pH. The standard curve was determined using buffer solutions with different pH values to ensure accurate determination of the pH value inside the bacterial cells. The pH values inside and outside the cells were balanced by adding valinomycin and nigericin during the measurement process to obtain more accurate results. The results are shown in FIG. 4.

Figure 4:
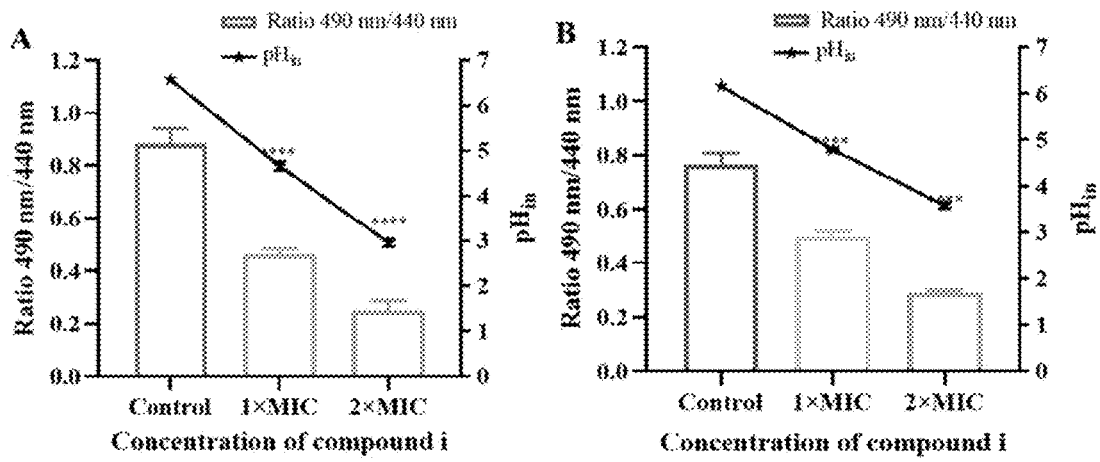
FIG. 4 shows the effect of different concentrations of Compound i on bacterial intracellular pH. A is MRSA (ATCC 33591); B is *E. coli* (ATCC 25922). ****$p<0.0001$ vs Control.

As shown in FIG. 4, compared with the blank control group, i significantly reduced the pH value of bacterial cells ($p<0.0001$). At 1×MIC concentration, compound i treatment of MRSA (ATCC 33591) reduced the intracellular pH from 6.57±0.10 to 4.66±0.12, and at 2×MIC concentration, the intracellular pH further decreased to 2.96±0.09. For *E. coli* (ATCC 25922), compound i treatment reduced its intracellular pH from 6.16±0.10 to 4.79±0.10 and 3.58±0.10 under 1×MIC and 2×MIC conditions, respectively.

Example 21

Effect of Compound i on Bacterial Cell Membrane Potential

Monitoring membrane potential using the fluorescent probe DiBAC4 (3) provides intuitive insights into the electrophysiological properties of cell membranes. DiBAC4 (3) is a slow-acting fluorescent probe whose fluorescence signal changes in response to changes in membrane potential. In depolarized cells, it binds to intracellular proteins or membranes, resulting in an increase in fluorescence intensity; whereas in hyperpolarized cells, DiBAC4 (3) results in a decrease in fluorescence intensity.

The membrane potential of MRSA (ATCC 33591) and *E. coli* (ATCC 25922) in the logarithmic growth phase was measured using the fluorescent probe Bis(1,3-dibutylbarbituric acid)trimethine oxonol (DiBAC4 (3)).

First, MRSA and *E. coli* were cultured to the logarithmic growth phase, and then the bacterial cell suspension was prepared by high-speed centrifugation and washing with PBS buffer. Next, the cell suspension was mixed with DiBAC4 (3) dye in a black 96-well plate. This dye is used to measure membrane potential. After incubation for 30 minutes, the fluorescence intensity was measured on a full-wavelength scanning multifunctional reader, with the excitation wavelength set to 492 nm and the emission wavelength set to 515 nm. In the third step, after waiting for the fluorescence intensity to stabilize, different concentrations of compound i, including 1×MIC, 2×MIC, 4×MIC and 8×MIC, were added to the bacterial suspension, and a control group was set up without adding the compound. The mixture was incubated again for 5 minutes to observe the effect of the compound on the membrane potential. The last step was to re-measure the fluorescence intensity at the same excitation and emission wavelengths to evaluate the effect of the compound on the bacterial membrane potential. In addition, adding the compound to the culture medium can help measure and correct the background fluorescence value to ensure the accuracy of the experimental data. The results are shown in FIG. 5.

Figure 5:
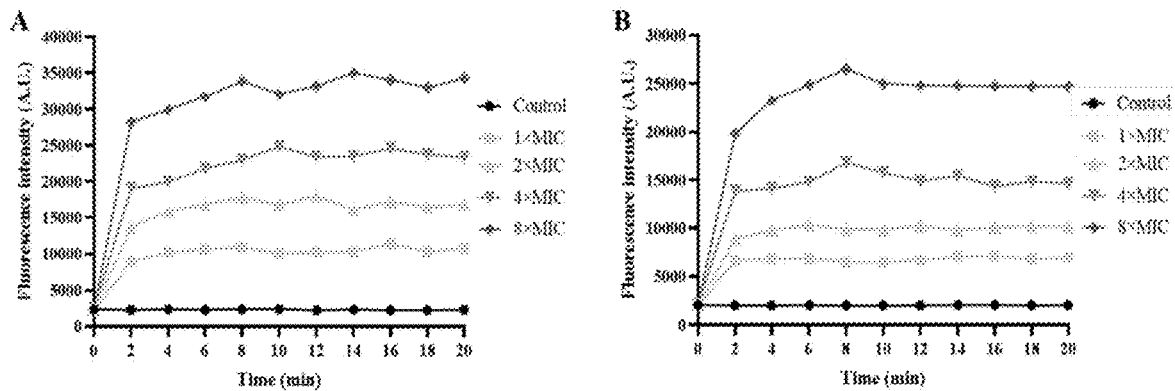
FIG. 5 shows the effect of different concentrations of Compound i on bacterial cell membrane potential. A is MRSA (ATCC 33591); B is *E. coli* (ATCC 25922).

As shown in FIG. 5, compared with the blank control group, MRSA cells treated with i showed a significant increase in fluorescence intensity. As the concentration of the compound gradually increased, the fluorescence intensity showed a significant dose-dependent increase. This intuitively reflects the effect of i on the membrane potential of MRSA cells. Similarly, *E. coli* treated with i showed a dose-dependent increase in fluorescence intensity, indicating that i caused the depolarization of the cell membrane, thereby exerting an antibacterial effect.

Example 22

Effect of Compound i on Bacterial Extracellular Conductivity

Changes in conductivity can reflect the permeability and integrity of the cell membrane. When the cell membrane is damaged or the permeability increases, the flow of ions inside and outside the cell will increase, resulting in an increase in conductivity. In the fields of biology and cell biology, conductivity measurements are often used to assess changes in cell membrane integrity.

MRSA and *E. coli* cells in the logarithmic growth phase were first resuspended after high-speed centrifugation and repeated PBS buffer washing and adjusted to the appropriate optical density. Next, different concentrations of compound i (1×MIC and 2×MIC) were added to the cell suspension, and a blank control group was set. All samples were incubated at 37° C. and sampled at set time points (0, 1, 2, 4, 6, and 8 hours). After sampling, the samples were centrifuged at high speed to remove cells, and finally the conductivity of the supernatant was measured to evaluate the effect of the compound on bacterial membrane permeability. This series of operations helps to reveal the specific mechanism of action of compound i on bacterial growth and cell structure. The results are shown in FIG. 6.

Figure 6:
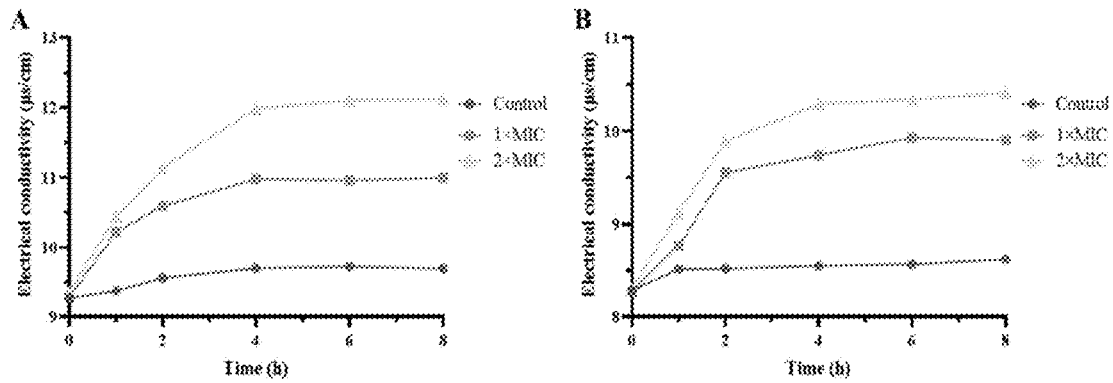
FIG. 6 shows the effect of different concentrations of Compound i on the conductivity of bacteria. A is MRSA (ATCC 33591); B is *E. coli* (ATCC 25922).

As shown in FIG. 6, compared with the blank control group, the extracellular conductivity of MRSA (ATCC 33591) and *E. coli* (ATCC 25922) treated with compound i increased, indicating that compound i destroyed the cell membranes of these two bacteria, that is, compound i can destroy the integrity of bacterial cell membranes, thereby exerting an antibacterial effect.

Example 23

Inhibitory Effect of Compound i on Bacterial Biofilm Formation

Quantification of biofilm using crystal violet staining:
MRSA and *E. coli* cells were first adjusted to the logarithmic growth phase and diluted to 106 CFU/mL. In a 96-well plate, 100 μL of compound i at different concentrations (0.5×MIC, 1×MIC, 2×MIC, 4×MIC, and 8×MIC) and 100 μL of diluted bacterial solution were added to each well and then incubated at 37° C. for 24 hours. A blank control group without compound addition was set up. After incubation, the suspension was discarded and washed three times with 10 mM PBS buffer, and the biofilm was fixed with methanol for 15 minutes. After removing the methanol, 200 μL of 0.1% crystal violet was added to each well for staining for 30 minutes, and then the crystal violet was discarded and washed again with PBS three times. After the well plate was dried, 200 μL of 95% ethanol was added to each well to dissolve the fixed dye. Finally, the absorbance value was measured at a wavelength of 595 nm using a full-wavelength scanning multi-function reader to evaluate the effect of the compound on biofilm formation. This process allows for quantitative analysis of the ability of different concentrations of compound i to form biofilms. The experimental results are shown in FIG. 7.

Figure 7:
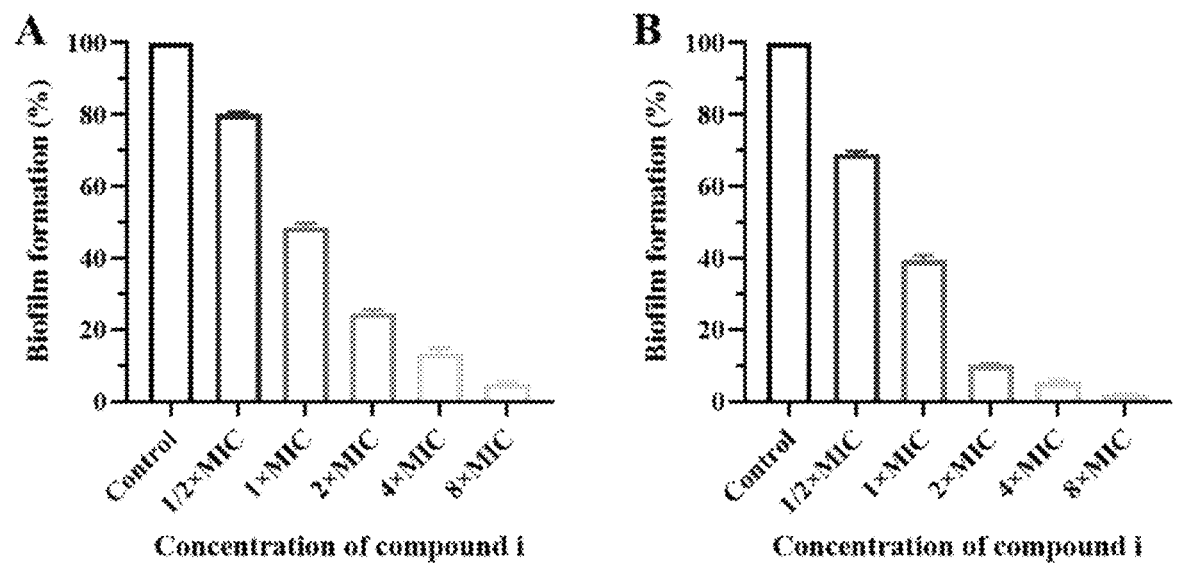
FIG. 7 shows the effect of different concentrations of Compound i on bacterial biofilm formation. A is MRSA (ATCC 33591); B is *E. coli* (ATCC 25922).

As shown in FIG. 7, compared with the control group, the addition of i significantly inhibited the formation of bacterial biofilms. When MRSA (ATCC 33591) and *E. coli* (ATCC 25922) were exposed to 1×MIC concentration of i, the inhibition rates of biofilm formation reached 51.33% and 60.47%, respectively. As the concentration of i increased to 8×MIC, the inhibition rates of biofilm formation of MRSA (ATCC 33591) and *E. coli* (ATCC 25922) increased to 86.68% and 94.54%, respectively. These results clearly show that 8i has the ability to destroy bacterial biofilm formation in a dose-dependent manner.

Example 24

Analysis of Bacterial Cell Membrane Integrity after Treatment with Compound i

The steps for dead cell staining using propidium iodide are as follows:

At the beginning of the experiment, samples were taken from MRSA and *E. coli* in the logarithmic growth phase, centrifuged at 8000 rpm for 5 minutes and washed twice with 0.85% NaCl solution to remove the culture medium and other possible interfering substances. Afterwards, the bacteria were resuspended in 0.85% NaCl solution and the concentration was adjusted to approximately $1\times10^8$ CFU/mL.

Next, drug treatment was performed, and compound i at 1×MIC and 4×MIC concentrations were added to 2 mL of cell suspension, and incubated at 37° C. for 2 hours with shaking to allow the compound to fully act on the bacteria. After incubation, in order to mark and distinguish dead cells, 15 μM propidium iodide solution was added to each sample and incubated in the dark for 15 minutes. PI is a fluorescent dye that binds to DNA and can only penetrate into dead cells with damaged cell membranes.

Finally, the samples were observed using a fluorescence microscope or a confocal laser scanning microscope. By setting the appropriate fluorescence channel (excitation wavelength 535 nm, emission wavelength 617 nm), the red fluorescence emitted by dead cells can be detected. In this way, the effect of compound i on the lethality of bacterial cells can be intuitively evaluated and recorded, providing an experimental basis for further drug research. The experimental results are shown in FIG. 8.

Figure 8:
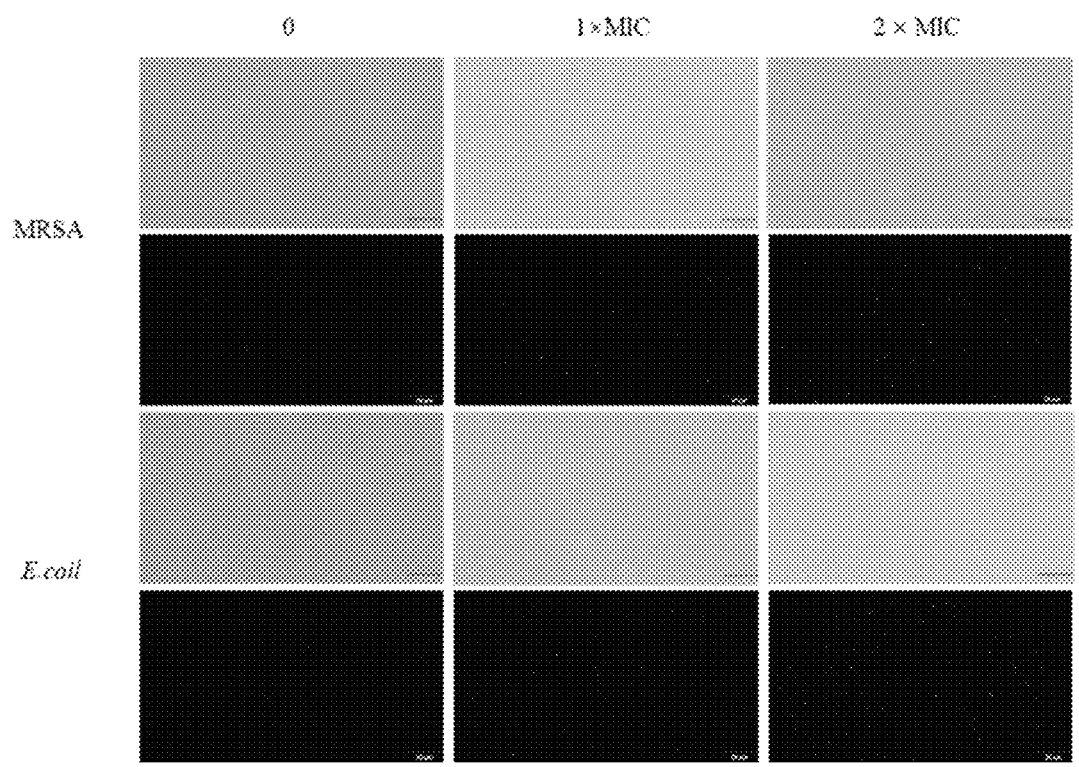
FIG. 8 shows the effects of different concentrations of Compound i on the cell membrane integrity of MRSA (ATCC 33591) and *E. coli* (ATCC 25922), scale bar: 20 μm.

As shown in FIG. 8, the blank control group showed almost no red fluorescence, indicating that the cell membranes of MRSA (ATCC 33591) and *E. coli* (ATCC 25922) were basically intact. After treating MRSA (ATCC 33591) and *E. coli* (ATCC 25922) with compound i at a concentration of 1×MIC, obvious red fluorescence was observed, indicating that the integrity of the cell membranes was damaged. When the concentration of compound i increased to 2×MIC, the red fluorescence was significantly enhanced. These experimental results indicate that compound i can disrupt the integrity of bacterial cell membranes, leading to bacterial death.

Example 25

Observation of Bacterial Cell Morphology after Treatment with Compound i

Observation of bacterial cell morphology using FESEM:
First, the bacterial suspension was adjusted to OD600=0.5, and then the bacteria were treated with compound i at a final concentration of 1×MIC and 4×MIC at 37° C. for 4 hours, and a control group without compound addition was set up. After treatment, the bacteria were collected by high-speed centrifugation at 6000 rpm for 10 minutes and washed three times with 10 mM PBS buffer to remove residual culture medium and drugs. Subsequently, the bacteria were fixed with 2.5% glutaraldehyde at 4° C. for 12 hours to maintain the integrity of the cell structure, and then washed again with PBS buffer three times to remove excess glutaraldehyde.

Next, the cells were subjected to a series of ethanol dehydration treatments (30%, 50%, 70%, 80%, 90% and 100% ethanol), and the treatment time of each concentration was sufficient to replace the intracellular water. After dehydration, the sample was resuspended in isoamyl acetate for 30 minutes and then centrifuged at 6000 rpm for 10 minutes to remove the supernatant. The sample was then dried and dotted on a stage with conductive glue, gold-plated to enhance the conductivity of the sample, and finally observed using a field emission scanning electron microscope (FE-SEM) to obtain high-resolution images of bacterial cell morphology and surface morphology. This process allows in-depth analysis of the specific effects of compound i on bacterial cell structure. The experimental results are shown in FIG. 9.

Figure 9:
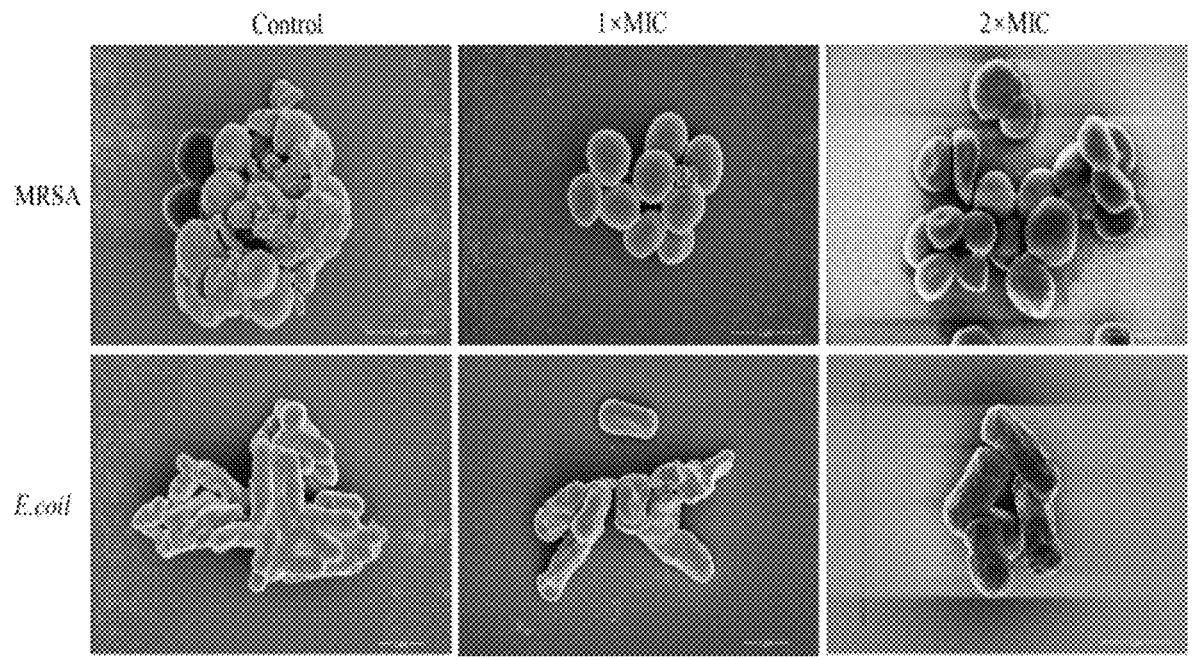
FIG. 9 shows the effects of different concentrations of Compound i on the cell morphology of MRSA (ATCC 33591) and *E. coli* (ATCC 25922), scale bar: 1 μm.

As shown in FIG. 9, the bacteria in the control group were directly observed by FESEM to have normal morphology, showing a round or nearly spherical cell morphology with a smooth and uniform surface. However, after treating MRSA (ATCC 33591) with compound i at a concentration of 1×MIC, the biofilm outside the bacteria was basically completely removed, and the shape of the cells was no longer completely spherical, but showed an irregular shape. When the concentration increased to 4×MIC, there was no biofilm outside the bacteria, and the morphology of the bacteria changed significantly, showing obvious shrinkage or deformation. Under the electron microscope, it was observed that the bacterial cells showed the characteristics of shrinkage and flattening.

For *E. coli* (ATCC 25922), after treatment with compound i at a concentration of 1×MIC, the biofilm on the surface gradually decreased, the biofilm was partially broken and thinned, and depressions on the bacterial surface were observed. As the concentration of compound i increased to 4×MIC, there was no biofilm outside the bacteria, and the bacterial morphology changed significantly, with obvious wrinkles and shrinkage on the bacterial surface.

Example 26

Safety Evaluation of Compound i

Cell Counting Kit-8 was used to evaluate the cytotoxicity of the compounds.

(1) Preparation: 10 mM PBS buffer: Dissolve 8.00 g NaCl, 0.20 g KCl, 1.44 g $Na_2HPO_4$, and 0.24 g $KH_2PO_4$ in 800 mL distilled water and adjust the pH to 7.4. Then, dilute to 1 L with distilled water and sterilize for 40 minutes before use.

(2) Preparation of bottom agar medium: Take 6.00 g agar powder and dissolve it in 400 mL distilled water. Stir well and then autoclave for 40 minutes to ensure the sterility of the medium. Then, when the solution cools to 60-70° C., add 8 mL of VS solution and 8 mL of GS solution. After adding each solution, mix thoroughly to ensure uniform distribution. Finally, pour the mixed agar solution into a plate to prepare the bottom agar medium.

(3) Preparation of top agar medium: First, weigh 1.20 g agar powder and 1.00 g NaCl, and add 200 ml distilled water. After mixing, autoclave for 40 minutes to ensure the sterility of the medium. Next, when the solution cools to 60° C., add 1.00 mL of HBT solution and mix thoroughly. Finally, take 2 mL of the mixture and dispense it into sterile test tubes. This part of the medium needs to be kept warm until use, usually in a water bath to maintain it at 45° C.

(4) Cell culture: HepG2, HEK293 and A549 cells were evenly dispersed in culture medium, seeded into 96-well plates, and cultured under appropriate environmental conditions to keep the cells completely attached to the well walls.

(5) Compound treatment: Add different concentrations of compounds I-8 and I-9 to each well (the concentrations are 0.78, 1.56, 3.13, 6.25, 12.5, 25, 50 and 100 µM, respectively, and perform 6 parallel experiments). Set up a blank control group and a normal control group. After incubation for 24 hours, observe the cell condition, which observed under a microscope.

(6) CCK-8 solution treatment: Add CCK-8 solution to each well and incubate for 4 hours to allow it to react with the cells.

(7) Absorbance determination: Use a full-wavelength scanning multifunctional reader, place the 96-well plate in the instrument, oscillate to mix to make the color evenly distributed, and measure the absorbance value at 490 nm.

(8) Data analysis: Based on the measured absorbance values, the cell survival rate at different concentrations can be calculated. The median cytotoxic concentration was used to evaluate the cytotoxicity of the compound to A549, HEK293 and HepG2 cells. The experimental results are shown in TABLE 4.

TABLE 4

Cytotoxicity test results of compounds h, i, retapamulin and valnemulin

| Compound | $CC_{50}$ (µM) | | |
| --- | --- | --- | --- |
| | HepG2 Cells | HEK293 Cells | A549 Cells |
| h | 96.34 | >100 | >100 |
| i | >100 | 96.36 | >100 |
| Retapamulin | 61.14 | 57.47 | 71.53 |
| Valnemulin | 77.26 | 65.38 | 53.74 |

As can be seen from TABLE 4, the CC50 of compounds h and i of the present invention on HepG2, HEK293 and A549 cells are all around 100 or more than 100, while the CC50 of retapamulin and valnemulin are both below 100 and lower than the CC50 of compounds h and i, indicating that the cytotoxicity of compounds h and i is very low, significantly lower than the positive drugs retapamulin and valnemulin.

Example 27

Establishment of a mouse model of MRSA systemic infection (1) Solution preparation and bacterial activation: Reference Example 15.

(2) Pretreatment: All mice received cyclophosphamide treatment, with the first intraperitoneal injection of 150 mg/kg cyclophosphamide 4 days before infection and the second intraperitoneal injection of 100 mg/kg cyclophosphamide 1 day before infection.

(3) Control group treatment: Mice in the blank control group received intraperitoneal injection of 0.9% saline.

(4) Infection process: Mice were anesthetized with isoflurane and infected by intraperitoneal injection of *Staphylococcus aureus* (MRSA, ATCC 33591) at a concentration of 107 CFU/mL.

Example 28

Determination of Mouse Survival Rate and Median Effective Dose (1) Experimental groups: The doses of compound i and valnemulin were 5, 10, and 20 mg/kg, respectively (the solvent was dimethyl sulfoxide: Tween-80: sterile water=1: 0.5:9.5);

A model control group (administered with a solvent after infection with bacteria) and a blank control group (administered with a solvent only without infection with bacteria) were set up, with 10 mice in each group, half of which were male and half were female.

(2) Time point: Intraperitoneal injection was performed in the experimental group mice at 1 hour after infection.

(3) Therapeutic dose: The mice in the experimental groups received intraperitoneal injection of 0.5 mL of compound i and valnemulin at different concentrations.

(4) Experimental observation and analysis: The 7-day survival rate and behavior of the animals after a single dose administration were observed. On day 7, all surviving mice were euthanized, and major organs were collected and divided into two parts, one for histochemical analysis and the other for colony counting. The mice were observed twice a day during the experiment to monitor symptoms and death. The survival rate of the mice 7 days after infection was taken as the endpoint, and a survival curve was prepared. SPSS 27 software was used to calculate $ED_{50}$ (median effective dose, $ED_{50}$) based on the Bliss method. The experimental results are shown in FIG. 10.

Figure 10:
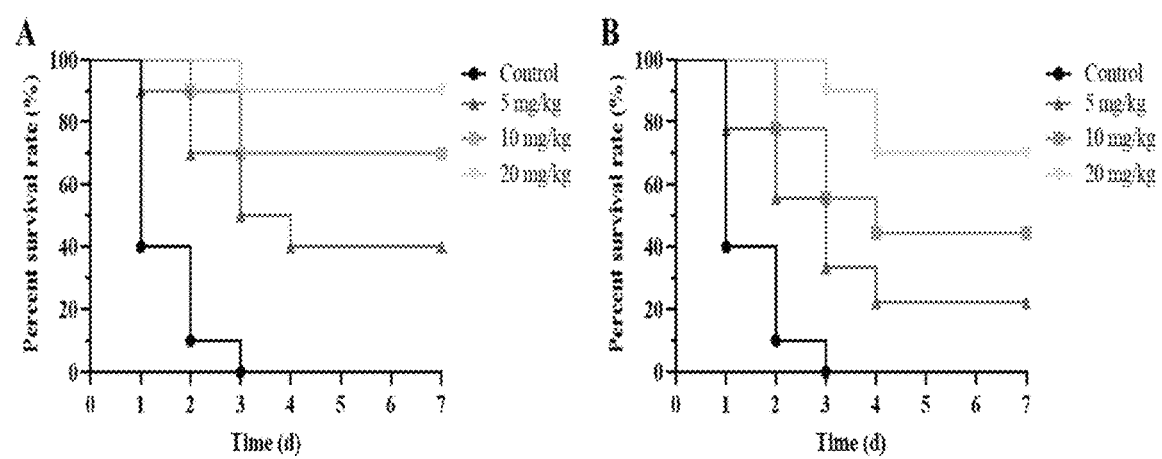
FIG. 10 shows the survival rates of Compound i (A) and valnemulin (B) in a mouse systemic infection model.

As shown in FIG. 10, compared with the blank control group, the survival rate of mice given compound i and warnemulin was improved, and the survival rate of mice given compound i was significantly higher than the survival rate of mice given warnemulin, indicating that the compound i has anti-MRSA activity and can improve the survival rate of MRSA-infected mice.

Example 29

Tissue Bacterial Load Detection and Tissue Section Observation (1) Experimental groups: The doses of compound i and valnemulin were 10 and 20 mg/kg, respectively (the solvent was dimethyl sulfoxide: Tween-80: sterile water=1:0.5:9.5); a model control group and a blank control group were set up, with 10 mice in each group, half of which were male and half were female.

(2) Processing:
(a) Time point: At the first hour after infection, mice in the experimental group received intraperitoneal injection of 0.5 mL of compounds of different concentrations, while mice in the control group received the same volume of solvent.
(b) Treatment time: Observe within 2 days after administration.

(3) Sampling:
(a) Euthanasia of mice: 2 days after treatment, the mice were euthanized.
(b) Organ processing: The lungs, kidneys and liver are divided into two parts.

Part 1: After weighing, homogenize with sterile saline, dilute and inoculate on agar medium. After incubation at 37° C. for 24 h, count the number of viable colonies (expressed in CFU/mL) and calculate the bacterial load (expressed in CFU/g).

Part II: The samples were fixed with 10% formalin buffer, then embedded in paraffin and sectioned. The sections were stained with hematoxylin and eosin (H&E) and then examined under an optical microscope. The results are shown in FIG. 11.

Figure 11:
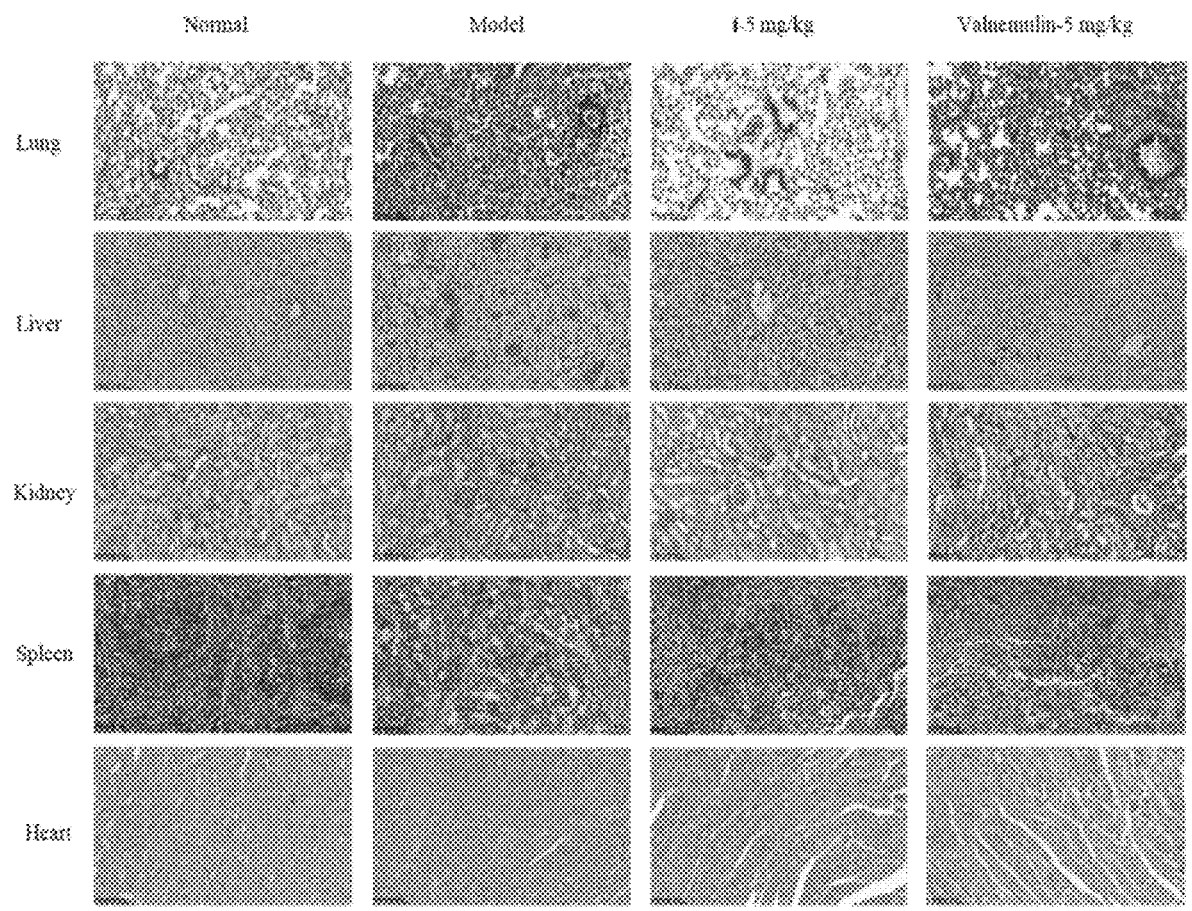
FIG. 11 shows representative H&E stained sections of major organs after different treatments, scale bar: 100 μm.

As shown in FIG. 11, in the lung model group, lung tissue damage caused by bacterial infection was observed, with destruction of the alveolar wall, thickening of the alveolar interstitium and proliferation of fibrous tissue. Inflammatory cells (mainly neutrophils) infiltrated and formed inflammatory foci. However, after treatment with 5 mg/kg compound i, clear airway structure, alveoli and interstitium were presented, with no obvious pathological changes. Symptoms in the valnemulin group were alleviated, but they still did not return to normal.

In the liver model group, inflammatory reactions, inflammatory cell infiltration, and liver tissue damage caused by bacterial infection were observed in the liver model group. Under H&E staining, it was observed that the nuclei of hepatocytes were enlarged, the staining degree was deepened, and the hepatocytes were degenerated or even necrotic. After treatment with 5 mg/kg compound i, it was similar to the normal control, but the valnemulin group still had inflammatory cell infiltration.

Pathological features related to immune response were observed in the spleen model group, and macrophages were significantly active. The immune response was weakened in the 5 mg/kg compound i and valnemulin groups after 7 days of treatment.

Mild tubular interstitial inflammatory infiltration was observed in the renal model group, which returned to a normal state after treatment with 5 mg/kg compound i. However, inflammatory cell infiltration was still observed in the valnemulin group, and the inflammatory response led to deeper staining.

There were no effects in the cardiac bacterial infection group or the drug treatment group, and staggered arrangement of striated muscle cells with clear nuclear morphology was observed without obvious pathological changes or inflammatory response.

The invention claimed is:

1. A compound of formula I, a pharmaceutically acceptable salt, or a tautomer thereof:

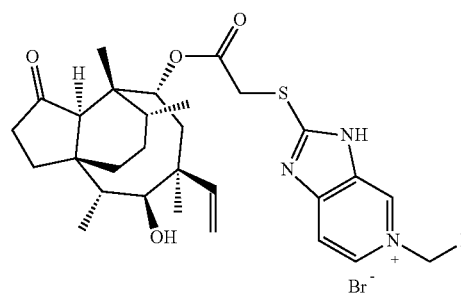

Formula I wherein R is a phenyl group substituted with an electron withdrawing group or a phenyl group substituted with an electron donating group.

2. The compound according to claim 1, wherein the compound is selected from the group consisting of:

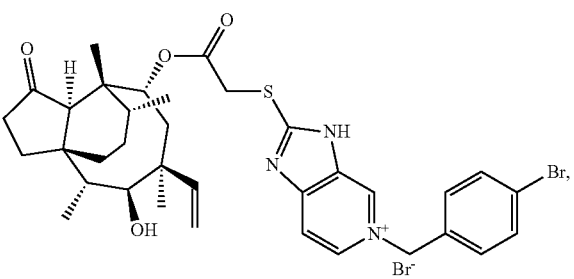

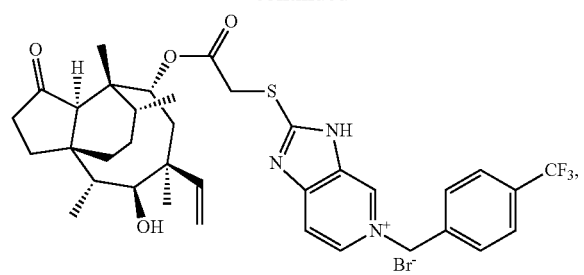
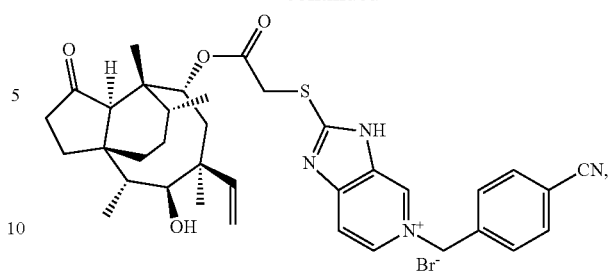
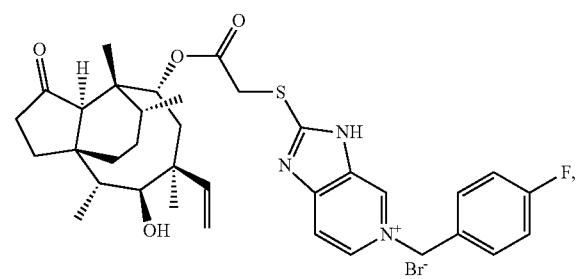
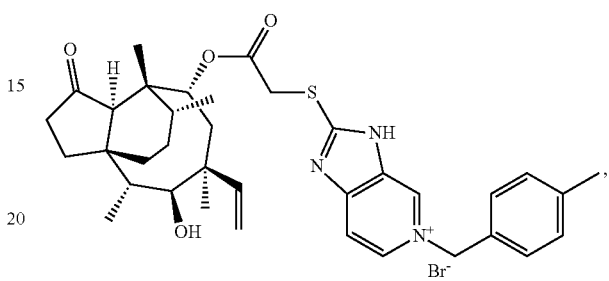
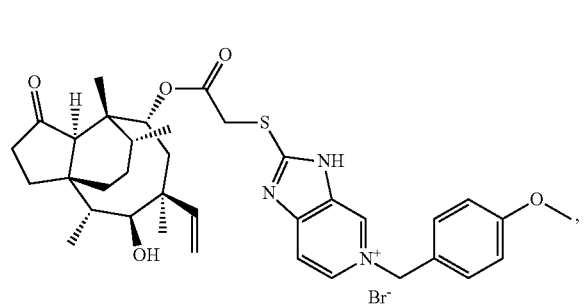
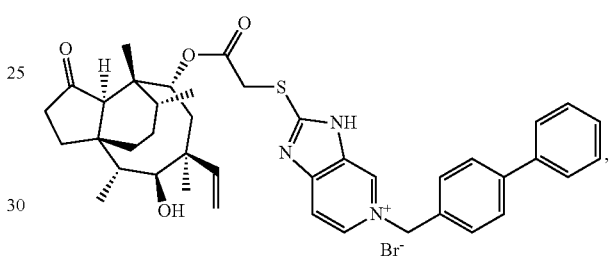
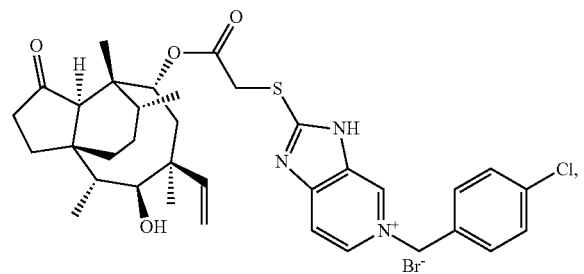
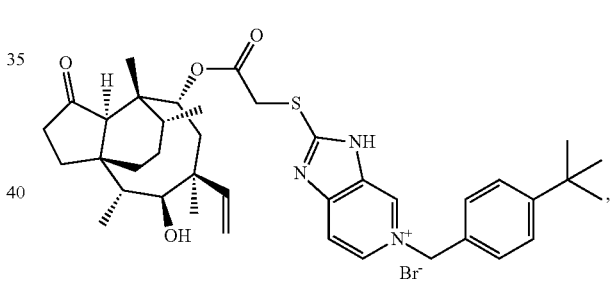
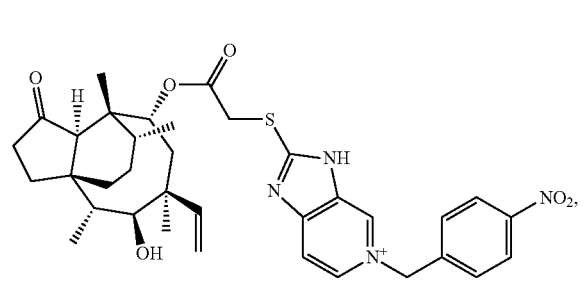
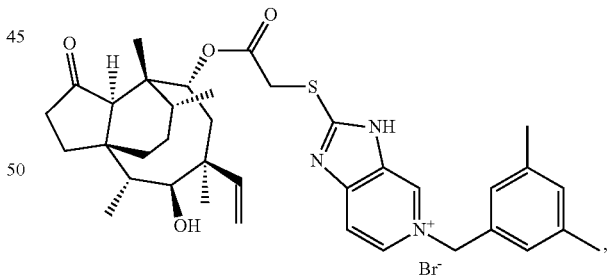
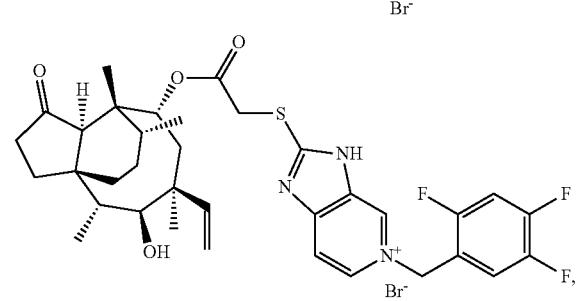
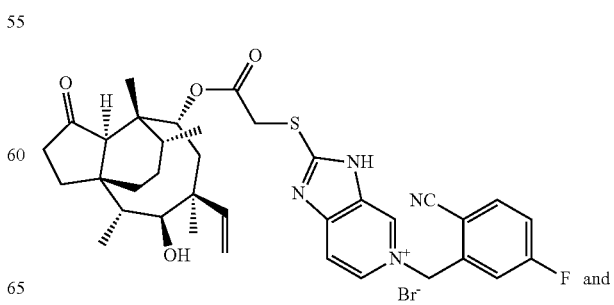

-continued

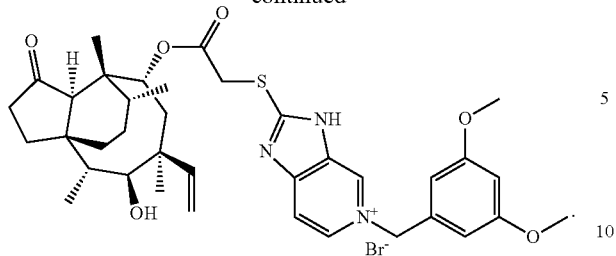

3. The compound according to claim 1, wherein the compound of formula I is selected from the group consisting of the following compounds:

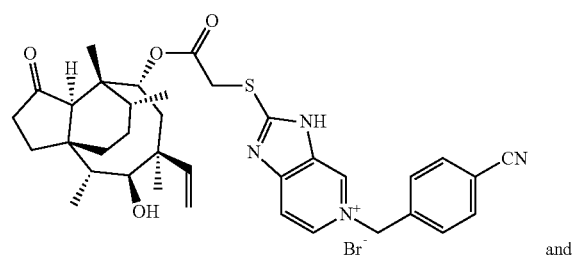

and

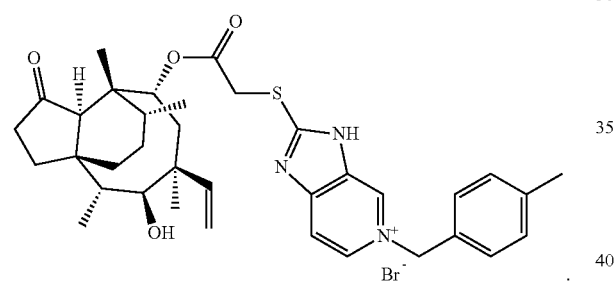

4. The compound according to claim 1, wherein the compound of formula I is:

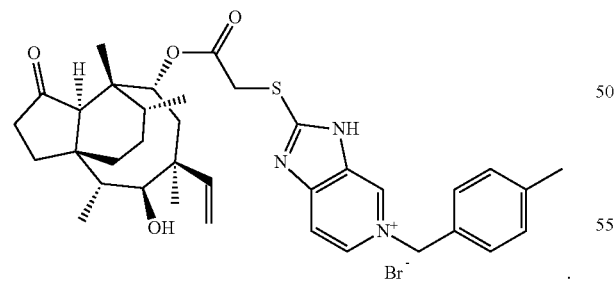

5. The compound according to claim 1, wherein the pharmaceutically acceptable salt comprises one selected from the group consisting of hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid and aspartic acid.

6. A method for preparing the compound according to claim 1, comprising the following steps:
(1) reacting pleuromutilin with tosyl chloride to obtain an intermediate I, wherein the intermediate I is

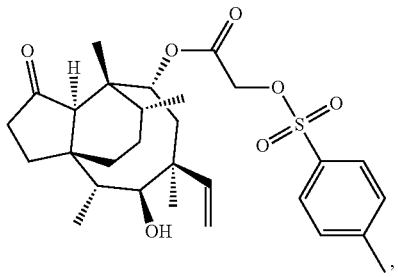 [SMILES: C=C[C@]1(C)C[C@@H](OC(=O)COS(=O)(=O)c2ccc(C)cc2)[C@]2(C)[C@H](C)CC[C@]3(CCC(=O)[C@H]32)[C@@H](C)[C@@H]1O]

(2) reacting 3,4-diaminopyridine with potassium ethyl xanthate to obtain an intermediate II, wherein the intermediate II is

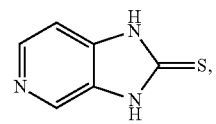

(3) reacting the intermediate I and the intermediate II under an alkaline catalyst condition with heating to obtain an intermediate III, wherein the intermediate III is

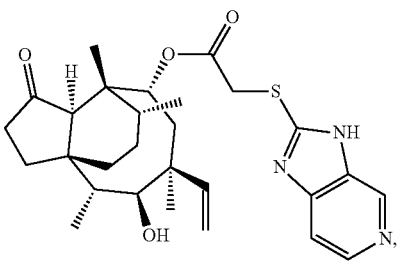 [SMILES: C=C[C@]1(C)C[C@@H](OC(=O)CSc2nc3ccncc3[nH]2)[C@]2(C)[C@H](C)CC[C@]3(CCC(=O)[C@H]32)[C@@H](C)[C@@H]1O]

(4) reacting the intermediate III with a substituted benzene ring compound to obtain the compound of formula I, wherein the formula I is Formula I

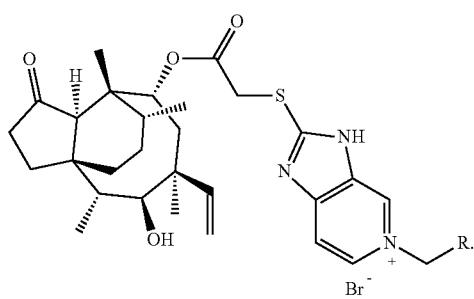

7. The method according to claim 6, wherein the substituted benzene ring compound is p-bromobenzyl bromide, 4-(trifluoromethyl)benzyl bromide, p-fluorobenzyl bromide, 4-methoxybenzyl bromide, 4-chlorobenzyl bromide, p-nitrobenzyl bromide, 1-bromo-2,4,5-trifluorobenzene, 4-cyanobenzyl bromide, p-methylbenzyl bromide, 4-bromomethylbiphenyl, 4-tert-butylbenzyl bromide, 3,5-dimethylbenzyl bromide, 2-cyano-5-fluorobenzyl bromide or 3,5-dimethoxybenzyl bromide.

8. A pharmaceutical composition, comprising the compound of claim 1 as an active ingredient.

* * * * *